(12) United States Patent
Yomano et al.

(10) Patent No.: US 8,716,002 B2
(45) Date of Patent: May 6, 2014

(54) RE-ENGINEERING BACTERIA FOR ETHANOL PRODUCTION

(75) Inventors: Lorraine P. Yomano, Gainesville, FL (US); Sean W. York, Gainesville, FL (US); Shengde Zhou, Dekalb, IL (US); Keelnatham Shanmugam, Gainesville, FL (US); Lonnie O. Ingram, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 874 days.

(21) Appl. No.: 12/375,484

(22) PCT Filed: Aug. 8, 2007

(86) PCT No.: PCT/US2007/017646
§ 371 (c)(1),
(2), (4) Date: Oct. 29, 2009

(87) PCT Pub. No.: WO2008/021141
PCT Pub. Date: Feb. 21, 2008

(65) Prior Publication Data
US 2010/0112656 A1 May 6, 2010

Related U.S. Application Data

(60) Provisional application No. 60/836,726, filed on Aug. 9, 2006.

(51) Int. Cl.
*C12N 1/21* (2006.01)
*C12N 15/70* (2006.01)

(52) U.S. Cl.
USPC ........................................ 435/252.3; 435/471

(58) Field of Classification Search
None
See application file for complete search history.

(56) References Cited

U.S. PATENT DOCUMENTS

| | | | |
|---|---|---|---|
| 5,482,846 A | 1/1996 | Ingram et al. | |
| 5,916,787 A | 6/1999 | Ingram et al. | |
| 6,102,690 A * | 8/2000 | Ingram et al. | 431/161 |
| 6,280,986 B1 | 8/2001 | Hespell et al. | |
| 2003/0008363 A1 | 1/2003 | Ingram et al. | |
| 2010/0112656 A1 * | 5/2010 | Yomano et al. | 435/161 |

FOREIGN PATENT DOCUMENTS

| | | |
|---|---|---|
| WO | 94/06924 A1 | 3/1994 |
| WO | 01/00857 A1 | 1/2001 |
| WO | 0118222 A1 | 3/2001 |

OTHER PUBLICATIONS

WO-Form PCT/ISA/210—International Search Report for PCT/US2007/017646, Aug. 14, 2008, University of Florida Research Foundation, Inc.

WO-Form PCT/ISA/237—Written Opinion for PCT/US2007/017646, Aug. 14, 2008, University of Florida Research Foundation, Inc.
EPO Form 1507N, EP, Nov. 3, 2010, Extended European Search Report for EP07811186.1.
A. Martinez, et al. Biotechnol. Prog. 15: 891-897 (1999).
L.P. Yomano, et al. Biotechnol. Lett. 30: 2097-2103 (2008).
Arfman N. et al., Use of the tac Promoter and lacIq for the controlled expression of *Zymomonas mobilis* Fermentative Genes in *Escherichia coli* and *Zymomonas mobilis*, Journal of Bacteriology, Nov. 1992, v. 174, No. 22, p. 7370-7378.
Condon Ciaran et al., Comparison of the expression of the seven ribosomal RNA operons in *Escherichia coli*, The EMBO Journal, 1992, vol. 11, No. 11, p. 4175-4185, particularly p. 4175, introduction.
Causey T.B., et al., Engineering *Escherichia coli* for efficient conversion of glucose to pyruvate, PNAS, Feb. 24, 2004, v. 101, No. 8, p. 2235-2240.
Chao, Yun-Peng et al., Molecular cloning of the carboxylesterase gene and biochemical characterization of the encoded protein from *Pseudomonas citronellolis* ATCC 13674, Research in Microbiology, Sep. 2003, v. 154, issue 7, p. 521-526 [found Oct. 30, 2009] found in Internet <URL:http://www.sciencedirect.com.
Lewendon, Ann et al., Structural and Mechanistic Studies of Galactoside Acetyltransferase, the *Escherichia coli* LacA Gene Product, The Journal of Biological Chemistry, 1995, vol. 270, No. 44, Issue of Nov. 3, p. 26326-26331, particularly p. 25326.
Zhou, Shengde et al., Gene Integration and Expression and Extracellular Secretion of *Erwinia chrysanthemi* Endoglucanase CelY (celY) and CelZ (celZ) in Ethanolo-genic *Klebsiella oxytoca* P2, Applied and Environmental Microbiology, Jan. 2001, vol. 67, No. 1, p. 6-14. abstract.
Kim, Insook, et al., Ribose Utilization with an Excess of Mutarotase Causes Cell Death Due to Accumulation of Methylglyoxal, Journal of Bacteriology, Nov. 2004, v. 186, n. 21, p. 7229-7235.
Hornsten E.G., et al., On culturing *Escherichia coli* on a mineral salts medium during anaerobic conditions, Bioprocess Engineering 12 (1995), v. 12, p. 157-162.
Underwood S.A., t al., Lack of Protective Osmolytes Limits Final Cell Density and Volumetric Productivity of Ethanologenic *Escherichia coli* KOI 1during Xylose Fermentation, Applied and Environmental Microbiology, May 2004, v. 70, n. 5, p. 2734-2740, abstract.

(Continued)

Primary Examiner — Anand Desai
(74) Attorney, Agent, or Firm — Edwards Wildman Palmer LLP; Peter F. Corless; Jeffrey D. Hsi

(57) ABSTRACT

The invention provides recombinant bacteria, which comprise a full complement of heterologous ethanol production genes. Expression of the full complement of heterologous ethanol production genes causes the recombinant bacteria to produce ethanol as the primary fermentation product when grown in mineral salts medium, without the addition of complex nutrients. Methods for producing the recombinant bacteria and methods for producing ethanol using the recombinant bacteria are also disclosed.

55 Claims, 25 Drawing Sheets

(56) References Cited

OTHER PUBLICATIONS

First Office Action received from Chinese Patent Office for corresponding Chinese Patent Application No. 200780037561.7, Issued Jul. 7, 2011.

Notification of Examination received from Eurasian Patent Office for corresponding Eurasian Patent Application No. 200900286/28.

* cited by examiner

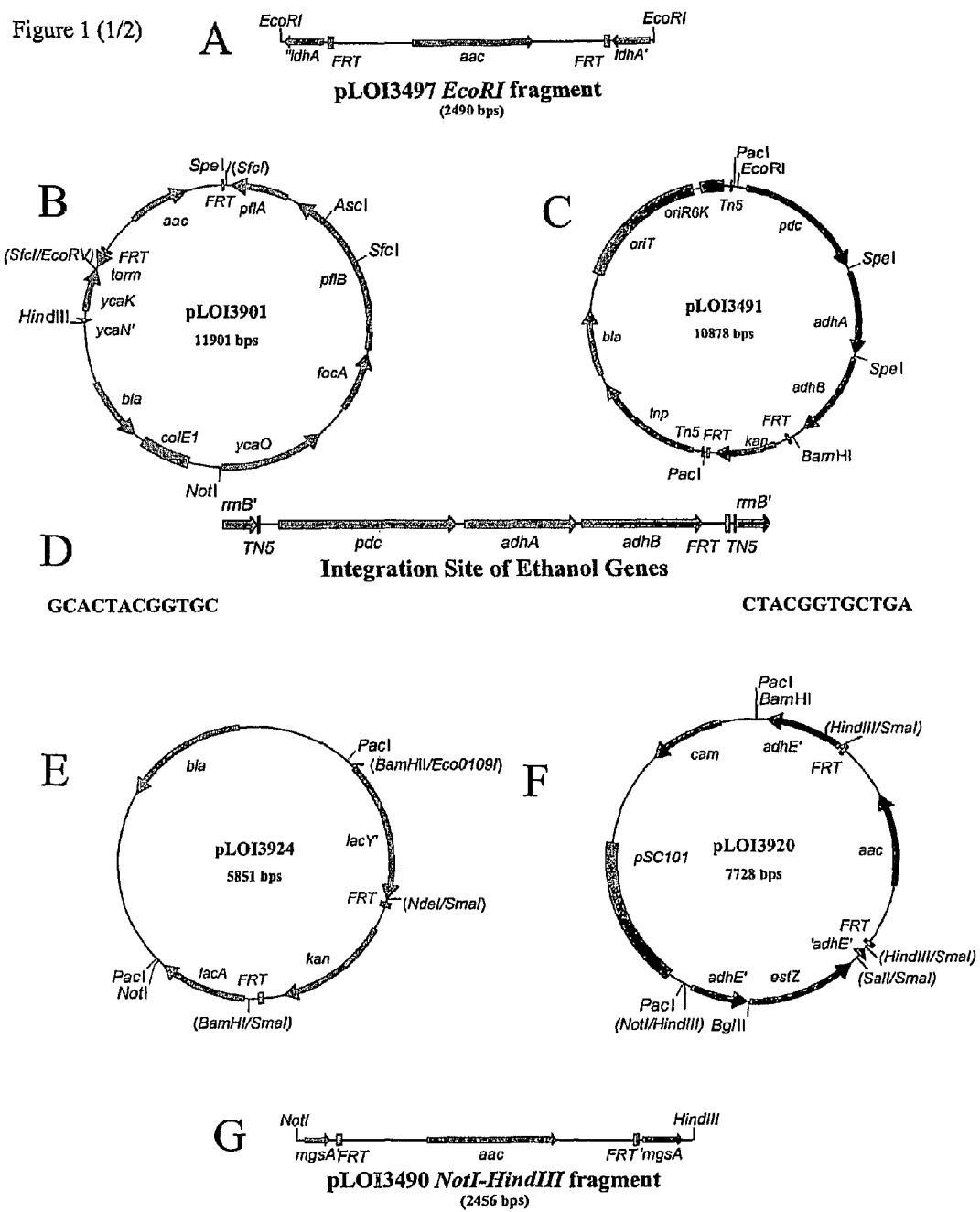
Figure 1 (1/2)

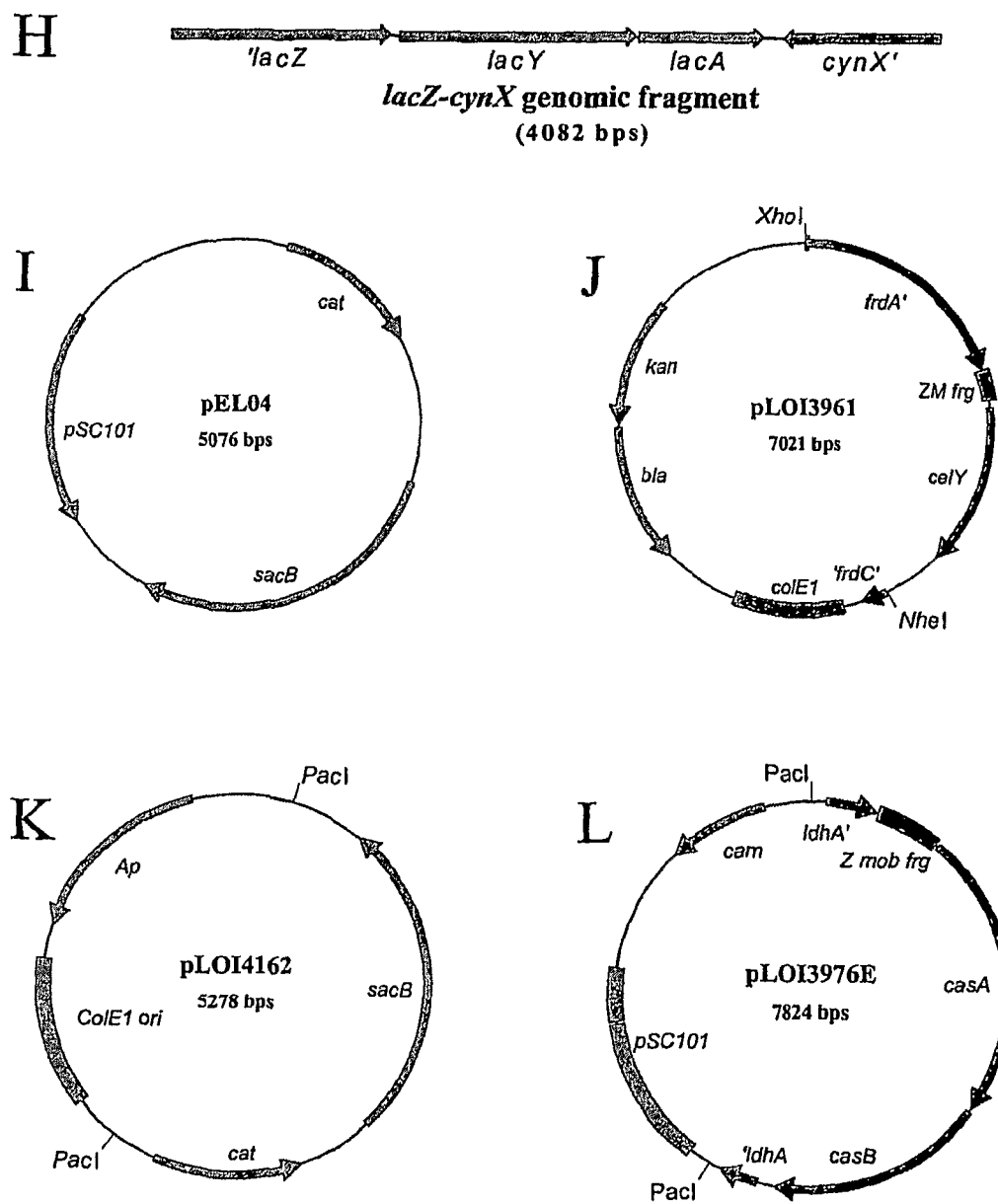
Figure 1(2/2)

Figure 9
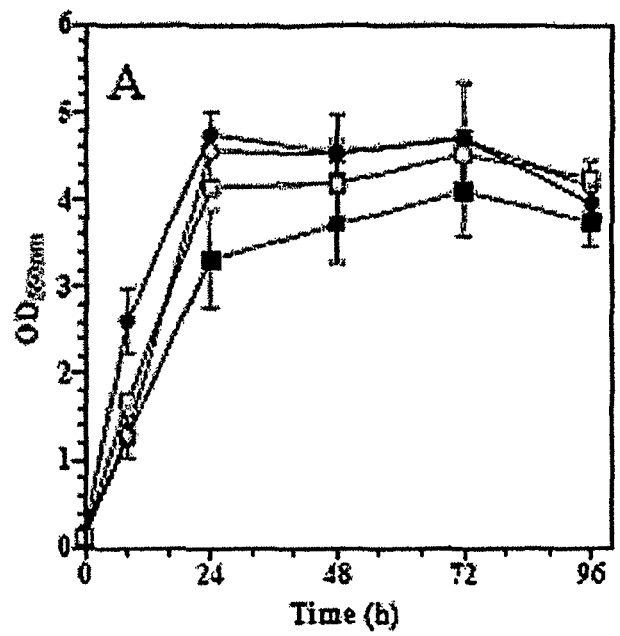
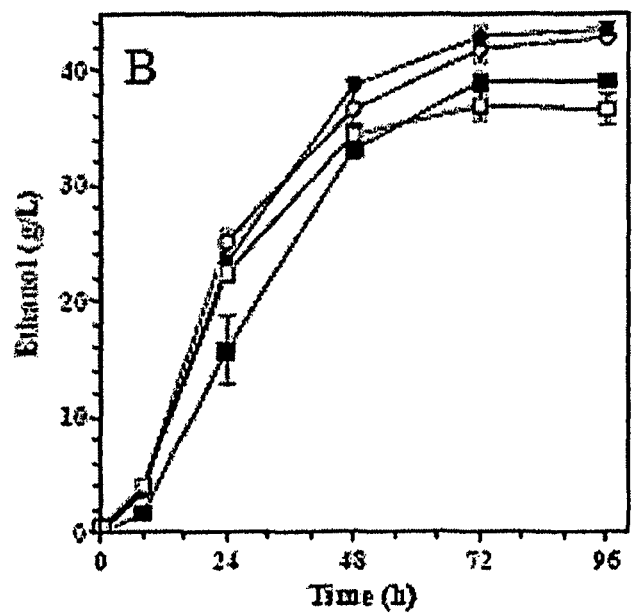

Figure 10
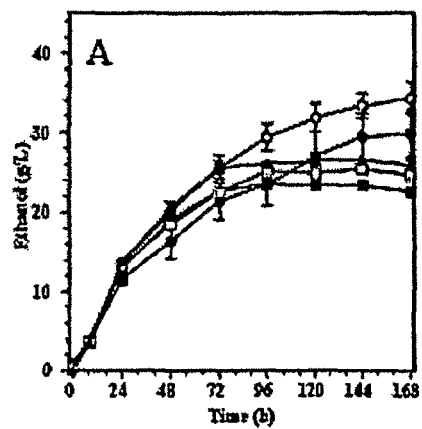
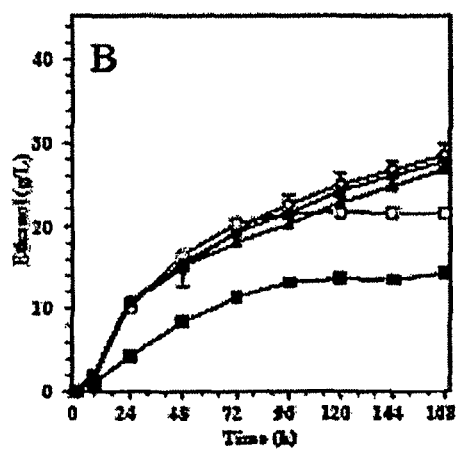
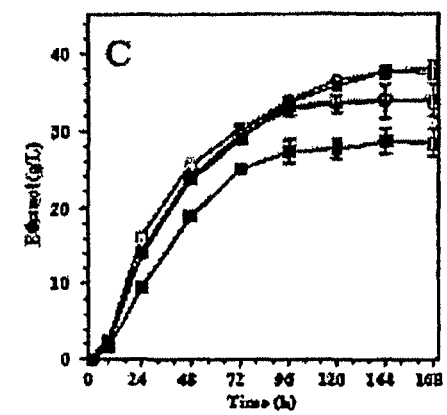

RE-ENGINEERING BACTERIA FOR ETHANOL PRODUCTION

RELATED APPLICATIONS

This application is the U.S. national phase, pursuant to 35 U.S.C. §371, of PCT international application Ser. No. PCT/US2007/017646, filed Aug. 8, 2007, designating the United States and published in English on Feb. 21, 2008 as publication WO 2008/021141 A2, which claims the benefit of U.S. Provisional Application Ser. No. 60/836,726, filed Aug. 9, 2006. The entire contents of the aforementioned patent applications are expressly incorporated herein by this reference.

GOVERNMENT SPONSORED RESEARCH

Funding for the present invention was provided in part by the Government of the United States under Grant Nos.: 01-35504-10669 and 00-52104-9704 from the U.S. Department of Agriculture, and FG02-96ER20222 from the U.S. Department of Energy. The Government of the United States has certain rights in and to the invention.

BACKGROUND OF THE INVENTION

Lignocellulosic biomass represents a renewable source of carbohydrate for biological conversion into fuels and chemicals and, as such, presents an attractive alternative to petroleum-based technology (Arntzen and Dale, 1999). It is recognized, however, that to reach its full potential, commodity production of ethanol from biomass will require high rates and efficiencies, simple processes, and inexpensive media (Ingram et al. 1998; Zhang & Greasham 1999).

Bacteria such as *Escherichia coli* have the native ability to metabolize all sugar constituents contained in lignocellulose. Early on, the qualities of environmental hardiness, broad substrate range, and ability to grow well in mineral salts media were recognized as important criteria that led to the selection of *E. coli* as a platform organism for metabolic engineering (Alterthum & Ingram 1989; Zhou et al. 2006a). Strain KO11 (ATCC 55124). Thus *E. coli* was engineered for ethanol production by integrating two *Zymomonas mobilis* genes (pdc, adhB) behind the pflB promoter of *E. coli* (Ohta et al. 1991). Despite the prototrophic nature of the *E. coli* strains, however, complex and costly nutrients were needed to rapidly and efficiently produce high ethanol titers using the KO11 strain (Asghari, et al. 1996; Martinez et al. 1999; Underwood et al. 2004; York & Ingram 1996).

To date, efforts to develop improved media and genetic modifications have been generally unsuccessful in eliminating the requirement for complex and costly nutrients, although betaine was found to be helpful (Underwood et al. 2004). Recently *E. coli* strain KO11 has been re-engineered to rapidly and efficiently ferment sugars to D (−)-lactate at high yields in mineral salts media (Zhou et al. 2006a and 2006b). However, to fully realize the potential of recombinant ethanologenic bacterial strains to serve as a source of ethanol, there is a need for new and improved strains of such bacteria that can efficiently produce ethanol while growing in inexpensive mineral media.

SUMMARY OF THE INVENTION

The present invention is based, at least in part, on the discovery of a new strategy for metabolic engineering of bacteria for ethanol production. In particular, the invention provides engineering strategies that overcome low ethanol yield and complex media requirements previously limiting to the engineering of bacteria for the production of ethanol in mineral salts medium.

Prior art recombinant ethanologenic bacteria require complex nutrients to rapidly and efficiently produce high ethanol titers. *E. coli* strain KO11 (ATCC 55124) is exemplary of such prior art recombinant bacteria. Strain KO11 was engineered for ethanol production by integrating two *Zymomonas mobilis* genes (pdc, adhB) behind the pflB promoter of *E. coli* (Ohta et al. 1991). Despite the prototrophic nature and its native ability to metabolize all sugar constituents in lignocellulose, complex nutrients were, however, needed to rapidly and efficiently produce high ethanol titers using the strain KO11 (Asghari, et al. 1996; Martinez et al. 1999; Underwood et al. 2004; York & Ingram 1996).

Without being bound by theory, the inventors have identified four factors which can contribute to the limited performance of recombinant organisms such as KO11 in mineral salts media: (1) the arbitrary selection of pflB as the site of integration in KO11 of the *Zymomonas mobilis* alcohol production genes; (2) the incomplete set of alcohol production genes from *Zymomonas mobilis*; (3) the presence of an antibiotic resistance gene; and (4) the presence of one or more genes that code for enzymes involved in alternative and/or competing metabolic pathways that interfere with or otherwise reduce the amount of ethanol produced.

The inventors have addressed these four factors. Consequently, the instant invention provides a recombinant bacterium, which is capable of growth and fermentation in mineral salts medium and which rapidly and efficiently produces ethanol in high titers.

Accordingly, in one aspect, the invention provides a recombinant bacterium which comprises a full complement of heterologous ethanol production genes.

In another aspect, the invention provides a recombinant bacterium which comprises a full complement of heterologous ethanol production genes, wherein the full complement of heterologous ethanol production genes is integrated into a ribosomal RNA operon.

In a further aspect, the invention provides a recombinant bacterium which comprises a full complement of heterologous ethanol production genes, wherein one or more antibiotic markers are removed.

In another further aspect, the invention provides a recombinant bacterium which comprises a full complement of heterologous ethanol production genes, wherein one or more genes encoding polypeptides that interfere with or otherwise reduce the amount of ethanol produced by the full complement of heterologous ethanol production genes are inactivated.

In a further aspect, the invention provides a recombinant bacterium which comprises a full complement of heterologous ethanol production genes and one or more genes that encode polypeptides that facilitate production of ethanol or otherwise increase the amount of ethanol produced by the full complement of heterologous ethanol production genes.

In an embodiment of each of the aforementioned aspects of the invention, expression of the full complement of heterologous ethanol production genes causes the recombinant bacterium to produce ethanol as the primary fermentation product. In one embodiment of the recombinant bacterium which comprises a full complement of heterologous ethanol production genes, the one or more genes are heterologous genes.

In another aspect, the invention provides a recombinant bacterium which comprises a full complement of heterologous ethanol production genes that are integrated into a ribosomal RNA operon, wherein expression of the full complement of heterologous ethanol production genes causes the recombinant bacterium to produce ethanol as the primary fermentation product, and one or more genes that encode polypeptides that facilitate production of ethanol or otherwise increase the amount of ethanol produced by the full complement of heterologous ethanol production genes, and wherein the recombinant bacterium does not contain an antibiotic resistance marker, and one or more genes encoding polypeptides that interfere with or otherwise reduce the amount of ethanol produced by the full complement of heterologous ethanol production genes are inactivated.

In certain embodiments, the ribosomal RNA operon comprises a gene selected from the group consisting of rrl A, rrlE, rrlC, rrlD, rrlE, rrlG and rrlnH. In a particular embodiment, the ribosomal RNA operon comprises the rrlE gene.

In another particular embodiment, the invention features the recombinant bacterium of any of the aspects of the invention, wherein the full complement of heterologous ethanol production genes comprises pdc, adhA and adhB. In a specific embodiment, the full complement of heterologous ethanol production genes is derived from *Zymomonas mobilis*.

In another embodiment, the recombinant bacterium has had an antibiotic resistance marker removed. In specific examples, the antibiotic resistance marker that is removed from the recombinant bacterium is selected from the group consisting of apramycin, kanamycin, tetracycline, ampicillin, and chloramphenicol.

In one embodiment, one or more genes that are inactivated in the recombinant bacterium of the invention encode proteins involved in fermentative routes for NADH oxidation. In a particular embodiment, the one or more genes that are inactivated are endogenous to the bacterium. In another particular embodiment, the one or more genes that are inactivated are heterologous to the bacterium.

In one embodiment of the invention, the one or more genes that are inactivated are selected from the group consisting of the genes comprising the focA-pflB gene region, ldhA, ackA, adhE, frd operon, casAB and mgsA. In a particular embodiment, the ackA, adhE, ldh genes and the frd operon encode proteins that are involved in alternate pathways for pyruvate metabolism. In one embodiment, the focA-pflB gene region, ldhA, ackA, adhE, genes comprising the frd operon and mgsA are endogenous genes. In another embodiment, the casAB genes are heterologous genes. In one embodiment, an ldhA gene is deleted. In another embodiment, the ldhA gene is an endogenous gene.

In a further embodiment, the recombinant bacteria of the invention further comprise a focA-pflB gene region. In one embodiment, the focA-pflB gene region is an endogenous gene region. In another embodiment, the focA-pflB gene region is from *Escherichia coli*.

The focA-pflB gene region was initially deleted to block the production of excess formate and acetyl-coA, which would reduce yield by consuming two NADH per ethanol using acetyl-coA as a substrate.

In yet another embodiment of the invention, the gene that encodes a polypeptide that facilitates production of ethanol or otherwise increases the amount of ethanol produced by the full complement of heterologous ethanol production genes comprises an estZ gene. In one embodiment, the estZ gene is a heterologous gene. In another embodiment, the estZ gene is from *Pseudomonas putida*.

The est gene helps to reduce the production of a very minor unwanted side product, ethyl acetate. Ethyl acetate separation from ethanol during final purification adds cost to the process. Yield changes are insignificant, but cost of purification can be significant.

In another embodiment of the invention, the one or more genes that encode polypeptides that facilitate production of ethanol or otherwise increase the amount of ethanol produced by the full complement of heterologous ethanol production genes comprise lacA and lacY genes. In a particular embodiment, the lacA and lacY genes are endogenous genes. In another embodiment, the lacA and lacY genes are from *Escherichia coli*. In another particular embodiment of the invention, an mgsA gene is deleted. In one embodiment, the mgsA gene is an endogenous gene.

In another embodiment of the invention, the one or more genes that encode polypeptides that facilitate production of ethanol or otherwise increase the amount of ethanol produced by the full complement of heterologous ethanol production genes comprise a celY gene. In a particular embodiment, the celY gene is a heterologous gene. In another particular embodiment, the celY gene is from *Erwinia chrysanthemi*.

In accordance with various aspects of the invention, the recombinant bacterium produces ethanol as the primary fermentation product under anaerobic conditions. The recombinant bacterium is also capable of growth in mineral salts medium. In a particular embodiment, the mineral salts medium contains xylose. In another embodiment, the medium comprises at least about 7% xylose. In still another embodiment, the medium contains betaine. In one embodiment, the ethanol produced by the recombinant bacterium comprises greater than 40% of total non-gaseous fermentation products under anaerobic conditions in mineral salts medium.

In accordance with various aspects of the invention, the recombinant bacterium is derived from a bacterium that is Gram-positive or Gram-negative. In one embodiment, the bacterium is a Gram-negative bacterium selected from the group consisting of *Acinetobacter, Gluconobacter, Escherichia, Geobacter, Shewanella, Salmonella, Shigella, Eneterobacter, Citrobacter, Erwinia, Serratia, Proteus, Hafnia, Yersinia, Morganella, Edwardsiella*, and *Klebsiella*. In a particular embodiment, the bacterium is *Escherichia coli*. In another particular embodiment, the bacterium is *Klebsiella oxytoca*.

In another embodiment, the bacterium is a Gram-positive bacterium selected from the group consisting of *Bacillus, Clostridium, Corynebacterium, Geobacillis, Lactobacillis, Lactococcus, Oenococcus, Streptococcus* and *Eubacterium*. In one embodiment, the recombinant bacterium is derived from *Escherichia coli* strain KO11 (ATCC55124). In another embodiment, the recombinant bacterium is derived from *E. coli* strain SZ110 (NRRL B-30951). In a particular embodiment, the recombinant bacterium is *E. coli* strain LY165 (NRRL B-30952). In another particular embodiment, the recombinant bacterium is *E. coli* strain LY168 (NRRL B-30953).

In related aspects, the invention provides the following novel recombinant organisms: *E. coli* strain SZ110 (NRRL B-30951); *E. coli* strain LY165 (NRRL B-30952); and *E. coli* strain LY168 (NRRL B-30953); *E. coli* strain BW34.

In other related aspects, the invention provides the recombinant *E. coli* strains: LY149, LY151, LY158, LY159, LY160, LY160im, LY161, LY163, LY168im, LY169, LY170, LY172, LY172im, LY173, LY178, LY180, LY186, BW34-XZ106, BW34-XZ107, BW34-XZ108, BW34-XZ109, BW34-XZ110, BW34-XZ111, BW34-XZ112, BW34-XZ113, BW34-XZ114, BW34-XZ115, BW34-XZ116, BW34-XZ117, BW34-XZ118, BW34-XZ119, BW34-XZ120, BW34-XZ121, BW34-XZ122, BW34-XZ123, and BW34-XZ124.

Another aspect of the invention features a method for producing recombinant bacteria of the invention as described herein. The method comprises the step of integrating a full complement of heterologous ethanol production genes into a host bacterium, thereby producing a recombinant bacterium that comprises a full complement of heterologous ethanol production genes.

In one embodiment, the method features integrating the full complement of heterologous ethanol production genes into a ribosomal RNA (rRNA) operon. In a particular embodiment, the RNA operon comprises a gene selected from the group consisting of rrl A, rrlE, rrlC, rrlD, rrlE, rrlG and rrlH. In still another particular embodiment, the ribosomal RNA operon comprises the rrlE gene.

Another embodiment of the invention features recombinant bacterium as described herein, that does not contain an antibiotic resistance marker. In one embodiment, the methods further provide the step of removing one or more antibiotic markers.

In yet another embodiment, the method features inactivating one or more genes encoding polypeptides that interfere with or otherwise reduce the amount of ethanol produced by the full complement of ethanol production genes. In still a further embodiment, the method features integrating one or more heterologous genes that encode polypeptides that facilitate production of ethanol or otherwise increase the amount of ethanol produced by the full complement of heterologous ethanol production genes.

In another embodiment, the method further comprises the steps of integrating the full complement of heterologous ethanol production genes within the rrlE gene of the host bacterium, removing one or more antibiotic markers, and inactivating one or more genes encoding polypeptides that interfere with or otherwise reduce the amount of ethanol produced by the full complement of ethanol production genes not required for ethanol production.

In a particular embodiment of the method, the full complement of heterologous ethanol production genes that is integrated comprises pdc, adhA and adhB. In a further embodiment of the method, the pdc, adhA and adhB genes are derived from *Zymomonas mobilis*. In another embodiment, the full complement of ethanol production genes are contained in a promoterless operon. In a further embodiment, the promoterless operon contains the adhA gene ligated in to the SpeI site between pdc and adhB. In yet another embodiment, the promoterless operon contains a removable antibiotic marker. In still another embodiment, the promoterless operon is integrated using a Tn5 transposon. In one embodiment of the method, the antibiotic marker is removed with recombinase. In another embodiment, the antibiotic marker is selected from the group consisting of apramycin, kanamycin, tetracycline, ampicillin and chloramphenicol.

In another embodiment of the method, the one or more genes are inactivated by deletion or mutation. In a particular embodiment, one or more ethanol production genes are inactivated by deletion. In another embodiment, genes encoding proteins involved in alternative routes of pyruvate metabolism are inactivated. In a further embodiment, the genes of any of the aspects of the invention are inactivated before the full complement of heterologous ethanol production genes is integrated.

In one embodiment of the method, the host bacterium is *E. coli* strain KO11 (ATCC55124). In a particular embodiment, the recombinant bacterium is derived from SZ110 (NRRL B-30951).

In another embodiment of the method, genes comprising the focA-pflB gene region are inactivated by deletion. In another particular embodiment, the genes encoding proteins involved in alternate pathways for pyruvate metabolism are deleted. In one embodiment, the genes include ackA, adhE, ldhA and mgsA. In another embodiment, the endogenous ldhA gene is inactivated by deletion. In another embodiment, the ldhA gene is deleted before the full complement of heterologous ethanol production genes is integrated. In a further embodiment, the heterologous casAB genes are inactivated by deletion. In another embodiment, the casAB genes are from *Klebsiella oxytoca*. In another particular embodiment, the method further comprises the step of replacing the casAB genes with lacA and lacY genes. In particular embodiments, the lacA and lacY genes are from *E. coli*. In another particular embodiment, the method further comprises the step of integrating an estZ gene. In a particular embodiment, the estZ gene is from *Pseudomonas putida*. In one embodiment, the estZ gene is integrated after integration of the full complement of ethanol production genes. In another particular embodiment of the method, an endogenous mgsA gene is inactivated by deletion.

In one embodiment, the lac operon is removed or inactivated. In another embodiment of the method, the lac operon is restored. In a further embodiment, the genes restored from the lac operon comprise lacA, lacY and lacZ. In another embodiment, the genes comprising the lac operon are from *E. coli*. In another particular embodiment of the method, the frdB gene is deleted. In another embodiment, the celY gene is integrated. In one related embodiment, the celY gene is from *E. chrysanthemi*.

In another embodiment of the method, the casAB genes are integrated. In a further embodiment, the casAB genes are integrated into the ldhA gene. In another embodiment, the casAB genes are from *Klebsiella oxytoca*.

In another embodiment, the method further comprises restoring the function of the focA-pflB gene region. In a particular embodiment, the function of the focA-pflB gene region is restored by homologous recombination of the focA-pflB gene region. In another particular embodiment, the function of the focA-pflB gene region is restored before integration of the full complement of ethanol production genes.

In one embodiment of the method, the host bacterium is *E. coli* strain SZ110 (NRRL B-30951). In another embodiment, the recombinant bacterium is *E. coli* strain LY165 (NRRL B-30952). In still another embodiment, the recombinant bacterium is *E. coli* strain LY168 (NRRL B-30953). In a related embodiment, the recombinant bacterium is capable of growth in mineral salts medium. In a particular embodiment, the mineral salts medium comprises xylose.

In one embodiment of the foregoing methods of the invention, expression of the full complement of heterologous ethanol production genes causes the recombinant bacterium to produce ethanol as the primary fermentation product.

Another aspect of the invention features a method for producing ethanol from an oligosaccharide source, comprising contacting the oligosaccharide with the recombinant bacterium of the invention as hereinabove described under conditions appropriate for ethanol production, thereby producing ethanol from an oligosaccharide source. In a particular embodiment of the method, the oligosaccharide is selected from the group consisting of lignocellulose, hemicellulose, cellulose, and pectin or a combination thereof. In another embodiment of the method, the ethanol produced comprises greater than 40% of total non-gaseous fermentation products. In one embodiment, the method further comprises providing the recombinant bacterium of the invention. In another embodiment, the invention further comprises obtaining the recombinant bacterium of the invention.

Another embodiment of the invention further comprises contacting the oligosaccharide with the recombinant bacterium in mineral salts medium. In one embodiment, the mineral salts medium comprises per liter: 3.5 g $KH_2PO_4$, 5.0 g $K_2HPO_4$, 3.5 g $(NH_4)_2HPO_4$, 0.25 g $MgSO_4 \cdot 7 H_2O$, 15 mg $CaCl_2 \cdot 2 H_2O$, 0.5 mg of thiamine, and 1 mL of trace metal stock, supplemented with 2(w/v) % to 9 (w/v) % xylose. In another particular embodiment, betaine is added to the mineral salts medium. In another embodiment, MOPS is added to the mineral salts medium.

In another embodiment, the mineral salts medium AM1 medium contains (per liter): 2.63 g $(NH_4)_2HPO_4$, 0.87 g $NH_4H_2PO_4$, 0.375 g/L $MgSO_4 \cdot 7H_2O$, 0.149 g KCl, 0.0163 g Betaine HCl (pH 7.4), and 1.5 mL of trace metal stock, supplemented with 2 (w/v) % to 14 (w/v) % sugar. In a further embodiment, the AM1 medium contains xylose. In another embodiment, the AM1 medium comprises at least about 9% xylose. In still a further embodiment, trace metal stock can be prepared in 0.1M HCl (per liter: 1.6 g $FeCl_3 \cdot 6H_2O$, 0.2 g $CoCl_2 \cdot 6H_2O$, 0.1 g $CuCl_2 \cdot 2H_2O$, 0.2 g $ZnCl_2$, 0.2 g $Na_2MoO_4 \cdot 2H_2O$, 0.05 g $H_3BO_3$, 0.33 g $MnCl_2 \cdot 4H_2O$).

In one embodiment of the foregoing methods for producing ethanol from an oligosaccharide source, expression of the full complement of heterologous ethanol production genes causes the recombinant bacterium to produce ethanol as the primary fermentation product.

A further aspect of the invention provides a recombinant bacterium which comprises a full complement of heterologous ethanol production genes, wherein the recombinant bacterium is prepared by a process comprising the steps of any one of the steps of the method of the invention as described hereinabove. In one embodiment, expression of the full complement of heterologous ethanol production genes causes the recombinant bacterium to produce ethanol as the primary fermentation product.

Another aspect of the invention provides a kit comprising the recombinant bacterium of the invention as hereinabove described and instructions for use. In one embodiment, the instructions for use are in accordance with any of the methods of the invention for producing ethanol from an oligosaccharide source. In another embodiment, the kit further comprises a sugar source. In yet another embodiment, expression of the full complement of heterologous ethanol production genes causes the recombinant bacterium to produce ethanol as the primary fermentation product.

BRIEF DESCRIPTION OF THE DRAWINGS

FIG. 1 (A-L) schematically illustrates plasmids and DNA fragments used in strain construction in accordance with the invention. Plasmids pLOI3497, pLOI3901 and pLOI3491 are shown in panels A-C, respectively. Ethanol genes (pdc, adhA, adhB) and the site of integration are shown in panel D. Plasmids pLOI3924 and pLOI3920 are shown in panels E and F, respectively. A 2456 bps pLOI3940 fragment is shown in panel G. A 4,082 bps genomic PCR fragment is shown in panel H. Plasmids pEL04, pLOI3961, pLOI4162 and pLOI3976E are shown in panels I through L, respectively.

FIG. 9 (A and B) are graphs demonstrating growth (A) and ethanol production (B) from 90 g/L glucose in OUM1 by K. oxytoca strains BW21 (○), BW34 (●), BW35 (■), and BW35 pCPP2006 (□).

FIG. 10 (A-C) are graphs demonstrating ethanol production in SSF of 100 g/L Sigmacell using (A) 50 µl Spezyme GC220 per g cellulose; (B) 50 µl Spezyme CE per g cellulose; and (C) 100 50 µl Spezyme CE per g cellulose by ethanologenic *K. oxytoca* strains P2 (■); SZ22 (□); BW21 (●), BW34 (○), and BW35 pCPP2006 ▲.

DETAILED DESCRIPTION OF THE INVENTION

Figure 2:
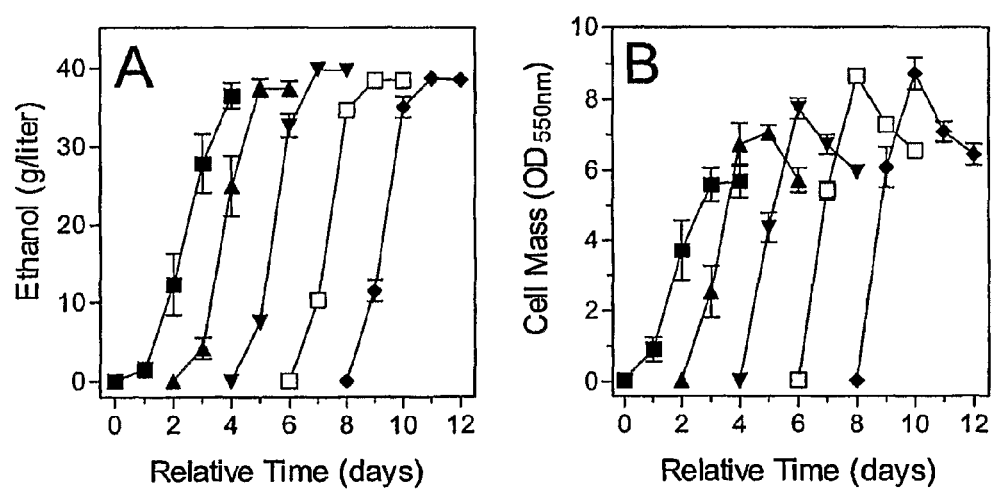
FIGS. 2 (A and B) are graphs demonstrating growth-based selection for strain improvement. A population of LY151 harboring random Tn5-based insertions (Z. mobilis pdc-adhA-adhB-FRT-kan-FRT) was serially transferred 38 times in NBS mineral salts medium (9% xylose) as a growth-based selection for ethanol productivity. Strains LY158 and LY159 were isolated from the final transfer. Transfers were grouped and averaged: (■), transfers 1-9 (48 h intervals, inoculum of 16 mg dcw $l^{-1}$); (▲), transfers 10-14 (48-h intervals, 1 mM betaine, inoculum of 16 mg dcw $l^{-1}$); (▼), transfers 15-24 (24-h intervals, 1 mM betaine, inoculum of 10 mg dcw $l^{-1}$); (□), transfers 24-34 (24-h intervals, 1 mM betaine, inoculum of 10 mg dcw $l^{-1}$); (♦), transfers 35-38 (24-h intervals, 1 mM betaine, inoculum of 10 mg dcw $l^{-1}$; Panel A. Y-axis indicates ethanol produced (g/liter). Panel B. Y-axis indicates cell mass.

In order for the full scope of the invention to be clearly understood, the following definitions are provided.

I. Definitions

The terms "host" and "host bacterium" are used interchangeably and are intended to include a bacterium, e.g., a naturally occurring bacterium or a recombinant bacterium, which serves as a host cell from which a recombinant bacterium of the invention is produced. Hence the recombinant bacterium of the invention is said to be "derived from" the host bacterium.

The term "derived from" as in "polynucleotide or gene derived from a bacterium" is intended to include the isolation (in whole or in part) of a polynucleotide segment from the indicated source (i.e., the bacterium) or the purification of a polypeptide from an indicated source (i.e., the bacterium). In this regard, the term is intended to include, for example, direct cloning, PCR amplification, or artificial synthesis from, or based on, a sequence associated with the indicated polynucleotide source.

As used herein the terms "recombinant bacterium," "recombinant host cell," "recombinant microorganism," and the like, are intended to include cells suitable for, or subjected to, genetic manipulation, or to incorporate heterologous polynucleotide sequences by transfection. The cell can be a microorganism or a higher eukaryotic cell. The term is intended to include progeny of the host cell originally transfected. In some embodiments, the host cell is a bacterial cell, e.g., a Gram-positive bacterial cell or a Gram-negative bacterial cell. Gram-positive bacterial host cells include, e.g., *Bacillus, Clostridium, Zymomonas, Corynebacterium, Geobacillis, Lactobacillis, Lactococcus, Oenococcus, Streptococcus* and *Eubacterium*. Gram-negative bacterial host cells include all facultatively anaerobic Gram-negative cells of the family Enterobacteriaceae such as *Escherichia, Shigella, Citrobacter, Salmonella, Klebsiella, Enterobacter, Erwinia, Kluyvera, Serratia, Cedecea, Morganella, Hafnia, Edwardsiella, Providencia, Proteus,* and *Yersinia*. Preferred recombinant hosts are *Escherichia coli* and *Klebsiella oxytoca* cells.

A "gene," as used herein, is a nucleic acid that can direct synthesis of an enzyme or other polypeptide molecule, e.g., can comprise coding sequences, for example, a contiguous open reading frame (ORF) that encodes a polypeptide, or can itself be functional in the organism. A gene in an organism can be clustered in an operon, as defined herein, wherein the operon is separated from other genes and/or operons by intergenic DNA. Individual genes contained within an operon can overlap without intergenic DNA between the individual genes. In addition, the term "gene" is intended to include a specific gene for a selected purpose. A gene can be endogenous to the host cell or can be recombinantly introduced into the host cell, e.g., as a plasmid maintained episomally or a plasmid (or fragment thereof) that is stably integrated into the genome. A heterologous gene is a gene that is introduced into a cell and is not native to the cell. In accordance with the invention, a heterologous gene also includes an endogenous gene that is introduced into the cell at a location other than its natural location in the genome of the cell.

The term "heterologous ethanol production gene" is intended to include a gene or portion thereof that is derived from any source, e.g., eukaryotes, prokaryotes, archaea, virii, or synthetic nucleic acid fragments, that encodes a polypeptide involved in the production of ethanol as a primary fermentation production, and that is incorporated into a host cell to which the gene is not native. The term "heterologous ethanol fermentation gene" also refers to a gene that encodes a polypeptide involved in the fermentation of a carbohydrate, for example in a metabolic pathway of an organism that produces ethanol as the primary fermentation produced by an organism, that is not naturally occurring in an organism, e.g., a gene that is introduced into the organism. The terms "heterologous ethanol production gene" and "heterologous ethanol fermentation gene" may be used interchangeably and are intended to include a gene that is involved in at least one step in the bioconversion of a carbohydrate to ethanol. Accordingly, the term is intended to include any gene encoding a polypeptide such as an alcohol dehydrogenase, a pyruvate decarboxylase, a secretory protein/s, or a polysaccharase e.g., a glucanase, such as an endoglucanase or exoglucanase, a cellobiohydrolase, β-glucosidase, endo-1, 4-β-xylanase, β-xylosidase, α-glucuronidase, α-L-arabinofuranosidase, acetylesterase, acetylxylanesterase, α-amylase, β-amylase, glucoamylase, pullulanase, β-glucanase, hemicellulase, arabinosidase, mannanase, pectin hydrolase, or pectate lyase.

The phrase "full complement of heterologous ethanol production genes" is meant to include substantially all the genes that have evolved in an ethanologenic organism, from which the heterologous ethanol production genes are obtained/derived, that comprise the organism's natural ethanol production pathway. A full complement of ethanol production genes includes substantially all the genes of an ethanologenic organism that direct fermentation away from metabolic pathways involving enzymes that do not produce ethanol as the primary fermentation product ("alternate metabolic pathways"). Such alternate metabolic pathways include alternate pathways for pyruvate metabolism and fermentative pathways for NADH oxidation. For example, the full complement of heterologous ethanol production genes of *Zymomonas mobilis*, an ethanologenic bacterium, includes the pdc, adhA and adhB genes. The full complement of heterologous ethanol production genes of *Saccharomyces cerevisiae*, an ethanologenic yeast, includes four or five different adh genes, for example alcohol dehydrogenase I, II, III and IV (adh I-IV) (Drewke et al. 1988; Reid et al. 1994), and 2 different pdc genes. In accordance with an embodiment of the invention, the recombinant *E. coli* KO11 (ATCC 55124) (Ohta et al. 1991) can be used as a host cell. KO11 contains a *Z. mobilis* cassette encoding the pdc and adhB genes only and, therefore, does not have a full complement of heterologous ethanol production genes in accordance with the invention. In contrast, novel recombinant *E. coli* strains LY165 (NRRL B-30952) and LY168 (NRRL B-30953) of the invention, which are derived from KO11, contain a *Z. mobilis* cassette encoding the pdc, adhA and adhB genes and, therefore, have a full complement of heterologous ethanol production genes in accordance with the invention.

The phrase "alternate pathways for pyruvate metabolism" is intended to include a subset of fermentative pathways for NADH oxidation. The phrase is meant to include metabolic pathways involving enzymes that do not produce ethanol as the primary fermentation product. One example of such alternate pathways includes those pathways that produce lactate and succinate as the primary fermentation products. Other examples of such pathways are wasteful pathways. A wasteful pathway oxidizes two NADH molecules per ethanol, rather than one per ethanol, as in the preferred pathway of the instant invention, and thus reduces the final yield. Examples of wasteful alternate pathways for pyruvate metabolism include pathways involving enzymes such as alcohol dehydrogenase E (adhE) and acetate kinase (ackA). A further example of an alternate pathway for pyruvate metabolism includes the pathway encoded by the ldhA (lactate dehydrogenase) gene. LdhA encodes a one-enzyme pathway for the metabolism of NADH+ pyruvate to produce NAD+ and lactate. Yet another example of an alternate pathway for pyruvate metabolism includes pathways involving the genes that encode the four subunits of the fumarate reductase complex (the FRD operon) in addition to NADH and pyruvate that together oxidize NADH to NAD+ where the end product from pyruvate is succinate. The term alternative pathways for pyruvate metabolism, in certain embodiments, encompasses a subset of fermentative pathways for NADH oxidation.

The term "ribosomal RNA operon" is intended to mean the cluster of ribosomal RNA genes that are expressed as a group and their associated promoter and operator. There are seven ribosomal RNA (rRNA) operons, called rrlA, rrlB, rrlC, rrlD, rrlE, rrlG, and rrlH (Lindhal et al. 1986; Nomura et al., 1984). By convention, the term "rrlE" refers to one set of genes encoding all three ribosomal RNAs whereas the term "RRLE" refers to an rrlE gene product, i.e., a 23S, 16S, 5S rrlE ribosomal RNA molecule. An rrlE equivalent is present in most if not all organisms. An exemplary rrlE sequence is specified by GeneID number 948509. Each rRNA operon contains a 16S rRNA gene, a 23S rRNA gene, and a 5S rRNA gene, interspersed with various tRNA genes. The rrlD operon contains two 5S rRNA genes. "rrs" genes encode 16S rRNAs, "rrl" genes encode 23S rRNAs, and "rrf" genes encode 5S rRNAs.

The terms "inactivated" or "inactivate" are intended to include any means by which a gene is stopped from encoding its intended polypeptide or from encoding an active form of its intended polypeptide. Accordingly, the terms include, for example, mutation, deletion, insertion, duplication, missense, frameshift, repeat, nonsense mutation, or other alteration or modification such that gene activity (i.e. transcription) is blocked. For example, in accordance with one embodiment of the invention, one or more genes encoding polypeptides that interfere with or otherwise reduce the amount of ethanol produced by the full complement of heterologous ethanol production genes are inactivated by deletion.

The term "pyruvate decarboxylase" (pdc) is intended to include the enzyme that serves to direct the flow of pyruvate into ethanol during fermentation. By convention, the term "pdc" refers to a pyruvate decarboxylase gene whereas the term "PDC" refers to a pdc gene product, i.e., a pyruvate decarboxylase polypeptide or enzyme. An exemplary pdc sequence is the *Z. mobilis* pdc described by Conway et al. (J. Bacteriol. 169 (3), 949-954 (1987)) and set forth as GenBank accession number AAA27696.

The terms "alcohol dehydrogenase A" (adhA) and "alcohol dehydrogenase B" (adhB) and "alcohol dehydrogenase E" (adhE) are intended to include the enzymes that convert acetaldehyde to ethanol under fermentative conditions. By convention, the term "adhA," "adhB" or "adhE" refers to an alcohol dehydrogenase gene whereas the term "ADHA," "ADHB" or "ADHE" refers to an "adhA," "adhB" or "adhE" gene product, respectively, i.e., an alcohol dehydrogenase polypeptide or enzyme. An exemplary adhA sequence is the *Z. mobilis* adhA described by Keshav et al. (J. Bacteriol. 172 (5), 2491-2497 (1990)) and set forth as GenBank accession number AAA27682. An exemplary adhB sequence is the *Z. mobilis* adhB described by Conway et al. (J. Bacteriol. 169 (6), 2591-2597 (1987)) and set forth as GenBank accession number AAA27683. An exemplary adhE sequence is the *E. coli* adhE described by Kessler et al. (FEBS Lett. 281 (1-2), 59-63 (1991)) and set forth as GenBank accession number CAA41955.

The term "focA-pflB gene region" (focA-pflB gene region) is intended to include the focA, pflB genes involved in pyruvate metabolism. The term "pyruvate formate lyase" (pflB) is intended to include the enzyme that converts pyruvate to Acetyl-CoA and formate under fermentative conditions. By convention, the term "pflB" refers to a pyruvate formate lyase gene whereas the term "PFL" refers to a pfl gene product, i.e., a pyruvate formate lyase polypeptide or enzyme. An exemplary pflB sequence is the *E. coli* K-12 pflB described by Riley et al. (Nucleic Acids Res. 34 (1), 1-9 (2006)) and set forth as GenBank accession number NP_415423. The term "focA" (focA) is intended to include the enzyme involved in formate metabolism. An exemplary focA sequence is the *E. coli* K-12 focA described by Riley et al. (Nucleic Acids Res. 34 (1), 1-9 (2006)) and set forth as GenBank accession number NP_415424.

The term "lactate dehydrogenase" (ldhA) is intended to include the enzyme that converts pyruvate to lactate under fermentative conditions. By convention, the term "ldhA" refers to a lactate dehydrogenase gene whereas the term "LDHA" refers to an ldhA gene product, a lactate dehydrogenase polypeptide or enzyme. An exemplary ldhA sequence is the *E. coli* K-12 ldhA described by Riley et al. (Nucleic Acids Res. 34 (1), 1-9 (2006)) and set forth as GenBank accession number NP_415898.

The term "acetate kinase" (ackA) is intended to include the enzyme that encodes an alternative route for pyruvate metabolism. By convention, the term "ackA" refers to an acetate kinase gene whereas the term "ACKA" refers to an ackA gene product, i.e., an acetate kinase polypeptide or enzyme. An exemplary ackA sequence is the *E. coli* K-12 ackA described by Riley et al. (Nucleic Acids Res. 34 (1), 1-9 (2006)) and set forth as GenBank accession number NP_416799.

The term "frd operon" is intended to include the four subunits that comprise the fumarate reductase complex (A-D). By convention, the term "frd operon" refers to the genes which encode the four subunits, whereas the term "FRD OPERON" refers to the proteins which encode the four subunits. An exemplary fumarate reductase A sequence is the *E. coli* K-12 fumarate reductase A described by Riley et al. (Nucleic Acids Res. 34 (1), 1-9 (2006)) and set forth as GenBank accession number NP_418578. An exemplary fumarate reductase B sequence is the *E. coli* K-12 fumarate reductase B described by Riley et al. (Nucleic Acids Res. 34 (1), 1-9 (2006)) and set forth as GenBank accession number NP_418577. An exemplary fumarate reductase C sequence is the *E. coli* K-12 fumarate reductase C described by Blattner et al. (Nucleic Acids Res. 34 (1), 1-9 (2006)) and set forth as GenBank accession number NP 418576. An exemplary fumarate reductase D sequence is the *E. coli* K-12 fumarate reductase D described by Riley et al. (Nucleic Acids Res. 34 (1), 1-9 (2006)) and set forth as GenBank accession number NP_418575.

The term "cas AB" (casAB) is intended to include the enzymes Enzyme II cellobiose and phospho-beta-glucosidase that ferment cellubiose. By convention, the term "casAB" refers to the casAB genes whereas the term "CASAB" refers to the casAB gene product, i.e., a casAB enzyme. Exemplary casA and casB sequences are the *K. oxytoca* casA (cellobiose-specific PTS permease) described by Lai et al. (Appl. Environ. Microbiol. 63 (2), 355-363 (1997)) and set forth as GenBank accession number AAB51563 and the *K. oxytoca* casB (phospho-cellobiase) described by Lai et al (Appl. Environ. Microbiol. 63 (2), 355-363 (1997)) and set forth as GenBank accession number AAB51564. In certain embodiments, the casAB genes are from *Klebsiella oxytoca*.

The term "celY" (celY) is intended to include the enzyme endoglucanase Y. By convention, the term "celY" refers to the celY gene whereas the term "CELY" refers to the celY gene product, i.e., a celY enzyme. An exemplary celY sequence is the *E. chrysanthemi* celY (endoglucanase Y) described by Guiseppi et al. (Gene 106 (1), 109-114 (1991)) and set forth as GenBank accession number M74044.

The term "methylglyoxal synthaseA" (mgsA) is intended to include the enzyme that encodes the enzyme mgsA in the first step of the methylglyoxal bypass pathway. By convention, the term "mgsA" refers to a methylglyoxal synthase gene whereas the term "MGSA" refers to an mgsA gene product, i.e., a methylglyoxal synthaseA polypeptide or enzyme. An exemplary mgs sequence is the *E. coli* K-12 mgs described by Riley et al. (Nucleic Acids Res. 34 (1), 1-9 (2006)) and set forth as GenBank accession number NP_415483.

The term "short chain esterase" (estZ) is intended to include the enzyme that encodes a short chain esterase from *Pseudomonas putida* (NRRL B-18435). By convention, the term "estZ" refers to the short chain esterase gene whereas the term "ESTZ" refers to an estZ gene product, i.e., the short chain esterase polypeptide or enzyme. An exemplary estZ sequence is the *P. putida* estZ described by Hasona et al. (Appl. Environ. Microbiol. 68 (6), 2651-2659 (2002)) and set forth as GenBank accession number AAM16269.

The term "lac operon" is intended to include one regulatory gene (the i gene) and three structural genes (z, y, and a). By convention, the term "lac operon" refers to the genes, whereas the term "LAC OPERON" refers to the proteins which encode the four genes. The i gene codes for the repressor of the lac operon. The z gene codes for beta-galactosidase, the y gene codes for permease, and the a gene encodes a transacetylase.

The term "lacA" (lacA) is intended to include galactose transacetylase, an enzyme involved in lactose metabolism. By convention, the term "lacA" refers to a galactose transacetylase gene whereas the term "LACA" refers to a lacA gene product, i.e., a galactose transacetylase polypeptide or enzyme. An exemplary lacA sequence is the *E. coli* K-12 lacA described by Riley et al. (Nucleic Acids Res. 34 (1), 1-9 (2006)) and set forth as GenBank accession number NP_414876.

The term "lacY" (lacY) is intended to include permease, an enzyme involved in lactose metabolism. By convention, the term "lacY" refers to a permease gene whereas the term "LACY" refers to a lac Y gene product, i.e., a permease polypeptide or enzyme. An exemplary lacY sequence is the *E. coli* K-12 lacY described by Riley et al. (Nucleic Acids Res. 34 (1), 1-9 (2006)) and set forth as GenBank accession number NP_414877.

The term "chloramphenicol transacetylase" (cat) is intended to include the enzyme that causes antibiotic resistance to chloramphenicol. By convention, the term "cat" refers to a chloramphenicol transacetylase gene whereas the term "CAT" refers to a cat gene product, i.e., a chloramphenicol transacetylase polypeptide or enzyme. An exemplary cat sequence is the *S. enterica* lacY described by Parkhill et al. (Nature 413 (6858), 848-852 (2001)) and set forth as GenBank accession number NP_569406.

The terms "fermentation" and "fermenting" are intended to include the degradation or depolymerization of a complex sugar and bioconversion of that sugar residue into ethanol, lactate, acetate and succinate under anaerobic condition. The terms are intended to include the enzymatic process (e.g. cellular or acellular, e.g. a lysate or purified polypeptide mixture) by which ethanol is produced from a carbohydrate, in particular, as a primary product of fermentation.

The term "mineral salts medium" is intended to include a medium that contains a minimal amount of nutrients, e.g., one that consists essentially of mineral salts and other fundamental nutrients, but that enables a recombinant organism, e.g., a recombinant bacterium, of the invention to grow under anaerobic conditions and produce ethanol as the primary fermentation product without the need to add complex nutrients. For example, the novel *E. coli* LY165 recombinant bacterium of the invention will produce ethanol at a rate of about 44.9 g/L when grown in mineral salts medium in the absence of complex nutrients and the *E. coli* LY168 recombinant bacterium of the invention will produce ethanol at a rate of about 45.5 g/L when grown in mineral salts medium in the absence of complex nutrients. In contrast, KO11 produces ethanol at a rate of 26.9 g/L in mineral salts medium, and at a rate of 43.2 g/L only after the addition of complex nutrients. (See the examples below.)

The term "Gram-negative bacteria" is intended to include the art-recognized definition of this term. Exemplary Gram-negative bacteria include *Acinetobacter, Gluconobacter, Escherichia, Zymomonas, Geobacter, Shewanella, Salmonella, Shigella, Eneterobacter, Citrobacter, Erwinia, Serratia, Proteus, Hafnia, Yersinia, Morganella, Edwardsiella,* and *Klebsiella.*

The term "Gram-positive bacteria" is intended to include the art-recognized definition of this term. Exemplary Gram-positive bacteria include *Bacillus, Clostridium, Corynebacterium, Geobacillis, Lactobacillis, Lactococcus, Oenococcus, Streptococcus* and *Eubacterium.*

The term "ethanologenic" is intended to include cells that have the ability to produce ethanol from a carbohydrate as a primary fermentation product. The term is intended to include naturally occurring ethanologenic organisms, ethanologenic organisms with naturally occurring or induced mutations, and recombinant organism genetically engineered to produce ethanol from a carbohydrate as a primary fermentation product.

The term "non-ethanologenic" is intended to include cells that are unable to produce ethanol from a carbohydrate as a primary non-gaseous fermentation product; i.e., cells that produce ethanol as a minor fermentation product. The term "primary fermentation product" is intended to include non-gaseous products of fermentation (e.g., ethanol) that comprise greater than about 40%, 50%, 60%, 70%, 80%, 85%, 90%, 91%, 92%, 93%, 94%, 95% of total non-gaseous product. The primary fermentation product is the most abundant non-gaseous product. In certain embodiments of the invention, the primary fermentation product is ethanol. In further embodiments, the primary fermentation products are produced by the host grown in mineral salts medium.

The term "minor fermentation product" as used herein is intended to include non-gaseous products of fermentation (e.g., ethanol) that comprise less than 40%, for example 20%, 30%, 40%, of total non-gaseous product.

The term "anaerobic conditions" in intended to include conditions in which there is significantly less oxygen than is present in an aerobic environment. In particular embodiments, there is 40%, 50%, 60%, 70%, 80%, 85%, 90%, 91%, 92%, 93%, 94%, 95% less oxygen in the anaerobic environment than in the aerobic environment.

The term "simultaneous saccharification and fermentation" or "SSF" is intended to include the use of one or more recombinant hosts (or extracts thereof, including purified or unpurified extracts) for the contemporaneous degradation or depolymerization of a complex sugar and bioconversion of that sugar residue into ethanol by fermentation. SSF is a well-known process that can be used for breakdown of biomass to polysaccharides that are ultimately convertible to ethanol by bacteria. Reflecting the breakdown of biomass as it occurs in nature, SFF combines the activities of fungi (or enzymes such as cellulases extracted from fungi) with the activities of ethanologenic bacteria (or enzymes derived therefrom) to break down sugar sources such as lignocellulose to simple sugars capable of ultimate conversion to ethanol. SSF reactions are typically carried out at acid pH to optimize the use of the expensive fungal enzymes.

The term "homologous recombination" refers to the crossing over of DNA that occurs between two homologous DNA molecules. According to the invention, homologous recombination can occur between genes to restore gene function, i.e. homologous recombination to restore pflB function. In another embodiment, homologous recombination can be used to remove an antibiotic resistance marker.

The terms "saccharide," "saccharide source," "oligosaccharide source," "oligosaccharide," "complex cellulose," "complex carbohydrate," "complex sugar," "polysaccharide," "sugar source," "source of a fermentable sugar" and the like are intended to include any carbohydrate source comprising more than one sugar molecule.

Sugars include glucose, xylose, arabinose, mannose, galactose, sucrose, and lactose. The term "saccharide," as used herein, also includes, e.g., disaccharides, trisaccharides, oligosaccharides, and polysaccharides. These carbohydrates may be derived from any unprocessed plant material or any processed plant material. Examples are wood, paper, pulp, plant derived fiber, or synthetic fiber comprising more than one linked carbohydrate moiety, i.e., one sugar residue. One particular saccharide source is "lignocellulose," which represents approximately 90% of the dry weight of most plant material and contains carbohydrates, e.g., cellulose, hemicellulose, pectin, and aromatic polymers, e.g., lignin. Cellulose makes up 30%-50% of the dry weight of lignocellulose and is a homopolymer of cellobiose (a dimer of glucose). Similarly, hemicellulose makes up 20%-50% of the dry weight of lignocellulose and is a complex polymer containing a mixture of pentose (xylose, arabinose) and hexose (glucose, mannose, galactose) sugars which contain acetyl and glucuronyl side chains. Pectin makes up 1%-20% of the dry weight of lignocellulose and is a methylated homopolymer of glucuronic acid. Other saccharide sources include carboxymethyl cellulose (CMC), amorphous cellulose (e.g., acid-swollen cellulose), and the cellooligosaccharides cellobiose, cellotriose, cellotetraose, and cellopentaose. Cellulose, e.g., amorphous cellulose may be derived from a paper or pulp source (including, e.g., fluid wastes thereof) or, e.g., agricultural byproducts such as corn stalks, soybean solubles, or beet pulp. Any one or a combination of the above carbohydrate polymers is a potential source of sugars for depolymerization and subsequent bioconversion to ethanol by fermentation according to the products and methods of the present invention.

The term "obtaining" as in "obtaining the recombinant bacterium" is intended to include purchasing, preparing, engineering or otherwise acquiring the recombinant bacterium.

The term "providing" as in "providing the recombinant bacterium" is intended to include selling, distributing or otherwise making available the recombinant bacterium.

"ATCC" followed by a number appearing in parentheses following an organism name refers to a deposit of the organism made with the American Type Culture Collection, 10801 University Blvd. Manassas, Va. 20110-2209.

"NRRL" followed by a number appearing in parentheses following an organism name refers to a deposit of the organism made with the National Center for Agricultural Utilization Research, 1815 North University Street, Peoria, Ill. 61604-3999.

II. Recombinant Cells

As discussed, the invention provides new and recombinant cells, in particular recombinant bacteria, suitable for degrading sugars. The cells have improved ethanol production capabilities, particularly in mineral salts medium. The cells comprise a full complement of heterologous ethanol production genes. Expression of the full complement of heterologous ethanol production genes causes the recombinant cells to produce ethanol as the primary fermentation product.

The invention also provides a host cell that serves as the basis for the development of a recombinant cell that is genetically engineered to comprise a full complement of heterologous ethanol production genes. Accordingly, the host cell can be a cell of a higher eukaryotic organism such as a nematode, an insect, a reptile, a bird, an amphibian, or a mammal. The cell can also be a cell of a single-celled or multi-cellular microorganism, such as a fungus, yeast, or bacterium. The recombinant host cells and recombinant cells derived therefrom are intended to include cells suitable for, or subjected to, genetic manipulation, or to incorporate heterologous polynucleotide sequences by transfection. Recombinant host cells include progeny of the host cell originally transfected.

Accordingly, suitable host cells in accordance with the invention include yeast cells such as, e.g., *Saccharomyces cerevisiae*. Other yeast cells in accordance with the invention include, e.g., *Saccharomyces, Schizosaccharomyces, Hansenula, Pachyosolen, Kluyveromyces, Debaryomyces, Yarrowia*, and *Pichia*.

The host cell can be a non-recombinant or recombinant bacterial host cell. In certain embodiments, bacterial host cells in accordance with the invention include Gram-positive bacteria, e.g., *Bacillus, Clostridium, Corynebacterium, Geobacillis, Lactobacillis, Lactococcus, Oenococcus, Streptococcus* and *Eubacterium*. In other embodiments, bacterial host cells include Gram-negative bacteria and include, for example, *Acinetobacter, Gluconobacter, Escherichia, Zymomonas, Geobacter, Shewanella, Salmonella, Shigella, Eneterobacter, Citrobacter, Erwinia, Serratia, Proteus, Hafnia, Yersinia, Morganella, Edwardsiella*, and *Klebsiella*. Exemplary bacterial host cells in accordance with the invention include non-recombinant bacteria such as, e.g., *Escherichia coli* B, (ATCC 11303), and recombinant bacteria such as, e.g., *E. coli* KO11 (ATCC 55124) (Ohta et al. 1991). These can also be characterized by their rate of ethanol production from xylose in mineral salts medium. For example, *Escherichia coli* produces 9.1 gram/Liter ethanol in mineral medium in the presence of complex nutrients, and *E. coli* strain KO11 (ATCC 11303) produces 43.2 gram/Liter ethanol in mineral salts medium in the presence of complex nutrients, and 26.9 gram/Liter ethanol in mineral salts medium in the absence of complex nutrients.

As discussed, the invention provides recombinant cells, in particular recombinant bacteria, comprising a full complement of heterologous ethanol production genes. The recombinant bacteria of the invention are able to produced ethanol as the primary fermentation product when grown in mineral salts medium.

A full complement of heterologous ethanol production genes includes substantially all the genes that have evolved in an ethanologenic organism from which the genes are derived that comprise the organism's natural ethanol production pathway. Included within the scope of the invention are heterologous ethanol production genes derived from yeast and Gram-positive or Gram-negative bacteria. Thus, suitable heterologous polynucleotide sequences for use in constructing recombinant organisms in accordance with the invention are derived from, e.g., adh and/or pdc genes from naturally occurring ethanologenic organisms, such as *Zymomonas mobilis* and *Saccharomyces cerevisiae*, as well as *Zymobacter palmae, Acetobacter pasteurianus* and *Sarcinia ventriculi* (WO2003/025117 and herein incorporated by reference; Talarico et al. 2005). Other naturally occurring ethanologenic organisms from which ethanol production genes can be derived for use in the invention include fungi and most plants.

One or more of the ethanol production genes comprising the full complement can be derived from different organisms or from the same organisms. In advantageous embodiments, the genes comprising the full complement are derived from the same organism.

In one embodiment of the invention, the genes comprising the full complement of heterologous ethanol production genes are pdc, adhA and adhB. In an advantageous embodiment, the pdc, adhA and adhB genes are from *Zymomonas mobilis*, a naturally occurring ethanologenic bacterium.

Included within the scope of the present invention are heterologous ethanol production genes or gene products which differ from naturally-occurring ethanol production genes, for example, genes which have nucleic acids that are mutated, inserted or deleted, but which encode polypeptides substantially similar and functionally equivalent to the naturally-occurring gene products of the present invention, e.g., a mutant polypeptide having pyruvate decarboxylase activity that serves to direct the flow of pyruvate into ethanol during fermentation.

For example, it is well understood to one of skill in the art that nucleic acids which code for conservative amino acid substitutions can be mutated (e.g., by substitution). It is further well understood to one of skill in the art that amino acids in the naturally occurring gene products can be substituted, added or deleted to a certain degree without substantially affecting the function of a gene product (e.g., without affecting the biological function of pyruvate decarboxylase as an enzyme that serves to direct the flow of pyruvate into ethanol during fermentation) as compared with a naturally-occurring gene product. These well understood principles are included within the scope of the present invention. Thus, although in some embodiments, the full complement of heterologous ethanol production genes can comprise, for example, the naturally occurring pdc, adhA and adhB genes of *Zymomonas mobilis*, one or more genes of the full complement can be mutated forms of naturally occurring ethanol production genes, e.g., *Zymomonas mobilis* ethanol production genes.

In particular aspects of the invention, the full complement of heterologous ethanol production genes is integrated into a ribosomal RNA operon of the host cell. A ribosomal RNA operon is shared by most if not all cells, particularly microorganisms, particularly bacteria. As noted above, there are seven ribosomal RNA (rRNA) operons, called rrlA, rrnlE, rrlC, rrlD, rrlE, rrlG, and rrlH (Lindhal et al. 1986; Nomura et al., 1984). By convention, the term "rrnlE" refers to the rrnlE gene encoding the ribosomal RNAs (23S, 16S and 5S) whereas the term "RRLE" refers to a rrnlE gene product, i.e., a ribosomal RNA polypeptide. An rrnlE equivalent is present in most if not all organisms. An exemplary rrnlE sequence is specified by GeneID number 9485094. Each rRNA operon contains a 16S rRNA gene, a 23S rRNA gene, and a 5S rRNA gene, interspersed with various tRNA genes. The rrnD operon contains two 5S rRNA genes. "rrs" genes encode 16S rRNAs, "rrl" genes encode 23S rRNAs, and "rrf" genes encode 5S rRNAs. In advantageous embodiments, the RNA operon comprises a gene selected from the group consisting of rrl A, rrlB, rrlC, rrlD, rrlE, rrlG and rrlH.

In other aspects, the invention provides a recombinant bacterium which comprises a full complement of heterologous ethanol production genes as herein before described, wherein one or more antibiotic markers are removed. In general, genes encoding antibiotic markers are used in recombinant engineering techniques to identify or mark the presence of a particular genotype/phenotype. In certain embodiments, recombinant organisms of the invention which produce ethanol as the primary fermentation product can be inhibited by the presence of antibiotic markers. Therefore, such antibiotic markers are advantageously removed from the recombinant organisms. In some embodiments, antibiotic markers targeted for removal include, e.g., those selected from the group consisting of apramycin, kanamycin, tetracycline, ampicillin and chloramphenicol. In certain embodiments, apramycin and kanamycin markers are removed.

In still other aspects, the invention provides a recombinant bacterium which comprises a full complement of heterologous ethanol production genes as hereinbefore described, wherein one or more genes encoding polypeptides that interfere with or otherwise reduce the amount of ethanol produced by the full complement of heterologous ethanol production genes are inactivated. In accordance with the invention, any gene present in the host cell whose transcription interferes with or otherwise reduces the amount of ethanol produced by the full complement of heterologous ethanol production genes can be targeted for inactivation. Genes that can be targeted for inactivation include but are not limited to genes comprising the focA-pflB gene region, ldhA, ackA, adhE, frd operon, casAB and mgsA.

Thus, in certain embodiments, genes encoding polypeptides involved in all fermentative routes for NADH oxidation are inactivated. In particular embodiments, genes encoding polypeptides that are involved in alternate pathways for pyruvate metabolism are inactivated. Such genes include, for example, ackA and adhE. Together AckA and AdhE form a wasteful pathway for ethanol production that can, in certain embodiments, be eliminated as a wasteful route for use of NADH. LDHA eliminated oxidation of NADH by concurrent production-reduction of pyruvate to lactate.

In an advantageous embodiment, a msgA gene is inactivated by deletion. This gene encodes a protein involved in the Methylglyoxal Bypass, a spillover pathway which is a potential source of lactate in E. coli and which slows glycolysis and macromolecular synthesis (Totemeyer et al. 1998, Zhu et al. 2001).

In certain embodiments, the genes are endogenous to the host cell. Endogenous genes include, but are not limited to, ldhA, ackA, adhE, genes comprising the frd operon, genes comprising the focA-pflB gene region and mgsA. In other embodiments, the genes are heterologous to the host cell. Heterologous genes include, but are not limited to, casAB.

In other aspects, the invention provides a recombinant bacterium which comprises a full complement of heterologous ethanol production genes as hereinbefore described, and which further comprises one or more genes that encode polypeptides that facilitate production of ethanol or otherwise increase the amount of ethanol produced by the full complement of heterologous ethanol production genes. Such genes can be endogenous or heterologous and are integrated into the host cell by any number of techniques well known to those of skill in the art.

In another aspect, the invention provides a recombinant bacterium which comprises a full complement of heterologous ethanol production genes as hereinbefore described, and where the recombinant bacterium is prepared by a process comprising the steps of the method as described in any of the aspects of the invention.

Any gene which encodes a polypeptide that facilitates production of ethanol or otherwise increases the amount of ethanol produced by the full complement of heterologous ethanol production genes can be targeted for integration into the host cell. Such genes include, e.g., those that encode a secretory protein/s, a polysaccharase e.g., a glucanase, such as an endoglucanase or exoglucanase, a cellobiohydrolase, β-glucosidase, endo-1, 4-β-xylanase, β-xylosidase, α-glucuronidase, α-L-arabinofuranosidase, acetylesterase, acetylxylanesterase, α-amylase, β-amylase, glucoamylase, pullulanase, β-glucanase, hemicellulase, arabinosidase, mannanase, pectin hydrolase, and pectate lyase. A naturally occurring gene or a gene derived from the naturally occurring gene can be integrated. Thus, this aspect of the invention encompasses genes or gene products which differ from naturally-occurring genes and includes, for example, genes which have nucleic acids that are mutated, inserted or deleted, but which encode polypeptides substantially similar and functionally equivalent to the naturally-occurring gene products. In certain embodiments, the gene, for example the est gene of Pseudomonas putida (NRRL B-18435), encodes an esterase. Integration of the estZ gene helps reduce the production of ethyl acetate, a minor side product of ethanol production. Ethyl acetate separation from ethanol during the final purification steps adds cost to the process. Although the increase in yield of ethanol produced may not be significant, the production of ethanol is facilitated in that changes in the cost of purification of the ethanol can be more significant if the production of ethyl acetate is reduced. Other additional genes which might be considered include, but are not limited to, genes encoding enzymes for the hydrolysis of small saccharides and polysaccharides, for example casAB from K. oxytoca and celY and celZ encoding endoglucanases from E. chrysanthemi.

In other embodiments, the genes, for example the lacA and lacY genes of E. coli, encode galactose transacetylase and permease, respectively. In still other embodiments, exemplary genes include those that encode secretory proteins, e.g., pul and out genes (WO2000/071729), enzymes for the hydrolysis of small saccharides and polysaccharides, for example, the casAB genes from Klebsiella oxytoca (U.S. Pat. No. 6,102,690), celY and celZ genes that encode endoglucanases from Erwinia chrysanthemi (U.S. Pat. No. 7,026,152) and genes that encode glucose uptake pathways (U.S. Pat. No. 5,602,030).

The recombinant organisms provided by the invention are characterized by their ability to produce ethanol as the primary fermentation product. They are further characterized by their ability to produce ethanol as the primary fermentation product when grown in mineral salts medium. As discussed, the recombinant organisms of the invention comprise a full complement of heterologous ethanol production genes and, therefore, are ethanologenic. By ethanologenic is meant that the ethanol produced comprises greater than 40%, 50%, 60%, 70%, 80%, 85%, 90%, 91%, 92%, 93%, 94%, 95% of total non-gaseous product. The primary fermentation product is the most abundant non-gaseous product produced under anaerobic conditions, in particular when grown in mineral salts medium.

Exemplary recombinant organisms in accordance with the invention are novel E. coli strains LY165 (NRRL B-30952) and LY168 (NRRL B-30953). In accordance with an embodiment of the invention, these novel E. coli strains are produced from the recombinant E. coli KO11 (ATCC 55124) (Ohta et al. 1991), which is used as the host cell. In accordance with other embodiments of the invention, these novel E. coli strains can be produced from E. coli strain SZ110 (NRRL B-30951). Methods for producing these novel strains are described in the examples below.

Recombinant bacteria in accordance with the invention, e.g., E. coli strains LY165 (NRRL B-30952) and LY168 (NRRL B-30953), produce ethanol as the primary fermentation product when grown in mineral salts medium. Mineral salts medium is a medium that enables a recombinant bacterium of the invention to grow under anaerobic conditions according to the methods of the invention, without the need to add complex nutrients. In a particular embodiment of the invention, the mineral salts medium of the invention can be defined as containing per liter: 3.5 g $KH_2PO_4$, 5.0 g $K_2HPO_4$, 3.5 g $(NH_4)_2HPO_4$, 0.25 g $MgSO_4.7 H_2O$, 15 mg $CaCl_2.2 H_2O$, 0.5 mg of thiamine, and 1 mL of trace metal stock, supplemented with 2(w/v) % to 9(w/v) % xylose. Trace metal stock can be prepared in 0.1M HCl (per liter: 1.6 g $FeCl_3$, 0.2 g $CoCl_2.6H_2O$, 0.1 g $CuCl_2$, 0.2 g $ZnCl_2.4H_2O$, 0.2 g $NaMoO_4$, 0.05 g $H_3BO_3$) (Causey et al., 2003). In advantageous embodiments, betaine, a well-known bacterial osmoprotectant, may be added to the mineral salts media. In other embodiments, the mineral salts medium can be defined as AM1 medium, containing per liter: 2.63 g (NH4)2HPO4, 0.87 g NH4H2PO4, 0.375 g/L MgSO4.7H2O, 0.149 g KCl, 0.0163 g Betaine HCl (pH 7.4), and 1.5 mL of trace metal stock, supplemented with 2 (w/v) % to 14 (w/v) % sugar, as indicated. This minimal salts medium has been described in the art as AM1 medium (Martinez et al., 2007). In further embodiments, trace metal stock can be prepared in 0.1M HCl (per liter: 1.6 g FeCl3.6H2O, 0.2 g CoCl2.6H2O, 0.1 g CuCl2.2H2O, 0.2 g ZnCl2, 0.2 g Na2MoO4.2H2O, 0.05 g H3BO3, 0.33 g MnCl2.4H2O.

III. Methods of making

The present invention provides methods of making the recombinant organisms having the aforementioned attributes. Accordingly, in another aspect, the invention provides a method for producing a recombinant bacterium that comprises a full complement of heterologous ethanol production genes, wherein the expression of the full complement of heterologous ethanol production genes causes the recombinant bacterium to produce ethanol as the primary fermentation product. The method comprises the step of integrating the full complement of heterologous ethanol production genes into a host bacterium, thereby producing a recombinant bacterium that produces ethanol as the primary fermentation product.

Methods of making recombinant ethanologenic microorganisms are known in the art of molecular biology. Suitable materials and methods and recombinant host organisms are described, for example, in U.S. Pat. Nos. 7,026,152, 6,849,434, 6,333,181, 5,821,093; 5,482,846; 5,424,202; 5,028,539; 5,000,000; 5,487,989, 5,554,520, and 5,162,516 and in WO2003/025117 hereby incorporated by reference, and may be employed in carrying out the present invention.

The bacterium of the invention comprises a full complement of heterologous ethanol production genes. The full complement of genes includes a nucleic acid molecule (e.g., a DNA molecule or segment thereof), for example, a polypeptide or RNA-encoding nucleic acid molecule that, in an organism, is separated from another gene or other genes, by intergenic DNA (i.e., intervening or spacer DNA which naturally flanks the gene and/or separates genes in the chromosomal DNA of the organism). A gene can direct synthesis of an enzyme or other polypeptide molecule (e.g., can comprise coding sequences, for example, a contiguous open reading frame (ORE) which encodes a polypeptide) or can itself be functional in the organism. A gene in an organism can be clustered in an operon, as defined herein, wherein the operon is separated from other genes and/or operons by intergenic DNA. Individual genes contained within an operon can overlap without intergenic DNA between the individual genes. Also included in the scope of the invention are promoterless operons, which are operons lacking the promoter portion (e.g., an frd operon).

An isolated gene as described herein, includes a gene which is essentially free of sequences which naturally flank the gene in the chromosomal DNA of the organism from which the gene is derived (i.e., is free of adjacent coding sequences which encode a second or distinct polypeptide or RNA molecule, adjacent structural sequences or the like) and optionally includes 5' and 3' regulatory sequences, for example promoter sequences and/or terminator sequences. An isolated gene includes predominantly coding sequences for a polypeptide (e.g., sequences which encode PDC polypeptides).

As mentioned above, the full complement of heterologous ethanol producing genes is incorporated into a host cell. In certain embodiments, the host cell is a bacterium and is also referred to as "the parent strain".

In some embodiments, the parent strain is a non-recombinant bacterium. For example, the parent strain can be a naturally occurring non-ethanologenic bacterium, e.g., *E. coli* W.

In other embodiments of the invention, the parent strain can be a recombinant organism. In such embodiments, the parent strain can contain both wild-type and heterologous genes encoding polypeptides that reduce the amount of ethanol produced by the strain, for example, when grown in mineral salts medium. Wild-type genes include genes that are present in the parent strain. Heterologous genes include exogenous genes that have been added to the parent strain.

Exemplary host cells for use in the methods according to the invention include, e.g., *E. coli* strains KO4 (ATCC 55123), KO11 (ATCC 55124), and KO12 (ATCC 55125), and *Klebsiella oxytoca* strain P2 (ATCC 55307) (U.S. Pat. No. 5,821,093). Other examples of suitable host cells include *E. coli* (ATCC 11303), *E. coli* DH5α, *E. coli* KO4 (ATCC 55123), *E. coli* LY01 (ATCC PTA-3466), *E. coli* W (ATCC 9637), and *K. oxytoca* M5A1 (ATCC 68564).

The invention also encompasses various embodiments of the method for making the recombinant organisms described herein. Thus, in one embodiment, the method further comprises integrating the full complement of heterologous ethanol production genes into a ribosomal RNA operon. In an advantageous embodiment, the ribosomal RNA operon comprises a gene selected from the group consisting of rrlA, rrlE, rrnC, rrlD, rrlE, rrlG and rrlnH. In another advantageous embodiment, the ribosomal RNA operon comprises rrlE.

In yet another embodiment, the method further comprises removing one or more antibiotic markers. In one embodiment, the antibiotic markers are selected from the group consisting of apramycin, kanamycin, tetracycline, ampicillin and chloramphenicol. In a particular embodiment, the antibiotic markers are apramycin and kanamycin. The antibiotic marker can be removed by inactivating (e.g., by deletion) the gene coding for the marker by any of a number of methods known in the art. In an advantageous embodiment, the gene(s) encoding the antibiotic marker(s), e.g., kanamycin and apramycin, is removed by homologous recombination, using a recombinase.

In yet another embodiment, the method further comprises inactivating one or more genes encoding polypeptides that interfere with or otherwise reduce the amount of ethanol produced by the full complement of ethanol production genes. In accordance with the invention, such genes are inactivated by any of a number of means, well known to those of skill in the art, by which a gene is stopped from encoding its intended polypeptide or from encoding an active form of its intended polypeptide. Accordingly, such genes are inactivated by, for example, mutation, deletion, insertion, duplication, missense, frameshift, repeat, nonsense mutation, or other alteration or modification such that gene activity (i.e., transcription) is blocked or transcription results in functionally inactive polypeptides. In accordance with advantageous embodiments of the invention, genes are inactivated by deletion.

In a further embodiment, the method further comprises integrating one or more heterologous genes that encode polypeptides that facilitate production of ethanol or otherwise increase the amount of ethanol produced by the full complement of heterologous ethanol production genes. The very same methods described above that are used to integrate the full complement of ethanol production genes can be used to integrate genes that encode polypeptides that facilitate production of ethanol or otherwise increase the amount of ethanol produced by the full complement of heterologous ethanol production genes.

One of ordinary skill in the art will recognize that based on the aforementioned examples, and based on homology among bacterial strains, the methods of the instant invention are not limited to the strains taught in the instant application.

IV. Methods Of Use-Methods for Producing Ethanol

The recombinant bacteria of the invention produce ethanol from an oligosaccharide source. Accordingly, the invention provides a method for producing ethanol from an oligosaccharide source comprising contacting said oligosaccharide with a recombinant bacterium of the invention under conditions appropriate for ethanol production, thereby producing ethanol from an oligosaccharide source. In one embodiment, the oligosaccharide and the recombinant bacterium are contacted in mineral salts medium, optionally containing betaine. In a particularly advantageous embodiment, the recombinant bacteria grow in mineral salts medium and produce ethanol as the primary fermentation product in high titers.

In accordance with the methods of the invention, the recombinant bacteria described herein degrade or depolymerize a complex saccharide into a monosaccharide. Subsequently, the recombinant bacteria, by virtue of the full complement of heterologous ethanol production genes they carry, catabolize the simpler sugar into ethanol by fermentation. This process of concurrent complex saccharide depolymerization into smaller sugar residues followed by fermentation is referred to as simultaneous saccharification and fermentation (SSF).

Typically, fermentation conditions are selected that provide an optimal pH and temperature for promoting the best growth kinetics of the producer host cell strain and catalytic conditions for the enzymes produced by the culture (Doran et al., (1993) Biotechnol. Progress. 9:533-538). A variety of exemplary fermentation conditions are disclosed in U.S. Pat. Nos. 5,487,989 and 5,554,520. In certain embodiments, optimal conditions included temperatures ranging from about 25 to about 43° C. and a pH ranging from about 4.5 to 8.0. Other conditions are discussed in the Examples. Moreover, it will be appreciated by the skilled artisan that only routine experimentation is needed, using techniques known in the art, for optimizing a given fermentation reaction of the invention.

Currently, the conversion of a complex saccharide such as lignocellulose is a very involved, multi-step process. For example, the lignocellulose must first be degraded or depolymerized using acid hydrolysis. This is followed by steps that separate liquids from solids and these products are subsequently washed and detoxified to result in cellulose that can be further depolymerized and finally, fermented by a suitable ethanologenic host cell. In contrast, the fermenting of corn is much simpler in that amylases can be used to break down the corn starch for immediate bioconversion by an ethanologenic host in essentially a one-step process.

Accordingly, it will be appreciated by the skilled artisan that the recombinant hosts and methods of the invention afford the use of a similarly simpler and more efficient process for fermenting lignocellulose. For example, the method of the invention is intended to encompass a method that avoids acid hydrolysis altogether. Moreover, the hosts of the invention have the following advantages, 1) efficiency of pentose and hexose co-fermentation; 2) resistance to toxins; 3) production of enzymes for simultaneous saccharification and fermentation; and 4) environmental hardiness. Therefore, the complexity of depolymerizing lignocellulose can be simplified using an improved biocatalyst of the invention. Indeed, in one preferred embodiment of the invention, the reaction can be conducted in a single reaction vessel and in the absence of acid hydrolysis, e.g., as an SSF process.

One advantage of the invention is the ability to use a saccharide source that has been, heretofore, underutilized. Consequently, a number of complex saccharide substrates may be used as a starting source for depolymerization and subsequent fermentation using the recombinant bacteria and methods of the invention. Ideally, a recyclable resource may be used in the SSF process. Mixed waste office paper is a preferred substrate (Brooks et al., (1995) Biotechnol. Progress. 11:619-625; Ingram et al., (1995) U.S. Pat. No. 5,424,202), and is much more readily digested than acid pretreated bagasse (Doran et al., (1994) Biotech. Bioeng. 44:240-247) or highly purified crystalline cellulose (Doran et al., (1993) Biotechnol. Progress. 9:533-538). Glucanases, both endoglucanases and exoglucanases, contain a cellulose binding domain, and these enzymes can be readily recycled for subsequent fermentations by harvesting the undigested cellulose residue using centrifugation (Brooks et al., (1995) Biotechnol. Progress. 11:619-625). Such approaches work well with purified cellulose, although the number of recycling steps may be limited with substrates with a higher lignin content. Other substrate sources that are within the scope of the invention include any type of processed or unprocessed plant material, e.g., lawn clippings, husks, cobs, stems, leaves, fibers, pulp, hemp, sawdust, newspapers, etc.

As noted above, the recombinant organisms provided by the invention produce ethanol as the primary fermentation product, in particular when grown in mineral salts medium. In mineral salts medium, the novel recombinant E. coli LY168 of the invention produces ethanol at a rate of 45.5 g/L in the absence of complex nutrients, and the novel recombinant E. coli LY165 produces ethanol at a rate of 44.9 g/L in the absence of complex nutrients. In contrast, E. coli KO11 produces ethanol at a rate of 26.9 g/L in mineral salts medium in the absence of complex nutrients, and at a rate of 43.2 g/L after the addition of complex nutrients. Thus, the novel recombinant E. coli LY168 and LY165 of the invention produces more ethanol than E. coli KO11 in mineral salts medium and without the need for added and costly complex nutrients.

The invention is further illustrated by the following examples, which should not be construed as limiting.

Exemplification

Materials and Methods:

The following materials and methods were used throughout the Examples below.

1. Organisms and Culture Conditions

Strains and Plasmids:

Table 1, below, lists the organisms and plasmids used to construct the recombinant microorganisms of the invention.

TABLE 1

E. coli strains and plasmids.

| Strains/plasmids | Relevant Genotype | Source or Citation |
|---|---|---|
| DH5α | lacZ Δ M15 recA | Invitrogen |
| S17-1λpir | thi pro recA hsdR RP4-2-tet::Mu aphA::Tn7λpir, spc tet | de Lorenzo et al. 1990 |
| TOP10F' | F' {lacI$^q$ Tn10 tet)} | Invitrogen |
| W | Prototroph | ATCC 9637 |
| NC3 | B/r hsdR phn | Wanner et al. 1977 |
| KO11 | W Δfrd pfl$^+$ pfl::pdc$_{Zm}$ adhB$_{Zm}$ cat | Ohta et al. 1991 |
| SZ110 | W ΔadhE ΔackA Δpfl celY$_{Ec}$ casAcasB$_{Ko}$ | Zhou et al. 2005 |
| LY149 | SZ110 ΔldhA::FRT | This study |
| LY151 | LY149 pfl$^+$ (pflA-FRT-aac-FRT-ycaK), Aac$^R$ | This study |
| LY158 | LY151 pdc$_{Zm}$-adhA$_{Zm}$-adhB$_{Zm}$-FRT-kan-FRT, pfl$^+$ (pflA-FRT-aac-FRT-ycaK), Aac$^R$, Kan$^R$ | This study |
| LY159 | LY151 pdc$_{Zm}$-adhA$_{Zm}$-adhB$_{Zm}$-FRT-kan-FRT, pfl$^+$ (pflA-FRT-aac-FRT-ycaK), Aac$^R$, Kan$^R$ | This study |
| LY160 | LY158/159 rrlE'-pdc$_{Zm}$-adhA$_{Zm}$-adhB$_{Zm}$-FRT-rrlE', pfl$^+$ (pflA-FRT-ycaK) | This study |
| LY160im | LY160 rrlE'-pdc$_{Zm}$-adhA$_{Zm}$-adhB$_{Zm}$-FRT-rrlE', pfl$^+$ (pflA-FRT-ycaK) | This study |
| LY161 | LY158/159 rrlE'-pdc$_{Zm}$-adhA$_{Zm}$-adhB$_{Zm}$-FRT-rrlE', pfl$^+$ (pflA-FRT-ycaK) | This study |
| LY163 | LY160 lac'Y-FRT-lacA (ΔcasAcasB$_{Ko}$) | This study |
| LY165A | LY163 adhE'::Zm frg-estZ$_{Pp}$-FRT::adhE' | This study |
| LY165C | LY163 adhE'::Zm frg-estZ$_{Pp}$-FRT::adhE' | This study |
| LY168 | LY165C ΔmgsA::FRT | This study |
| LY168im | LY168 ΔmgsA::FRT | This study |
| LY169 | LY168im lacY-lacA+ | This study |
| LY170 | LY169 frdB'-cat-sacB-frdC' | This study |
| LY172 | LY170 frdA'-Zm frg-celY-frdC' ΔfrdB | This study |
| LY172im | LY172 frdA'-Zm frg-celY-frdC' ΔfrdB | This study |
| LY173 | LY172im ldhA'-cat-sacB-casA$_{Ko}$-casB$_{Ko}$-ldhA', Cam$^R$ | This study |
| LY178A, C, D E&F | LY173 ldhA'-Zm frg-casAcasB$_{Ko}$-ldhA' | This study |
| LY180 | LY178E ldhA'-Zm frg-casAcasB$_{Ko}$-ldhA' | This study |
| LY186 | LY180 ldhA'-Zm frg-casAcasB$_{Ko}$-ldhA' | This study |
| plasmids | | |
| pCCD5-lacZ | ColE1, rrnBT1 terminator, bla | Cebolla et al. 2002 |
| pCR2.1-TOPO | ColE1, TOPO T/A cloning vector, bla kan | Invitrogen |
| pKD46 | pSC101$^{rs}$, repA101 γβ exo, (Red recombinase), bla | Datsenko & Wanner 2000 |
| pFT-A | pSC101$^{rs}$, flp (FLP recombinase), bla | Posfai et al. 1997 |
| pBluescript II SK$^+$ | ColE1, bla | Stratagene |
| pLOI2228 | pSC101$^{rs}$, two FRT sites in MCS, cat | Martinez-Morales et al. 1999 |
| pLOI2511 | ColE1, with FRT sites flanking the kan, bla | Purvis et al. 2005 |
| pLOI3421 | ColE1, with FRT sites flanking the aac gene, bla aac | Wood et al. 2005 |
| pLOI3469 | R6K, oriT, PacI site within the Tn5 I and O ends, tnp, bla | Purvis et al. 2005 |
| pLOI3470 | pBluescript II SK$^+$, SacI(blunt)-PacI linker, KpnI(blunt)-PacI linker, pCCD5-laZ EcoRI-NotI (blunt) PCR product rrnBT1 terminator into EcoRI-SmaI, ColE1, bla | This study |
| pLOI3472 | pLOI3470, pLOI2511EcoRI-SmaI FRT-kan-FRT in BstXI, ColE1, bla kan | This study |
| pLOI3495 | pLOI3470, pLOI3421 EcoRI-SmaI FRT-aac-FRT in BamHI, PacI flanked FRT-aac-FRT, bla, aac | This study |
| pLOI3918 | pLOI2228, ClaI-HindIII deletion with PacI linker and FRT site deletion, pSC101$^{rs}$, cat | This study |
| pUC18 | ColE1, bla | New England Biolabs |
| pEL04 | ColE1, cat-sacB, Cam$^R$ | Lee et al. 2001 |
| ldhA | | |
| pLOI3497 | SmaI/EcoRI FRT-aac-FRT from pLOI3421 in MfeI/SalI of ldhA, ldhA'-FRT-aac-FRT-ldhA' bla, kan, aac | This study |
| pfl | | |
| pLOI3901 | ycaO-focA-pflB-pflA-FRT-aac-FRT-trm-ycaK-ycaN', ColE1, bla aac | This study |
| pdc, adhA, adhB | | |
| pLOI135 | Z. mobilis adhA, ColE1, bla | Keshav et al. 1990 |
| pLOI295 | Z. mobilis pdc-adhB, ColE1, bla | Ingram et al. 1987 |
| pLOI3491 | pdc-adhA-adhB-FRT-kan-FRT, R6K, oriT, tnp, bla kan | This study |

TABLE 1-continued

E. coli strains and plasmids.

| Strains/plasmids | Relevant Genotype | Source or Citation |
|---|---|---|
| Integration of ethanol genes site | | |
| pLOI3951 deletion of casAB | LY160 EcoRI genomic fragment, ColE1, bla | This study |
| pLOI392 estZ | lacY-FRT-kan-FRT-lacY, ColE1, kan bla | |
| pAH181 | P. putida 'pvdD estZfpvA'pvdE, ColE1, bla | Hasona et al. 2002 |
| pLOI3920 | adhE'-estZ-FRT-aac-FR-:adhE', pSC101$^{ts}$, cat aac | This study |
| pLOI3925A | adhE-Z. mobilis frg.-estZ-FRT-aac-FR-adhE', pSC101$^{ts}$, cat aac | This study |
| pLOI3925C | adhE'-Z. mobilis frg.-estZ-FRT-aac-FRT-adhE', pSC101$^{ts}$, cat aac | This study |
| mgsA | | |
| pLOI3940 | mgsA'-FRT-aac-FRT-mgsA', ColE1, bla kan aac | This study |
| frd region | | |
| pLOI3958 | frdB'-frdC', ColE1, bla | This study |
| pLOI3959 | frdB'-cat-sacB-frdC', ColE1, bla cat | This study |
| pLOI3961 | frdA'-Zm frg-celY-frdC', ColE1, bla | This study |
| ldhA-casAB | | |
| pLOI4162 | cat-sacB flanked by PacI sites, ColE1, bla | This study |
| pLOI1910 | casAB, ColE1, bla | Moniruzzaman et al., xxx |
| pLOI3971 | ldhA, ColE1, bla | This study |
| pLOI3972 | PCR of casAB from pLOI1910, ldhA'-casABKO-ldhA', ColE1, bla | This study |
| pLOI3973 | ldhA'-cat-sacB-casA-casB-ldhA', ColE1, bla | This study |
| pLOI3975 | ldhA-casA-casB-ldhA, pSC101$^{ts}$, cat | This study |
| pLOI3976A-K | ldhA'-Zm frg-casA-casB-ldhA, pSC101$^{ts}$, cat | This study |

E. coli DH5α, S17-1λpir, and TOP10F' were used as host for constructions and were grown in LB medium. Ampicillin (50 mg/liter), kanamycin (50 mg/liter), chloramphenicol (40 mg/liter) and apramycin (50 mg/liter) were added as appropriate for selection. Temperature-conditional plasmids were grown at 30° C.; all others were grown at 37° C.

Re-engineered ethanologenic strains were grown in NBS mineral salts medium (Causey et al., 2003) containing per liter: 3.5 g KH$_2$PO$_4$, 5.0 g K$_2$HPO$_4$, 3.5 g (NH$_4$)$_2$HPO$_4$, 0.25 g MgSO$_4$.7H$_2$O, 15 mg CaCl$_2$.2H$_2$O, 0.5 mg of thiamine, and 1 mL of trace metal stock, supplemented with 2(w/v) % to 9(w/v) % xylose. Trace metal stock can be prepared in 0.1M HCl (per liter: 1.6 g FeCl$_3$, 0.2 g CoCl$_2$.6H$_2$O, 0.1 g CuCl$_2$, 0.2 g ZnCl$_2$.4H$_2$O, 0.2 g NaMoO$_4$, 0.05 g H$_3$BO$_3$). Betaine (1 mM) and MOPS (4-Morpholinepropanesulfonic acid) buffer (100 mM, pH 7.4) were added where indicated, as described (Underwood et al. 2004).

After LY168 was developed a more economical mineral salts medium, AM1 medium, was used (Martinez et al., 2007) containing per liter: 2.63 g (NH4)2HPO4, 0.87 g NH4H2PO4, 0.375 g/L MgSO4.7H2O, 0.149 g KCl, 0.0163 g Betaine HCl (pH 7.4), and 1.5 mL of trace metal stock, supplemented with 2 (w/v) % to 14 (w/v) % sugar, as indicated. Trace metal stock can be prepared in 0.1M HCl (per liter: 1.6 g FeCl3.6H2O, 0.2 g CoCl2.6H2O, 0.1 g CuCl2.2H2O, 0.2 g ZnCl2, 0.2 g Na2MoO4.2H2O, 0.05 g H3BO3, 0.33 g MnCl2.4H2O).

Ethanologenic strains were screened on aldehyde indicator plates for alcohol dehydrogenase activity as previously described (Conway et al. 1987). Esterase activity was examined using the methyl red assay described previously (Hasona et al. 2002). Cellobiose utilization was evaluated using MacConkey agar with 2% cellobiose. Endoglucanase activity was evaluated on CMC agar plates (Wood et al., 1997).

2. Genetic Methods

Unless otherwise described, standard methods were used for plasmid construction, transformation, electroporation, conjugation, and PCR amplification (Miller, 1992; Sambrook & Russell 2001).

cat-sacB Procedure

In the first recombination using the cat-sacB cassette, part of the target gene was replaced by a DNA cassette containing a chloramphenicol resistance gene (cat) and levansucrase gene (sacB). In the second recombination, the cat-sacB cassette was removed by selection for resistance to sucrose, followed by testing for sensitivity to chloramphenicol. Cells containing the sacB gene accumulate levan during incubation with sucrose and are killed. Surviving recombinants are highly enriched for loss of the cat-sacB cassette.

A new cassette was constructed as a template to facilitate gene deletions. The cat-sacB region was originally amplified from pEL04 (Lee et al., 2001; Thomason et al., 2005) by PCR using the primer pair JMcatsacBNheI (Table 2), digested with NheI, and modified and ligated into a modified pUC19 vector with PacI sites flanking the inserted cassette, creating pLOI4162. The cat-sacB cassette can be digested with PacI, and used in subsequent ligations The primers used in the methods described are listed in Table 2, below.

TABLE 2

Primers

| Primer | | Sequence | |
|---|---|---|---|
| ldhA | N-terminus | 5'-TTGCTCTTCCATGAAACTCGCCGTTTATAGCACA-3' | (SEQ ID NO: 1) |
| | C-terminus | 5'-TTGCTCTTCGTTAAACCAGTTCGTTCGGGCAGG-3' | (SEQ ID NO: 2) |
| lacA | N-terminus | 5'-TTGCTCTTCCATGCCAATGACCGAAGAATAAGAG-3' | (SEQ ID NO: 3) |
| | C-terminus | 5'-TTGCTCTTCGTTAAACTGACGATTCAACTTTATA-3' | (SEQ ID NO: 4) |
| lacY | N-terminus | 5'-TTGCTCTTCCATGTACTATTTAAAAAACACAAAC-3' | (SEQ ID NO: 5) |
| | C-terminus | 5'-TTGCTCTTCGTTAAGCGACTTCATTCACCTGAC-3' | (SEQ ID NO: 6) |
| adhE | N-terminus | 5'-TTGCTCTTCCATGGCTGTTACTAATGTCGCTGAA-3' | (SEQ ID NO: 7) |
| | C-terminus | 5'-TTGCTCTTCGTTAAGCGGATTTTTTGCGTTTTTCT-3' | (SEQ ID NO: 8) |
| mgsA | N-terminus | 5'-TATTGCGCTGGTGGCACACG-3' | (SEQ ID NO: 9) |
| | C-terminus | 5'-ACGGTCCGCGAGATAACGCT-3' | (SEQ ID NO: 10) |
| estZ | N-terminus | 5'-AGATCTTCTGGAGAATCGAACGATGTCCCTG-3'[a] | (SEQ ID NO: 11) |
| | C-terminus | 5'-GAATTCATCACCGCCAAGTACAGCTT-3'[b] | (SEQ ID NO: 12) |
| adhA | N-terminus | 5'-ACTAGTGATCGTAATCGGCTGGCAAT-3'[c] | (SEQ ID NO: 13) |
| | C-terminus | 5'-ACTAGTGTTTATGCTTCCGCCTTCAC-3'[c] | (SEQ ID NO: 14) |
| ycaN-pflB' | N-terminus | 5'-GGCGCAATCGTTCATAGAGA-3' | (SEQ ID NO: 15) |
| | C-terminus | 5'-ATATGGCCGTGGCCGTATCA-3' | (SEQ ID NO: 16) |
| ycaO-pfLA' | N-terminus | 5'-AATGACGATGTGCCAGAAGG-3' | (SEQ ID NO: 17) |
| | C-terminus | 5'-GGTGTCGCGGTTATGACAAT-3' | (SEQ ID NO: 18) |
| rrlE-pdc | N-terminus | 5'-GGACGGAGAAGGCTATGTTG-3'[d] | (SEQ ID NO: 19) |
| | C-terminus | 5'-TGCGAAGTGATGCTTGAGAC-3'[e] | (SEQ ID NO: 20) |
| rrnBTI (terminator) | | 5'-AAGCGGCCGCAAATTTCCAGGCATCAAATAA-3'[a] | (SEQ ID NO: 21) |
| | | 5'-AAGAACGTGGGAATTCCCTGGCAGTTTATGG-3'[b] | (SEQ ID NO: 22) |
| lacZ-cynX | N-terminus | 5'-GAAGTGACCAGCGAATACCT-3' | |
| | C-terminus | 5'-GGTGATGCCTTCGGTGATTA-3' | |
| lacY' | N-terminus | 5'-TTAAGCTGGCACTGGAACTG-3' | |
| | C-terminus | 5'-AGCGACTTCATTCACCTGAC-3' | |
| frdB'-frdC' | N-terminus | 5'-ACCGCACGGCATAGGGCATT-3' | |
| | C-terminus | 5'-AGAGCTGCCGCCAGAGTGAT-3' | |
| JMcatsacB Nhe[g] | N-terminus | 5'-TTAGCTAGCATGTGACGGAAG-3' | |
| | C-terminus | 5'-CCGCTAGCATCAAAGGGAAAA-3' | |
| NhefrdB-C[g] | N-terminus | 5'-ACGCTAGCGTGTAATCACGCAGGAAGG-3' | |
| | C-terminus | 5'-ACGCTAGCTTACATGCGCGCGAAGGC-3' | |
| XhofrdA- NhecelY[gh] | N-terminus | 5'-ACCTCGAGTGCACAGGCTGTTCCAGACC-3' | |
| | C-terminus | 5'-ACGCTAGCGCGCGTTGGCCGATTCATTA-3' | |
| BglIIcasA- MfeIcasB[ij] | N-terminus | 5'-TGAGATCTTTAAGGAAAAACAGCATGGA-3' | |
| | C-terminus | 5'-GCACAATTGCGCGTAACGGCGTAATACGAA-3' | |
| BglIIldhA- ldhA[i] | N-terminus | 5'-GACAGATCTCGATGGCGTGTTCAGCAACGG-3' | |
| | C-terminus | 5'-CCAGTCGCGGTGCATTGATTGATTCTCAGG-3' | |

[a]includes BglII site; [b]includes EcoRI site; [c]includes SpeI site; [d]within rrnB; [e]within pdc; [f]includes NotI site Taq PCR Master Mix (QIAGEN, Inc., Valencia, Calif.) was used to construct deletions and for analyses. Platinum Pfx DNA polymerase (Invitrogen, Carlsbad, Calif.) and Easy-A High-Fidelity PCR Cloning Enzyme (Stratagene, La Jolla, Calif.) were used to amplify functional genes for chromosomal integration. Integration of linearized DNA was facilitated by using plasmid pKD46 (Datsenko & Wanner 2000). FRT-flanked antibiotic genes were used for selection to facilitate subsequent removal with recombinase (Martinez-Morales et al. 1999; Posfai et al. 1997). Chromosomal constructions were verified by PCR analyses and phenotype.

In certain embodiments of the invention, antibiotic markers, e.g. antibiotic gene markers, can be removed by homologous recombination. Homologous recombination is carried out using a using recombinase that introduces site-specific breaks into the target DNA, for example a flp recombinase.

3. Fermentation

Fermentation tests were carried out in 500 mL fermentation vessels with automatic pH control (37° C., pH 6.5, and 150 rpm; 350 ml working volume) as described by Underwood et al. 2004, using NBS mineral salts medium (9% xylose, and 1 mM betaine where indicated) or AM1 medium in 95 or 14% xylose where indicated. Pre-inocula were grown at 37° C. for 24-48 h in NBS mineral medium containing 9.0 (w/v) % xylose and 1 mM betaine in standing screw capped tubes, and transferred to small fermentors. After incubation for 24 h, broth was used to inoculate for test fermentations (10-16 mg dcw l$^{-1}$ inoculum). In some cases, small fermentations were sequentially transferred after 24 h or 48 h to co-select improved growth and ethanol production. No antibiotics were added to broth for seed or fermentation tests.

4. Analytical Methods

Cell mass was estimated from the optical density at 550 nm with a Bausch & Lomb Spectronic™ 70 spectrophotometer. Ethanol was measured by gas chromatography (Ohta et al. 1991). Organic acids were determined by HPLC as described (Causey et al. 2003).

EXAMPLE 1

Construction of New Host Strains for Z. mobilis Ethanol Genes

The Z. mobilis cassette encoding ethanol production (pdc, adhB, cat) genes was removed from KO11 by deleting the focA-pflB region (Zhou et al. 2005). Additional genes encoding alternative routes for pyruvate metabolism, including ackA and adhE, were also deleted, leaving only D (−)-lactate dehydrogenase (ldhA). The resulting strain, SZ110, and further derivatives thereof produced lactic acid at high yields in mineral salts medium with 1 mM betaine (Zhou et al. 2005, Zhou et al. 2006).

Referring to FIG. 1A, Strain SZ110 was re-engineered as a host for insertion of new ethanol genes from Z. mobilis by first deleting ldhA. After cloning into pCR2.1-TOPO using primers listed in Table 2, the central MfeI to SalI fragment (484 bp, Klenow-treated) was replaced with a Klenow-treated SmaI to EcoRI fragment (1,942 bp) containing an FRT-flanked aac gene from pLOI3421 (Wood et al. 2005) to produce pLOI3497. The resulting cassette (ldhA'-FRT-aac-FRT-ldhA') was removed as a 2.5 kb EcoRI fragment for integration into SZ110. After elimination of aac with recombinase, the resulting strain was designated LY149.

The LY149 strain lacks all major routes for anaerobic NADH oxidation and is incapable of fermentative growth on sugars even in rich medium. Since the deletions of adhE and ackA in LY149 make a deletion of pflB unnecessary, this region was restored by homologous recombination using a 9 kb fragment from pLOI3901 (FIG. 1B) containing the ycaN'-focA region from E. coli W.

To construct this plasmid, the pflB region (ycaO-ycaN) was amplified as 2 PCR fragments and assembled into pLOI3495 in three pieces: 1) HindIII to SfcI (Klenow) fragment (ycaN'-ycaK; 764 bp) ligated into unique EcoRV and HindIII sites; 2) Klenow-treated SfcI fragment (pflA-pflB'; 2,084 bp) ligated into the Klenow-treated SpeI site); and 3) AscI to NotI fragment (pfl'-ycaO; 4,657 bp) ligated into corresponding sites of pLOI3495. In pLOI3901, an FRT-flanked aac gene for selection is located between ycaK and pflA.

Function of pflB was restored in strain LY149 by homologous recombination using the NotI to HindIII fragment (ycaO-focA-pflB-pflA-FRT-aac-FRT-rrnBT1 terminator-ycaK-ycaN') with selection for apramycin resistance. The resulting strain was designated LY151; this strain produced formate, indicative of pyruvate formate lyase (pflB) activity.

EXAMPLE 2

Construction of Transposome Containing a Full Set of Ethanol Genes from Z. mobilis In previous studies, a mineral set of genes from Z. mobilis (pdc adhB, cat for selection) was integrated behind the pflB promoter of E. coli to construct KO11 (Ohta et al. 1991). In contrast, a different approach has been taken using a Tn5 transposon to randomly integrate a promoterless operon containing the full set of ethanol genes (pdc, adhA, and adhB) with a removable antibiotic marker using a new vector, pLOI3491, as illustrated in FIG. 1C.

Plasmid pLOI3491 was constructed by ligating the Z. mobilis adhA gene (PCR product containing the ribosomal binding site and translational terminator with flanking SpeI sites; 1,157 bp; Table 2) into the unique SpeI site between pdc and adhB in pLOI295. The resulting promoterless operon (4,352 bp) was removed by digestion with EcoRI and BamHI, and ligated into corresponding sites adjacent to the FRT-flanked kan gene in pLOI3472. This created a PacI-flanked cassette (pdc-adhA-adhB-FRT-kan-FRT) of 5,587 by that was subsequently inserted into the unique PacI site of pLOI3469 (between tandem Tn5 integration sites), to produce pLOI3491 (FIG. 1C). This conjugal plasmid also contained Tn5 transposase (tnp), bla, and a conditional replicon (R6K) in trans to the segment targeted for integration.

EXAMPLE 3

Integration and Selection of New Ethanologenic E. coli

The donor strain, S17-1λpir, is unable to grow in mineral salts medium due to an auxotrophic requirement for proline. The recipient strain, LY151, is unable to grow fermentatively due to the lack of a pathway for NADH oxidation. Together, these provided a unique opportunity for direct functional selection without antibiotics. Since ATP production by glycolysis and growth are obligately coupled to functional expression of a fermentation pathway, selection for growth in NBS mineral salts medium was used to co-select optimal strains (site of insertion, expression level) for ethanol production from a library of random LY151 exconjugants harboring the ethanol production cassette.

S17-1λpir (pLOI3491) and LY151 were mated on LB plates (2% glucose). Pooled exconjugants were inoculated into 1-liter bottles, filled to the brim with NBS mineral salts medium (5% xylose, 100 mM MOPS, pH 7.4) and incubated at 37° C. (150 rpm). Growth was clearly evident after three days of incubation, at which time serial transfers were initiated at 48 hr intervals in 15-ml screw-capped culture tubes (0.1 ml inoculum), followed by serial transfers (MOPS omitted) in small pH-controlled fermentation vessels (33 mg dcw l$^{-1}$ inoculum).

During the course of this work, supplementing with betaine was discovered to be beneficial for xylose fermentation by KO11 (Underwood et al. 2004) and was included as a supplement after the initial 10 transfers. With betaine (1 mM), cultures were transferred at 24 hr intervals due to more rapid growth. Cell yield and ethanol production improved steadily throughout this enrichment process, which consisted of 38 transfers.

Colonies were isolated from the last transfer. All were sensitive to ampicillin, confirming the absence of vector, resistant to apramycin (confirming interrupted ldhA gene in the recipient), and resistant to kanamycin (present in ethanol cassette). Six clones were tested for performance in small fermentations and all were very similar. Two clones were selected and designated LY158 and LY159.

Recombinase was used to remove both antibiotic markers simultaneously. Greater than 99% of the resulting clones from LY158 and LY159 were inhibited by both kanamycin and apramycin. Ten clones from each were pooled and used to inoculate small fermentation vessels for further growth-based selection. After 7 serial transfers at 24-h intervals in NBS-9% xylose medium (1 mM betaine), 12 clones were isolated and tested individually in small fermentations. All were similar and two were chosen, designated LY161 and LY160. A further set of 32 serial transfers (24-h intervals) with LY160 showed continuing improvements in performance. One clone was isolated from the last transfer and designated LY160im.

EXAMPLE 4

Integration Site of Ethanol Genes in E. coli Strain LY160im

A gene library was constructed in pUC18 using EcoRI-digested DNA from strain LY160im and screened for red colonies on aldehyde indicator plates to identify a fragment containing the integrated Z. mobilis genes. One plasmid, containing a 10.2 kb insert (pLOI3951), was selected for subcloning and partial sequencing. Sequencing revealed that the pdc-adhA-adhB-FRT cassette was integrated within the highly expressed rrnB gene (23S ribosomal RNA), concurrent with the direction of transcription (as shown in FIG. 1D). Primers, shown in Table 2, were designed that verified the site of insertion.

EXAMPLE 5

Deletion of casAB

During the course of selections on xylose-NBS mineral salts media and construction of LY160 and LY161, cellobiose utilization ability declined although the Klebsiella oxytoca casAB genes remained integrated in the lac operon (Zhou et al. 2005). As shown in FIG. 1E, plasmid pLOI3924 was constructed to delete these poorly functioning genes by homologous recombination.

Both lacA and lacY were amplified separately by PCR using the primers shown in Table 2, and using KO11 DNA as a template and cloned into pCR2.1-TOPO. Plasmid pLOI3924 was constructed in three consecutive steps: 1) ligating the cloned lacA fragment (BamHI to NotI; 644 bp) into corresponding sites in pLOI3470; 2) ligating lacY (XhoI to Klenow-treated BamHI; 1,292 bp) into XhoI and Klenow-treated Eco0109I sites; and 3) inserting the SmaI fragment (FRT-kan-FRT; 1,228 bp) from pLOI2511 into Klenow-treated BamHI and NdeI (within lacY) sites. The resulting plasmid contains a PacI-flanked lacY-FRT-kan-FRT-lacA cassette (2,984 bp), which was used to replace the casAB genes in LY160im by homologous recombination. After deletion of kan with recombinase, the resulting strain was designated LY163.

EXAMPLE 6

Addition of Esterase

Previous studies have demonstrated low levels of ethyl acetate in distillate from KO11; this problem that was remedied by functionally integrating the estZ gene encoding a short chain esterase from Pseudomonas putida NRRL B-18435 (Hasona et al. 2002). To minimize potential damage to LY163, we constructed a new plasmid to facilitate promoter selection and allow integration of estZ into the partially deleted adhE gene. Promoterless adhE (2,715 bp) and estZ (1,083 bp) genes were amplified using the primers shown in Table 2, and using NC3 DNA and pAH181, respectively, as templates and cloned into pCR2.1-TOPO. The central region of adhE (BglII to Klenow-treated-SalI; 1,408 bp) was replaced with a BglII to Klenow-treated-EcoRI fragment (1,083 bp) containing estZ (ribosomal binding site, coding region and terminator region). The resulting adhE'-estZ-adhE' cassette (Klenow-treated NotI to BamHI fragment; 2,471 bp) was ligated into the Klenow-treated HindIII (blunt) to BamHI region (204 bp) of pLOI3470. A SmaI fragment (1,956 bp) from pLOI3421 containing an FRT-flanked aac gene was inserted into the Klenow-treated HindIII site. After digestion with PacI, the adhE'-estZ-FRT-aac-FRT-adhE' cassette (4,484 bp) was moved into the PacI site of pLOI3918. The resulting plasmid, pLOI3920 (FIG. 1F), contains a unique BglII site for insertion of a promoter fragments upstream from the estZ ribosomal binding site and a temperature-sensitive pSC101 replicon.

Sau3A-digested chromosomal DNA from Z. mobilis was ligated into the BclI site of pLOI3920 and screened for promoter (esterase) activity in strain NC3. Two plasmids were selected from 300 positive clones, and designated pLOI3925A and pLOI3925C. PacI fragments containing the functional esterase cassettes (adhE'-Zm promoter-estZ-FRT-aac-FRT-adhE') were integrated into LY163 with selection for apramycin resistance. After deletion of aac with recombinase, resulting strains were designated LY165A and LY165C, respectively.

EXAMPLE 7

Deletion of mgsA

The Methylglyoxal Bypass is a potential source of lactate in E. coli (Zhu et al. 2001). To eliminate this unwanted product, mgsA encoding methylglyoxal synthase, the first committed-step, was deleted. The mgsA gene was amplified using the primers shown in Table 2 (SEQ ID NO:9 and SEQ ID NO:10), with NC3 genomic DNA as a template, and then cloned into pCR2.1-TOPO. A central BstEII to AgeI (Klenow treated) fragment (66 bp) was replaced with a blunt SmaI to EcoRI (Klenow-treated) fragment (1,942 bp) from pLOI3421 carrying the FRT-flanked aac gene to produce pLOI3940. The mgsA'-FRT-aac-FRT-mgsA' cassette (2,456 bp) was amplified with the primers used for cloning (FIG. 1G) and integrated into LY165C. After removal of aac with recombinase, the resulting strain was designated LY168.

EXAMPLE 8

Fermentation of Xylose in Mineral Salts Medium

Figure 3:
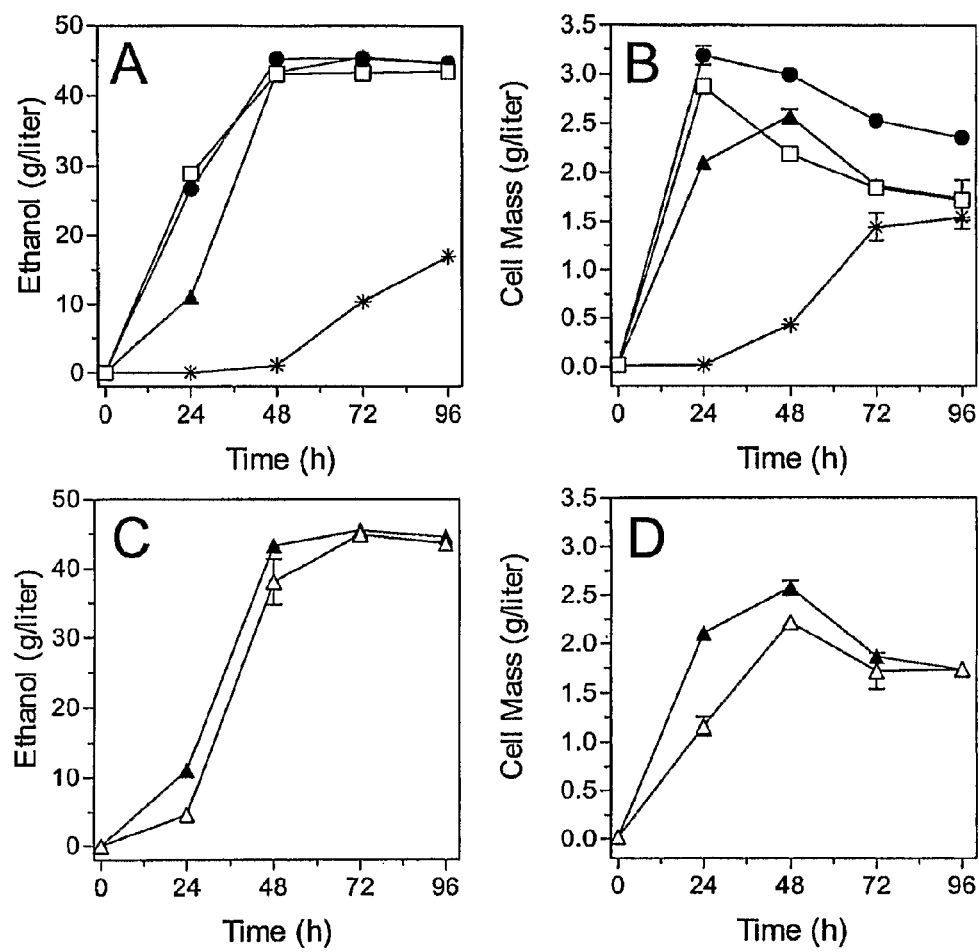
FIG. 3 (A-D) are graphs illustrating fermentation of 9 (w/v) % xylose by recombinant E. coli. Panels A and B show the effect of media composition (Luria broth and NBS mineral salts medium+1 mM betaine). Panels C and D show the effect of methylglyoxal synthase mutation (NBS mineral salts+1 mM betaine). Symbols for all: (*), KO11, grown in NBS medium; (□), KO11, grown in Luria broth; (▲), LY168, grown in NBS medium; (●), LY168, grown in Luria broth; (Δ), LY165, grown in NBS medium.
Figure 4:
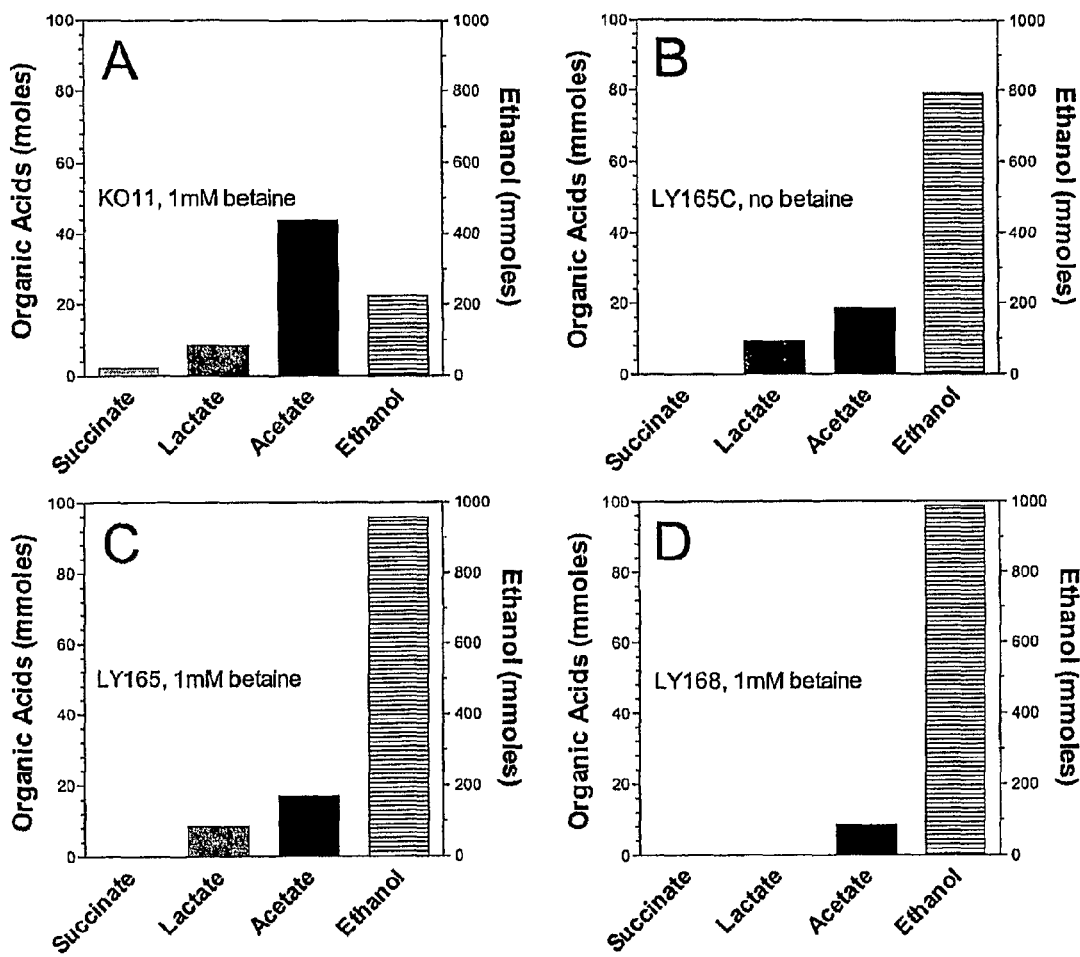
FIG. 4 (A-D) are graphs showing products of xylose fermentation in NBS mineral salts medium containing 9 (w/v) % xylose. Panel A. strain KO11, 1 mM betaine added; Panel B. strain LY165, without betaine; Panel C. strain LY165, 1 mM betaine; Panel D. strain LY168, 1 mM betaine.

As demonstrated in the graphs shown in FIGS. 2 and 3, strains LY161 and LY165C, which contained a complete set of the ethanol genes from Z. mobilis, fermented 9% xylose far more effectively in NBS mineral salts medium than KO11 with and without 1 mM betaine. However, low levels of lactate and acetate remained as co-products, as shown in FIG. 4.

The source of this lactate was the Methylglyoxal Bypass, as demonstrated by the finding that this problem was remedied by deletion of methylglyoxal synthase (mgsA). In strain LY168, lactate levels were below detection. Ethanol yield based on total xylose added to the fermentation was 0.5 g ethanol $g^{-1}$ xylose, which is near the theoretical maximum. Elimination of methylglyoxal synthase also improved growth and cell yield, and reduced the time required to complete xylose fermentation (FIG. 4). With a low starting inoculum, volumetric productivity for ethanol was highest for LY165 and LY168 during the second 24 h of fermentation (approximately 1.3 g l$^{-1}$ h$^{-1}$). After 24 h, fermentations with NBS mineral salts medium (1 mM betaine) were equivalent to those in Luria broth.

EXAMPLE 9

Fermentation in AM1 Medium

Figure 5:
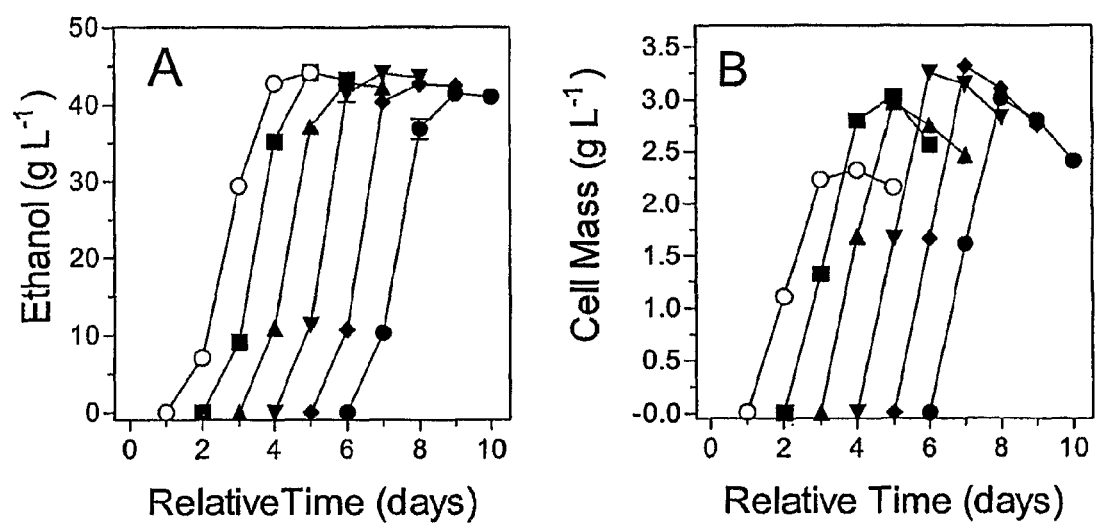
FIGS. 5 (A and B) are graphs demonstrating growth-based selection for strain improvement. LY168 was serially transferred 29 times at 24-h intervals and inoculum of 10 mg dry cell weight (dcw) $l^{-1}$ in AM1 medium (9% xylose) as a growth-based selection for ethanol productivity. Strain LY168im was isolated from the final transfer. Transfers were grouped and averaged: (○), transfers 1-5; (■), transfers 6-10; (▲), transfers 11-15; (▼), transfers 15-20; (♦), transfers 20-25; (●), transfers 26-29; Panel A. Y-axis indicates ethanol produced (g/liter). Panel B. Y-axis indicates cell mass.

A further set of 29 serial Fleaker transfers (24-h intervals) with LY168 in AM1 medium plus 9% xylose (Martinez et al., 2007), a new medium, was conducted (FIGS. 5A and B). Succinate began to appear in the fermentation broth around transfer 21, indicating that the frd operon has been repaired. One clone was isolated from the last transfer and designated LY168im (improved growth in AM1 medium) to be used for further modifications.

EXAMPLE 10

Repair of the lac Region

When the casAB genes were deleted a portion of the lacY gene was also deleted, eliminating the ability of the strain to ferment lactose. In order to repair the region, the primer pair lacZ-cynX was used (Table 2, above) to clone the *E. coli* genomic DNA fragment spanning the region from lacZ to cynX (4,082 bp) using PCR (FIG. 1H). This lacZ-cynX region was integrated into strain LY168im. Selection for homologous recombination of the cassette into the region was conducted in standing screw capped tubes containing AM1 medium and 5% lactose. Colonies were screened with PCR using the primer pair for lacY' (Table 2) was used to verify the repair of the lac operon. PCR screening of 22 colonies that were positive for fermentation of lactose on MacConkey agar plates (containing 2% lactose) indicated that 20 colonies had repaired the region. One colony was as selected and designated strain LY169.

EXAMPLE 11

Deletion of frd Operon and Re-Integration of celY

A problem was encountered during serial transfers of strain LY168im in Fleakers containing AM1 medium with 9% xylose. The fermentation broth began to accumulate succinate, leading to the thought that the strain was able to repair the point mutation originally made in the frdBC region. The celY gene from *Erwinia chrysanthemi* 3937 had previously been integrated in front of the frdA gene (Zhou et al., 2005). An approach was to delete the frdB gene completely and partially delete the frdC gene, keeping the celY gene in front of frdA.

The frdB'-frdC' fragment (948 bp) was cloned from genomic *E. coli* W using the primer pair frdB'-frdC' (Table 2) and ligated into pCR2.1-TOPO, creating pLOI3958.

The next step was to move the cat-sacB cassette into the middle of the genes using PCR, giving the chloramphenicol marker. Using pEL04 (Lee et al., 2001; Thomason et al., 2005; FIG. 1I) as template and the primer pair JmcatsacBN-heI (Table 2), the cat-sacB fragment (3,247 bp) was cloned, flanked by NheI sites. The fragment was ligated into the NheI sites of the PCR product from pLOI3958 using the primer pair NhefrdB-C (Table 2) and pLOI3958 as template, creating pLOI3959 (frdB'-cat-sacB-frdC'). The 'frdB'-cat-sacB-frdC' cassette (3,601 bp) was amplified with the primers used for cloning the original fragment and integrated into LY169, using chloramphenicol for selection. Thirty-nine colonies were selected for screening with PCR to verify integration into the correct region, of which 20 were correct. One colony was selected and was designated LY170.

Next, a plasmid was needed containing frdA'-*Z. mobilis* fragment-celY-frdC'. Plasmid pLOI3959 was digested with NheI and XhoI and ligated to the similarly digested PCR product from pLOI2726 (XhofrdA-NhecelY primer pair; Table 2) with the frdA'-Zm frg-celY cassette as template (Zhou et al., 2005), creating plasmid pLOI3961 (frdA'-Zm frg-celY-frdC'; FIG. 1J). Activity of the celY gene was verified on CMC agar plates. The frdA'-Zm frg-celY-'frdC' cassette (3,157 bp) was amplified with primers XhofrdA and frdC' (Table 2) and integrated into LY170. Of the 225 colonies screened for activity on CMC plates for celY activity and on LB plus chloramphenicol for loss of the marker, eleven were selected for PCR screening to verify the integration into the region. All eleven colonies were correct, and one was designated strain LY172.

Figure 6:
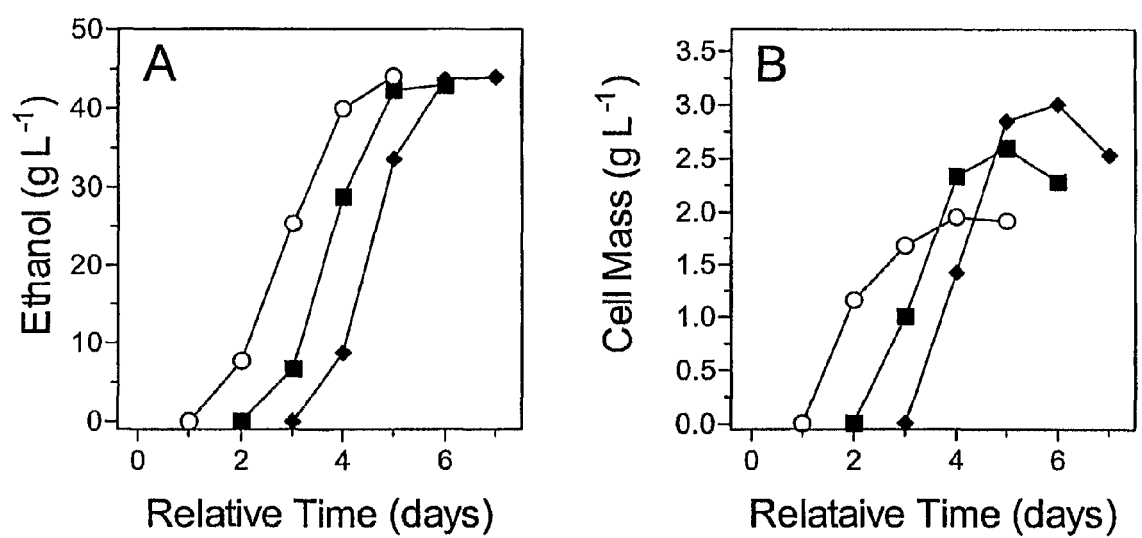
FIGS. 6 (A and B) are graphs demonstrating growth-based selection for strain improvement. LY172 was serially transferred 15 times at 24-h intervals and inoculum of 10 mg dcw $l^{-1}$ in AM1 medium (9% xylose) as a growth-based selection for ethanol productivity. Strain LY172im was isolated from the final transfer. Transfers were grouped and averaged: (○), transfers 1-5; (■), transfers 6-10; (♦), transfers 11-15; Panel A, Y-axis indicates ethanol produced (g/liter). Panel B. Y-axis indicates cell mass.

A further set of 15 serial Fleaker transfers (24-h intervals) with LY172 in AM1 medium plus 9% xylose was conducted (FIGS. 6A and B). One clone was isolated from the last transfer and designated LY172im.

EXAMPLE 12

Integrations of casAB Genes from *Klebsiella oxytoca*

It was still desirable to have the *Klebsiella oxytoca* M5A1 casAcasB genes integrated into strain so it was decided to integrate the genes into the already partially deleted ldhA gene instead of the lac operon (keeping the ability to ferment lactose intact). After cloning the promoterless ldhA gene into pCR2.1-TOPO using primers listed in Table 2 the gene was moved with BamHI-XhoI into same sites of pLOI3470, creating pLOI3971 (PacI sites flanking the gene). The casAcasB genes with the native ribosomal binding site from pLOI1910 (Moniruzzaman et al., 1997) was carried in AM1 medium, 5% cellobiose for 1½ weeks with daily transfers in screw capped tubes. Using PCR the casAB genes (3,406 bp) were cloned with the primer pair BglIIcasA-MfeIcasB and cloned into the PCR product of vector pLOI3971 with the primer pair BglIIldhA-ldhA (Table 2) after digestion with BglII, and MfeI (native MfeI sites in ldhA) making pLOI3972 (ldhA'-casA-casB-ldhA'). Colonies were tested on MacConkey agar with 2% cellobiose to verify fermentation of cellobiose. The next step was to insert the cat-sacB gene cassette behind the casA gene, giving a chloramphenicol and inability to grow on sucrose as the selectable markers.

Using plasmid pLOI4162 the PacI fragment (modified cat-sacB cassette in pUC19 with PacI sites flanking cassette; 2,960 bp; FIG. 1K) was ligated into the pLOI3972 BglII site, creating pLOI3973 (ldhA'-cat-sacB-casA-casB-ldhA'-flanked by NotI sites). The NotI fragment (7,077 bp) carrying the cassette from pLOI3973 was integrated into LY172im with selection on chloramphenicol. Integration was verified with PCR. The new strain was designated LY173.

Using plasmid pLOI3972 the ldhA-casA-casB-ldhA cassette (4,161 bp) was ligated as a PacI fragment into the pLOI3918 PacI site, creating pLOI3975. There is a unique BglII site in pLOI3975 just behind the ribosomal binding site for casA in which *Z. mobilis* CP4 Sau3A genomic DNA fragments were ligated. Colonies were screened on MacConkey agar with 2% cellobiose for varying degrees of red color indicating expression of the casAB genes. Plasmids from the 15 colonies that were positive on the plates were isolated and designated pLOI3976A-K (ldhA'-Zm frg-casA-casB-ldhA) and compared for activity in LY173. Plasmids pLOI3976A, C, D, E and F (as shown in FIG. 1L) were selected for further work. The 4 ldhA'-Zm frg-casA' fragments (NotI/NcoI-internal site in casA) were integrated into LY173 with selection in AM1 medium plus 5% cellobiose standing liquid cultures, serially transferred at 37° C. for 5 days. The resulting strains LY178A, C, D, E and F (respectively) were compared for growth and ethanol production in AM1 medium containing 5% xylose or cellobiose in 10 mL standing liquid cultures. Strain LY178E produced the most ethanol, grew to the highest O.D.550, and looked the best in a comparison on MacConkey agar with 2% cellobiose.

Figure 7:
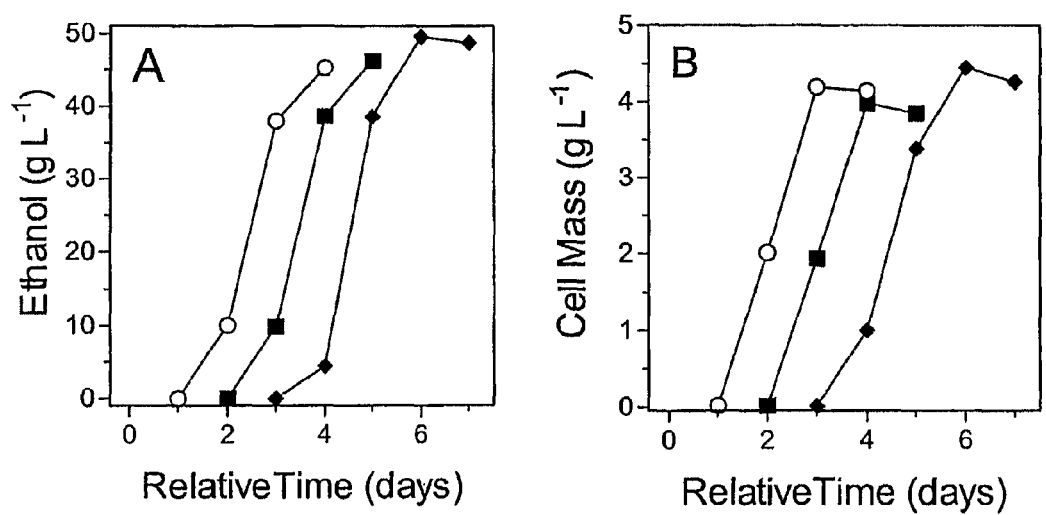
FIGS. 7(A and B) are graphs demonstrating growth-based selection for strain improvement. LY178E was serially transferred 12 times at 24-h intervals and inoculum of 10 mg dcw $l^{-1}$ in AM1 medium (10% xylose) as a growth-based selection for ethanol productivity. Strain LY180 was isolated from the final transfer. Transfers were grouped and averaged: (○), transfers 1-5; (■), transfers 6-10; (♦), transfers 11-12; Panel A. Y-axis indicates ethanol produced (g/liter). Panel B. Y-axis indicates cell mass.
Figure 8:
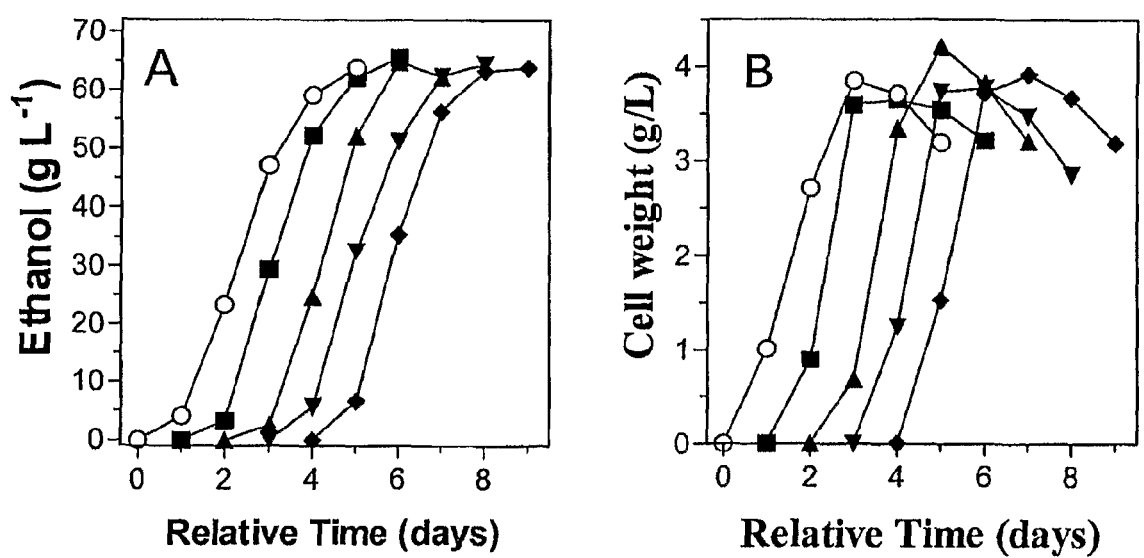
FIGS. 8 (A and B) are graphs demonstrating growth-based selection for strain improvement. LY180 was serially transferred 25 times at 24-h intervals and inoculum of 10 mg dcw $l^{-1}$ in AM1 medium (14% xylose) as a growth-based selection for ethanol productivity. Strain LY186 was isolated from the final transfer. Transfers were grouped and averaged: (○), transfers 1-5; (■), transfers 6-10; (▲), transfers 11-15; (▼), transfers 15-20; (♦), transfers 20-25; Panel A. Y-axis indicates ethanol produced (g/liter). Panel B. Y-axis indicates cell mass.

A further set of 12 serial Fleaker transfers (24-h intervals) with LY178E in AM1 medium plus 10% xylose was conducted. Serial transfers in Fleakers were conducted for 4 consecutive days, alternating with 3 days of transfers in 10 mL liquid cultures in AM1 medium supplemented with 5% cellobiose to improve selection for stable the casAB genes (FIGS. 7A and B, only Fleakers shown). One clone was isolated from the last transfer and designated LY180. A further set of 25 serial Fleaker transfers (24-h intervals) with LY180 in AM1 medium plus 10% xylose was conducted. Serial transfers in Fleakers were conducted for 4 consecutive days, alternating with 3 days of transfers in 10 mL liquid cultures in AM1 medium supplemented with 10% cellobiose (FIGS. 8A and B, only Fleakers shown). One clone was isolated from the last transfer and designated LY186.

EXAMPLE 13

Improved Ethanologenic Recombinant Bacteria

The foregoing studies demonstrate that there are no inherent barriers to rapid and efficient fermentation of xylose by recombinant *E. coli* in mineral salts medium. The improvements observed over previously engineered strains result from a combination of several factors, one of which is random integration with growth based-selection to determine an optimal site for chromosomal integration of the *Z. mobilis* genes for ethanol production. Another factor is deletion of antibiotic genes which may retard performance. A final factor is elimination of the Methylglyoxal Bypass, a spillover pathway that slows glycolysis and macromolecular synthesis (Zhu et al. 2001).

It was observed that the addition of betaine increased growth and improved performance but was not essential. Betaine is a protective osmolyte that improves growth in the presence of initial high sugar concentrations, reducing the biosynthetic demands for glutamate and trehalose (Underwood et al. 2004; Zhou et al. 2006a and 2006b).

EXAMPLE 14

Engineering of BW34

The utility of co-production of bacterial endoglucanases in reducing the requirement for commercial cellulases has been previously demonstrated (Wood and Ingram, 1992; Wood, 1997; Wood et al. 1997b). The most effective of these were found to be those from *Erwinia chrysanthemi* (Wood et al. 1997b, Zhou et al. 2001). The combination of CelY and CelZ, working synergistically, allowed for the direct conversion of amorphous cellulose to ethanol (Zhou and Ingram, 2001). CelY alone, was shown to provide the greatest benefit when used in conjunction with commercial cellulose preparations (Zhou et al. 2001) in the simultaneous saccharification and fermentation (SSF) of crystalline cellulose.

Strains and plasmids used in the studies described herein are listed in Table 3, below.

TABLE 3

| Strain/Plasmid | Relevant traits | Source/Reference |
|---|---|---|
| *E. coli* DH5α | lacZΔM15 recA | Bathesda Research Labs |
| *E. coli* S17 | λ pir | Lab Stocks |
| *K. oxytoca* SZ21 | (Z.m pdc.adhB), cat, Er.c. celYcelZ) | Zhou et al. 2001 |
| *K. oxytoca* SZ22 | SZ21 ΔcelZ.aac | Zhou et al. 2001 |
| *K. oxytoca* BW15 | *K. oxytoca* M5a1 budAB::FRT-tet-FRT | This study (Chapter 2) |
| *K. oxytoca* BW21 | (Z.m pdc.adhB), cat, ΔbudAB | This study (Chapter 2) |
| *K. oxytoca* BW32 | BW21, celY, kan | This study |
| *K. oxytoca* BW33 | SZ21 ΔbudAB, tet | This study |
| *K. oxytoca* BW34 | BW21, celY | This study |
| *K. oxytoca* BW35 | SZ21 ΔbudAB | This study |
| pCPP2006 | rpm. –40 kbp frag. Containing our genes from *E. chrysanthemi* | He et al. 1991 |
| pFT-A | bla, FLP recombinase | Posafi et al. 1997 |
| pFT-K | kan, FLP recombinase | Posafi et al. 1997 |
| pLOI2224 | R6K ori, kan, FRT flanked MCS (AscI) | Martinez-Morales et al. 1999 |
| pLOI2348 | celY from *E. chrysanthemi* 3 kbp M5a1 chromosomal fragment | Zhou et al. 2001 |
| pLOI3420 | λ Red Recombinase, RepA ori, aac | This study |
| pLOI3421 | FRT-aac-FRT | This study |
| pLOI3290 | DraI aac frag. from pLOI3421 in pFT-A ClaI | This study |
| pLOI3293 | celY, M5a1glgP frag. (AscI) from pLOI2348 in pLOI2224 AscI | This study |

Strains were maintained on Luria agar plates without added sugar. Antibiotics were added for selection as follows: ampicillin, 50 mg/L; apramycin, 50 mg/L; kanamycin, 50 mg/L; tetracycline, 12.5 mg/L; and spectinomycin, 50 mg/L. Ethanol producing strains were maintained on Luria agar plates which also contained 2% glucose and 40 or 600 mg/L chloramphenicol (alternating daily, under argon). Agar plates used in the screening of endoglucanase production also contained 3 g/L low-viscosity carboxymethylcellulose (CMC). CMC plates were stained with Congo red (Wood et al. 1988) after overnight growth at 37° C. Strains containing pLOI3420 were incubated at 30° C., all others were maintained at 37° C.

Standard methods known in the art were used for PCR-based gene cloning, plasmid constructions, and genetic analyses. Methods for integration, chromosomal deletions, integration, and the use of removable antibiotic resistance genes have been previously described (Datsenko and Wanner, 2000; Martinez-Morales et al. 1999; Zhou et al. 2003; Causey et al. 2004). *Escherichia coli* DH5" was used for most constructions. *Escherichia coli* S17 was used for the construction of plasmids containing an R6K origin of replication. Phage P1 was used for generalized transduction according to the methods described by Silhavay et al. (1984).

The plasmid used for direct integration of the gene celY encoding the endoglucanase CelY from *E. chrysanthemi* was constructed by removing a 5.7 kbp AscI fragment from pLOI2348 containing celY, behind a surrogate promoter, and a chromosomal fragment from *K. oxytoca* M5a1 to target integration (previously determined to contain glgP, a gene in the glycogen synthesis pathway) (Zhou et al. 2001) followed by ligation in the AscI site of pLOI2224 (Martinez-Morales et al. 1999) to create pLOI3293. Integration of pLOI3293 in the budAB strain *K. oxytoca* BW21 was facilitated by the expression of λ Red Recombinase from pLOI3420. Resultant integrants were cured of pLOI3420 by outgrowth at 39° C., selected for kanamycin resistance and subsequently screened for endoglucanase production and retention of resistance to high-level chloramphenicol resistance (600 mg/L). Several isolates were further tested for ethanol production in pH controlled fermentations in OUM1 (not shown, Wood 2005) containing 90 g/L glucose, and all were found to be similar. One was selected for further study and designated strain BW32.

Strains containing two endoglucanase genes from *E. chrysanthemi*, celYcelZ, and budAB were constructed as follows.

at 35° C. (150 rpm). In fermentations with strain BW35 pCPP2006, spectinomycin was added for plasmid maintenance. All other fermentations contained no added antibiotics. Broth of glucose fermentations and SSFs were maintained at pH 5.2 by the automatic addition of 2N KOH. For improved xylose fermentation, SSCFs were maintained at pH 5.8.

To compare the fermentation performance of strains expressing recombinant endoglucanase(s), final strains were used in the fermentation of 90 g/L glucose in OUM1. The CelY producing strain BW34 was equivalent to strain BW21 in both growth and ethanol production (FIG. 9). The strain expressing CelY and CelZ, BW35, included the co-expression of the *E. chrysanthemi* out genes from pCPP2006 for improved growth. Strain BW35 pCPP2006 initially had ethanol productivity similar to both BW21 and BW34. Final ethanol concentrations were reduced in strain BW35, possibly due to instability of pCPP2006. Maximum ethanol yields from 90 g/L glucose were 92.7, 91.4, and 80.5% of theoretical by strains BW21, BW34, and BW35 pCPP2006, respectively. When by-products were analyzed (Table 4, below) strains BW21 and BW34 were again similar while strain BW35 had a slight increase in lactate production.

Table 4 shows product formation and carbon balance after 72 h from 90 g/L glucose in OUM1 by budAB, ethanologenic, endoglucanase producing strains of *K. oxytoca*.

TABLE 4

| Strain | | Glucose (mM) | Lactate (mM) | Succinate (mM) | Acetate (mM) | Acetoin + Butanediol (mM) | Ethanol (mM) | Carbon Balance (%) |
|---|---|---|---|---|---|---|---|---|
| BW21 | 4 | 29 ± 21 | 4 ± 1 | 13 ± 3 | 5 ± 1 | 2 ± 1 | 926 ± 17 | 100 ± 2 |
| BW34 | 4 | 25 ± 10 | 7 ± 3 | 14 ± 1 | 7 ± 1 | 2 ± 0 | 917 ± 32 | 91 ± 1 |
| BW35 | 3 | 94 ± 12 | 17 ± 8 | 12 ± 2 | 0 ± 0 | 1 ± 1 | 833 ± 24 | 100 ± 3 |
| BW35 pCPP2006 | 3 | 88 ± 26 | 18 ± 3 | 15 ± 1 | 20 ± 3 | 0 ± 1 | 788 ± 46 | 98 ± 1 |

Briefly, *K. oxytoca* strain BW15 was used as a donor strain for the P1 phage transduction of a deletion in the butanediol operon (budA'-FRT-tet-FRT-tudB') to strain SZ21 (Zhou et al. 2001). Isolation and screening of transductants were identical to those used above, except tetracycline was used for selection. Strain BW33 was carried on for further work.

To facilitate the removal of kan from strain BW32, pFT-A (FLP recombinase) was modified by the addition of an apramycin resistance gene, aac. Plasmid pFT-A was linearized by restriction digestion with ClaI, followed by treatment with the Klenow fragment of *E. coli* DNA polymerase. A 1.6 kbp fragment containing aac from pLOI3420 was ligated to the linearized pFT-A creating pLOI3290. Removal of tet from strain BW33 used the previously described pFT-K (Posafi et al. 1997). Kans and Tets strains were re-screened as above for endoglucanase production, chloramphenicol resistance, and ethanol production, and the resulting strains were designated BW34 and BW35 respectively. Integrations were also confirmed using PCR.

Seed cultures (150 ml in 250 ml flasks) were grown for 16 h at 35° C. (120 rpm) in the same media used in pH controlled fermentations but contained 50 g/L glucose. Cells were harvested by centrifugation (5000×g, 5 min) and used as inocula to provide an initial concentration of 33 mg/L dry cell weight (OD550 nm=0.1). Fermentation vessels were previously described (Beall et al. 1991) and contained an initial volume of 350 ml. Glucose fermentations contained 90 g/L sugar and were in OUM1 (Wood 2005). SSFs contained 100 g/L Sigmacell 50 in Luria broth and SSCFs contained 45 g/L Sigmacell 50 plus 40 g/L xylose in OUM1. Cultures were incubated The increased lactate production was retained with BW35 pCPP2006. The production of acetate is common in strains expressing high levels of recombinant protein (Aristidou et al. 1995; Farmer and Liao, 1997).

Two commercial cellulase preparations evaluated for their use in combination with CelY (and CelZ). Both Spezyme CE (GENECOR INT, no longer available commercially) and GC220 are standardized based on their activities on carboxymethyl cellulose, and are reported to be blends of hydrolase activities. To eliminate any potential effects by the media, Luria broth was used in evaluating each enzyme blend. The highest ethanol concentrations of 38 g/L (FIG. 10C) were obtained with the highest concentrations of Spezyme CE (100 μL/g Sigmacell). This corresponded to an ethanol yield of 67% of theoretical.

In contrast to previous work with Sigmacell and Spezyme CE, there was no apparent benefit from CelY (BW34 vs. BW21) or CelZ (BW35 pCPP2006 vs. BW21) in combination with Spezyme CE (Zhou et al. 2001). At lower enzyme loadings, the results clearly indicate that Spezyme GC220 is the superior to Spezyme CE (FIGS. 10A and 10C). At equivalent enzyme concentrations (50 μL/g cellulose) the initial rates and final ethanol concentrations were increased by 26% and 21% respectively (with strain BW34) when Spezyme GC220 is used, compared to Spezyme CE. Ethanol production using Spezyme GC220 at an enzyme loading of 50 μL/g Sigmacell was nearly equivalent to that with Spezyme CE at 100 μL/g Sigmacell. With Spezyme GC220 (50 μL/g), the expression of CelY (in strain BW34) appeared to have the most benefit. SSFs (with strain BW34) produced 15% higher final ethanol concentrations than did strain BW21 and 70% higher than strain P2.

Figure 11:
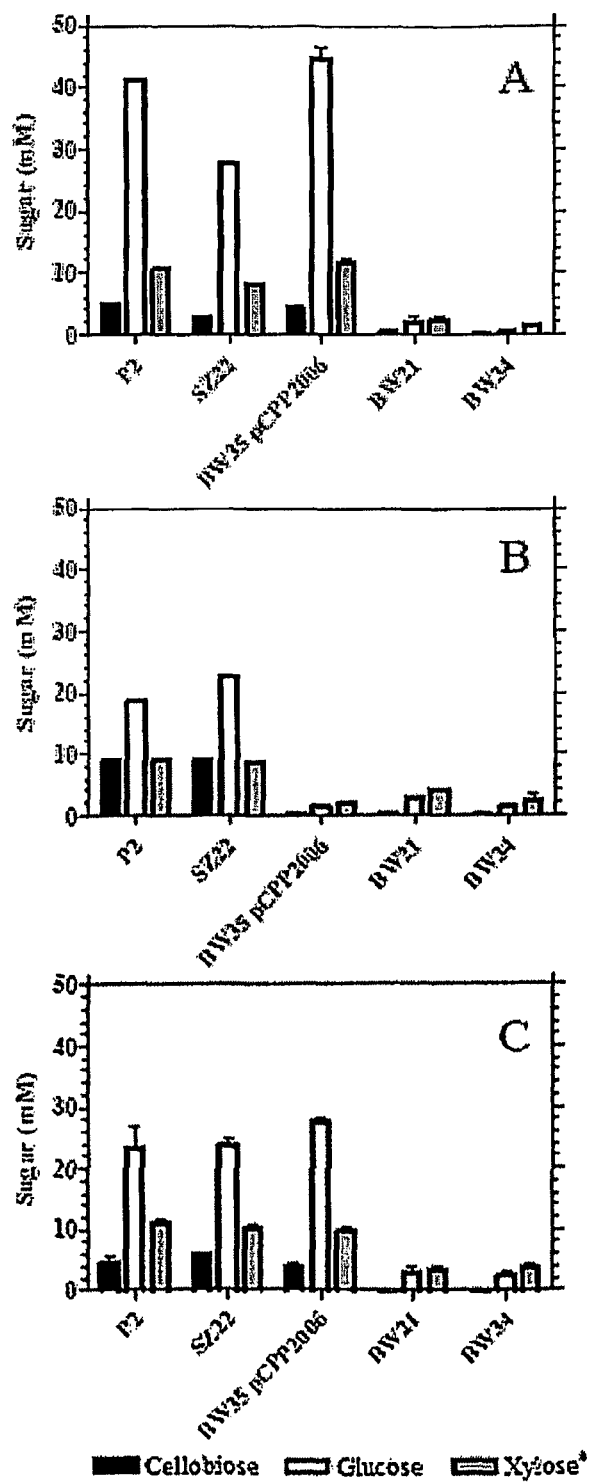
FIG. 11 (A-C) are graphs demonstrating residual sugars (144 h) in SSF of Sigmacell using: (A) 50 µl Spezyme GC220 per g Sigmacell, (B) 50 µl Spezyme CE per g Sigmacell, and (C) 100 µl per g Sigmacell. *Tentatively identified as xylose.

Because the commercial enzymes are blends of activities, it is likely that they are periodically reformulated to meet specific customer requirements and thus are not constant over several years. Also consistent with a change in the formulation of Spezyme CE was the relatively poor performance of the previously developed strain P2 (Doran and Ingram, 1993). The previously developed strain SZ22, expressing CelY (Zhou et al. 2001) was also included for comparison. Using either enzyme (at any loading) the amount of cellulose degradation products (sugar) present at the end of fermentation (FIG. 11) appeared to correlate to the production of ethanol and may reflect the metabolic activity of the organism relative to the effectiveness of the cellulase used. While Sigmacell is reported to be a purified cellulose product, the detection of xylose suggests a small xylan component. Alternatively, the HPLC peak identified as xylose may be another metabolic product from components (preservatives, stabilizers, etc.) present in commercial cellulases. Because of this uncertainty, residual xylose is not included in yield calculations. In SSFs where the hydrolysis is more rapid (50 µl Spezyme GC220 and 100 µl Spezyme CE per g cellulose) the stability of pCPP2006 in strain BW35 may again cause a reduction in final ethanol concentrations.

Figure 12:
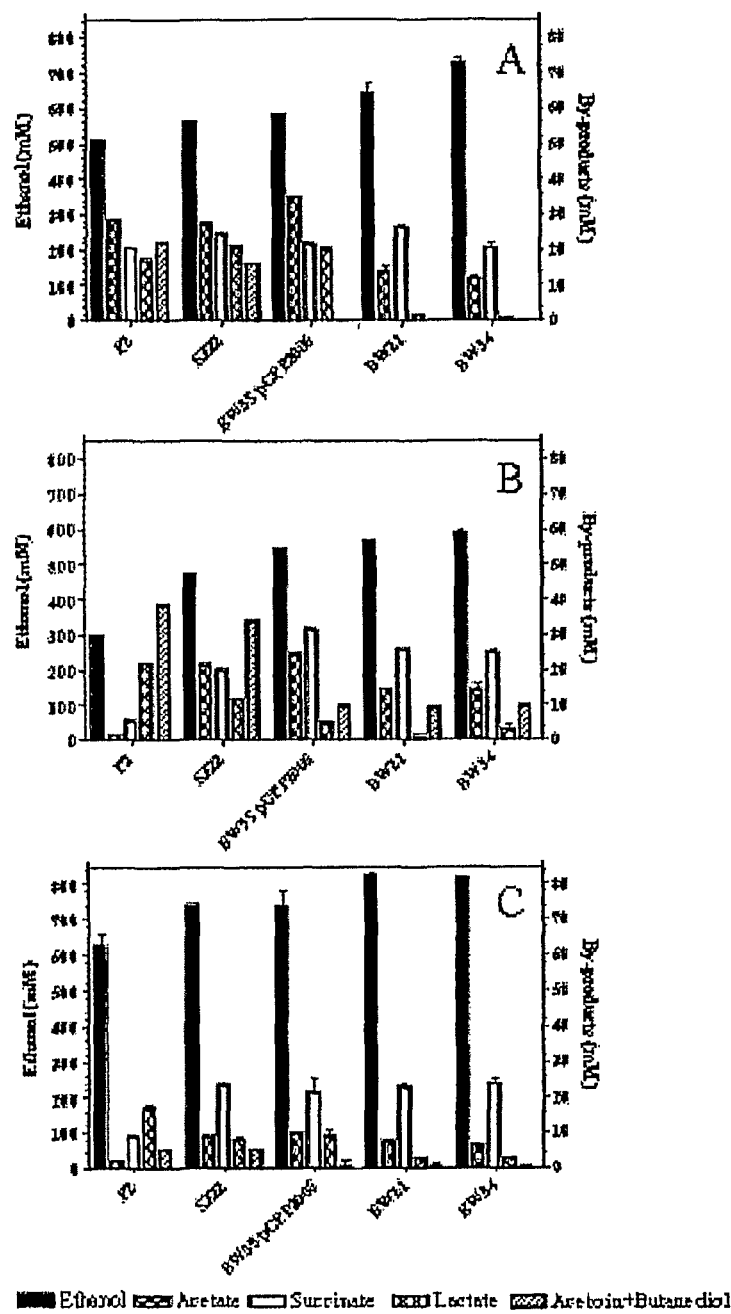
FIG. 12 (A-C) are graphs demonstrating product formation in SSF from 100 g/L Sigmacell (144 h) with (A) 50 µl Spezyme GC220 per g cellulose; (B) 50 µl Spezyme CE per g cellulose; and (C) 100 µl Spezyme CE per g cellulose.

In general, the strains lacking genes of the 2,3-butanediol fermentation pathway (budAB) outperformed those which retain those genes. The elimination of budAB also resulted in the reduction of other by-products as well (FIG. 12). An exception to this was in strain BW35 pCPP2006, as seen in glucose fermentations (shown in Table 4, above) where both acetate and lactate production were elevated. Products of the 2,3-butanediol fermentation pathway, in strains P2 and SZ22, appeared to be correlated to the rate of cellulose hydrolysis, i.e., glucose limitation (50 µl CE>50 µl GC220>100 µl CE per g cellulose), contrary to studies with K aerogenes in glucose limiting chemostat cultures (Teixeira de Mattos and Tempest, 1983). With the exception of strain P2, which performed relatively poorly, succinate levels were consistent among all strains regardless of enzyme type or concentration.

The elimination of need for extensive liquid-solid separation can simplify processing of lignocellulose to ethanol (Wright et al. 1988). The same enzymes (Spezyme CE and Spezyme GC220) used in SSF were again evaluated for their use in SSCFs containing 45 g/L Sigmacell and 40 g/L xylose. An enzyme loading of 50 µl/g cellulose was used for each enzyme. To fully evaluate the potential for commercial application, all SSCFs used OUM1 (Wood 2005), only the budAB strains BW21, BW34, and BW35 pCPP2006 were tested.

Figure 13:
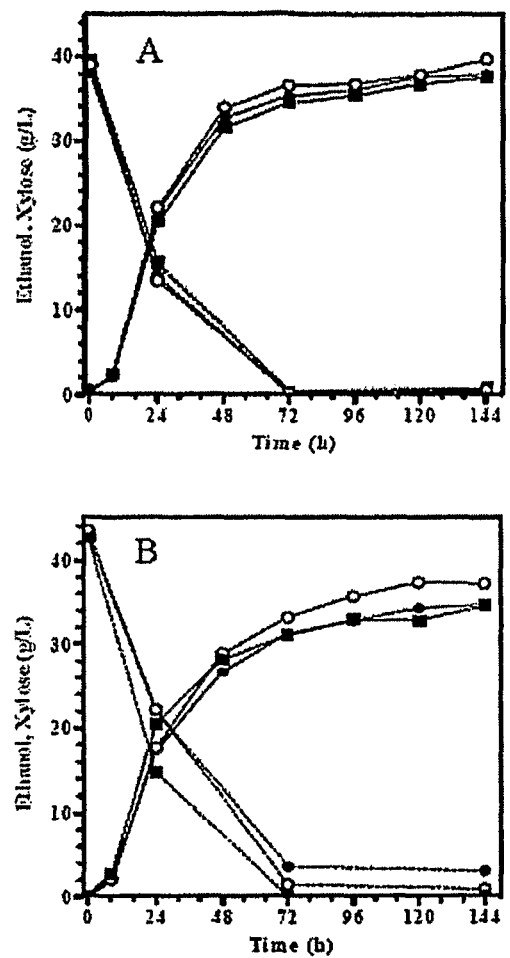
FIGS. 13 (A and B) are graphs demonstrating ethanol production (solid lines) and xylose consumption (dotted lines) in SSCF of 40 g/L xylose and 45 g/L Sigmacell with 50 µL, Spezyme CE per g Sigmacell (A) and 50 µL Spezyme GC220 per g Sigmacell (B) by *K. oxytoca* strains BW21 (■), BW35 pCPP2006 (●), and BW34 (○).

In SSCF it appears that the reduced hydrolysis rates by Spezyme CE are actually beneficial for the rapid and complete use of xylose (FIG. 13). With Spezyme GC220, glucose levels although low (~1 mM at 24 h), may initially exceed a threshold where xylose metabolism becomes repressed. Further evidence of this is found in the reduced rate of xylose consumption in the endoglucanase producing strains BW34 and BW35 pCPP2006, presumably a result of the improved hydrolysis seen in SSFs with Spezyme GC220. The requirement for increased PFL (or ACK) activity (elevated pH) for improved xylose consumption was previously shown (Wood 2005). In OUM1 at pH 6.0, strain BW21 produced 44.3 g/L ethanol from 90 g/L xylose, 96.4% of theoretical yields. A slightly more conservative 95% was assumed for xylose conversion, in cellulose yield calculations, in SSCF at pH 5.8 (Table 5, below).

TABLE 5

| Enzyme | Strain | SSCF Yield (%)[a,b] | | SSF Yield (%)[d,e] |
| --- | --- | --- | --- | --- |
| | | Xylose + Cellulose | Cellulose[c] | |
| Spezyme CE | BW21 | 81.8 | 71.2 | 45.8 |
| | BW35 pCPP2006 | 82.5 | 72.4 | 43.6 |
| | BW54 | 86.6 | 79.8 | 47.0 |
| Spezyme GC220 | BW21 | 75.0 | 58.9 | 51.8 |
| | BW35 pCPP2006 | 75.3 | 59.5 | 37.9 |
| | BW34 | 80.9 | 70.1 | 58.8 |

[a]% of theoretical based on 0.51 g ethanol per g xylose and/or 0.568 g ethanol per g cellulose.
[b]SSCFs were in OUM1 medium, pH 5.8 and yields ignore residual xylose.
[c]Assumes 95% of theoretical ethanol yield (19.4 g/L) from added xylose.
[d]SSFs were in Luria broth, pH 5.2.

Figure 14:
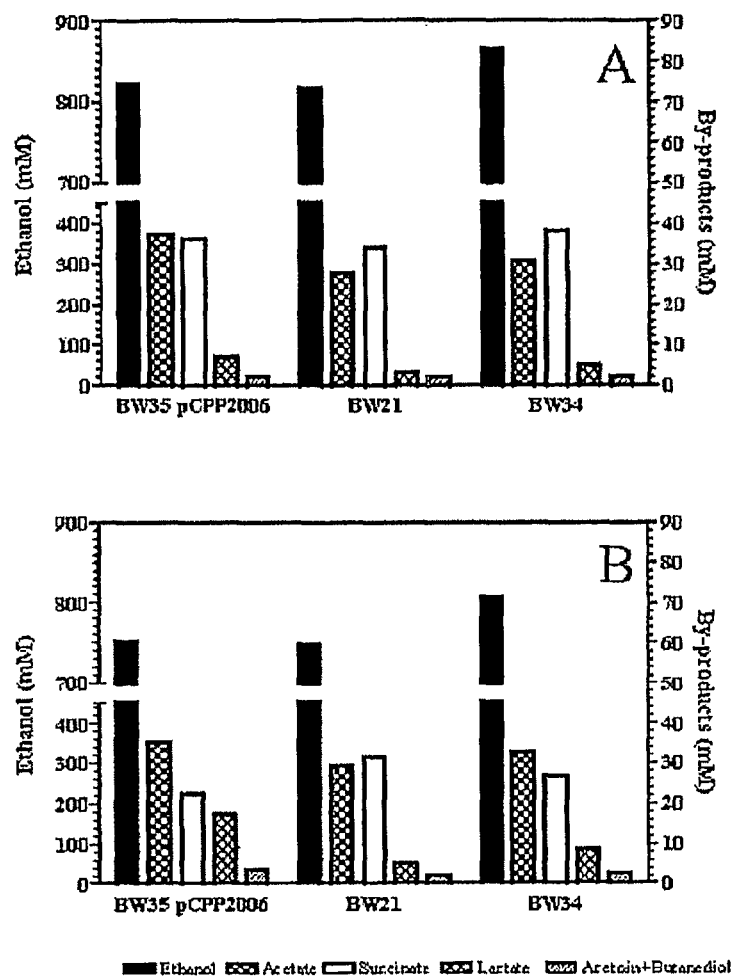
FIGS. 14 (A and B) are graphs demonstrating product formation by ethanologenic, budAB strains of *K. oxytoca* in SSCF of 40 g/L xylose and 45 g/L Sigmacell (144 h) using: (A) 50 µL Spezyme CE per g Sigmacell and (B) 50 µL Spezyme GC220 per g Sigmacell.

As in SSF, the by-products formed were similar between strains in SSCF (FIG. 14) and mostly consistent with those seen in SSF. The increased ACK (PFL) activity at pH 5.8 did result in an increase in acetate production relative to that seen in glucose or in SSF. The inclusion of xylose in SSCF resulted in improved cellulose conversion.

Figure 15:
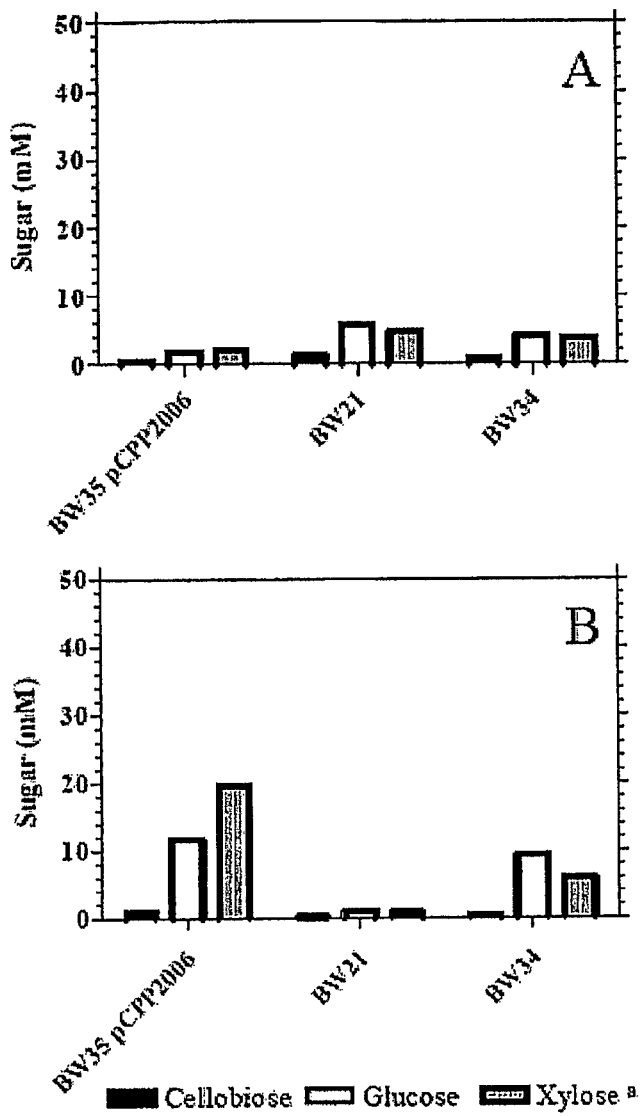
FIGS. 15 (A and B) are graphs demonstrating residual sugar in SSCF of 40 g/L xylose and 45 g/L Sigmacell using: (A) 50 µL Spezyme CE per g Sigmacell and (B) 50 µL Spezyme GC220 per g Sigmacell. *Tentatively identified as xylose.

Table 5 compares ethanol yields from SSF and SSCF (at enzyme loadings of 50 µL/g Sigmacell) by budAB strains. The most significant increases were seen with Spezyme CE where estimated cellulose conversions were >55% higher in SSCF than in SSF alone. Using Spezyme GC220 in SSCF also resulted in increased ethanol yields from cellulose (14 to 19%). With both enzymes, the largest increase was seen in BW34 in either SSF or SSCF. The improved metabolism of cellulose degradation products, in SSCF, was reflected by the low levels of sugar detected at the end of fermentation (FIG. 15). When Spezyme GC220 was used, the reduced rate of xylose use, and overall ethanol productivity, by strains BW34 and BW35 pCPP2006, translated to an increase in residual sugar detected.

Figure 16:
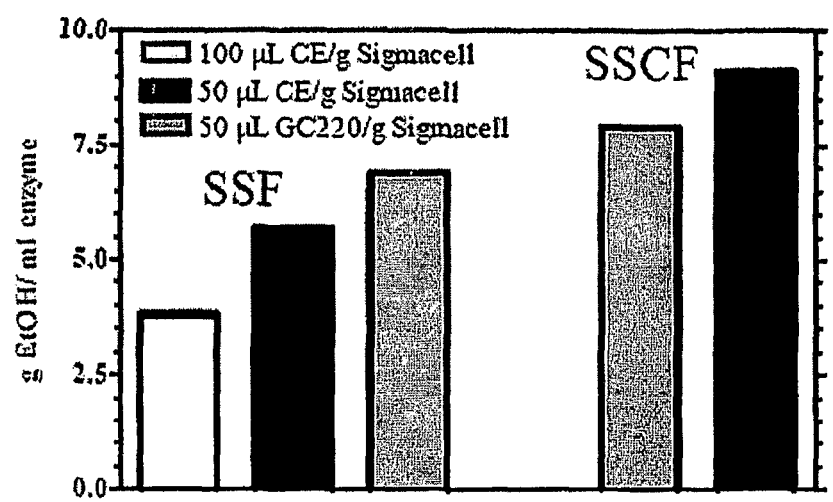
FIG. 16 is a graph demonstrating ethanol production, from cellulose, per unit enzyme in SSF (100 g/L Sigmacell) and SSCF (40 g/L xylose and 45 g/L Sigmacell) by *K. oxytoca* BW34. In SSCF 95% of theoretical yield (19.4 g/L) from added xylose was assumed. Spezyme type and enzyme loadings are indicated.

It is evident that the choice of commercial cellulase can have an impact on the extent of cellulose hydrolysis. The inclusion of xylose, or possibly other free sugars, increased the effectiveness of cellulases used in SSCF. This was likely due to increased biocatalyst concentrations, which were better able to maintain sub-inhibitory concentrations of cellobiose and glucose. When increased biocatalyst concentrations were combined with the production of additional endoglucanase activity, cellulose conversion was even greater, even at fermentation conditions less that optimal for fungal cellulase activity. The incremental improvements in ethanol production from cellulose are illustrated in FIG. 16. The amount of ethanol per unit enzyme has a direct impact on the cost of ethanol production from cellulose using cellulase. In SSF, as Spezyme CE loading decreased 50%, the enzyme cost per gram ethanol would decrease an equivalent 50%. Assuming Spezyme GC220 is equivalent to the cost of Spezyme CE, the use of Spezyme GC220 would reduce enzyme costs by an additional 21%. In SSCF the enzyme cost of ethanol production from cellulose could be reduced further by using Spezyme GC220 (14%) or Spezyme CE (60%) at equivalent enzyme loadings (50 µL/g Sigmacell) used in SSF.

EXAMPLE 15

Eliminating Chloramphenicol Resistance in Ethanologenic KO11-RD1 and BW34

Strains, Plasmids, Media and Growth Conditions
The strains and plasmids used in this study are listed in Table 6, below.

TABLE 6

| Plasmid | |
|---|---|
| pCR2.1-TOPO | |
| pLOI4162 | Bla cat; |
| pLOI4292 | Bla kan; Kan amplified from pCR2.1-TOPO, digested with XhoI and AccI, then cloned into pLOI4162 to replace cat gene |
| Cat deletion (1st round) | |
| pLOI4657 | Bla kan; cat (400 bp fragment, using primer JMcatUP/JMcatDOWN) amplified from KO11-RD1 cloned into pCR2.1-TOPO vector |
| pLOI4658 | Bla; pLOI4657 digested with SfoI and self-ligated to inactivate Kan resistance |
| pLOI4659 | Bla kan; Kan-sacB cassette from pLOI4292 (PacI, T4) cloned into cat in pLOI4658 |
| pLOI4660 | Bla kan; PCR fragment amplified from pLOI4657 (using cat-1/cat-2 primers), kinase treated, and then self-ligation |
| Cat deletion (2nd and 3rd round) | |
| pBR322 | Bla tet; |
| pLOI4661 | Tet; cat (200 bp fragment, using primer cat2-upPstI/cat2-downPstI) amplified from KO11-RD1, digested with PstI and cloned into pBR322 at PstI site |
| pLOI4662 | Bla kan; Kan-sacB cassette from pLOI4292 (PacI, T4) cloned into cat in pLOI4661 |
| pdc-adhA-adhB integrated in E. coli | |
| pLOI2225 | cat, R6K |
| pLOI2394 | bla; deletion of multiple cloning site (KpnI-HindIII) in pLOI2302 |
| pLOI3491 | bla kan; pdc-adhA-adhB-FRT-Kan-FRT |
| pLOI4664 | Bla; pflB amplified from E. coli B (using primer pflB-up-EcoRI/pflB-down-EcoRI), digested with EcoRI and cloned into pLOI2394 at EcoRI site |
| pLOI4665 | Bla kan; pdc-adhA-adhB-FRT-Kan-FRT cassette from pLOI3491 (PacI, blunted by T4 DNA polymerase) cloned into pflB in pLOI4664 |
| pLOI4666 | Kan cat; pflB'-pdc-adhA-adhB-FRT-Kan-FRT-pflB" cassette from pLOI4664 (AscI fragment) cloned into AscI site of pLOI2225 |
| pLOI4670 | Bla; rrlE amplified from E. coli B (using primer rrlE-up-EcoRI/rrlE-down-EcoRI), digested with EcoRI and cloned into pLOI2394 at EcoRI site |
| pLOI4671 | Bla kan; pdc-adhA-adhB-FRT-Kan-FRT cassette from pLOI3491 (PacI, blunted by T4 DNA polymerase) cloned into rrlE in pLOI4670 |
| pLOI4672 | Kan cat; rrlE'-pdc-adhA-adhB-FRT-Kan-FRT-rrlE" cassette from pLOI4671 (AscI fragment) cloned into AscI site of pLOI2225 |
| pdc-adhA-adhB integrated in Klebsiella | |
| pLOI4637 | bla kan; pflB (PCR) from K. oxytoca M5A1 cloned into pCR2.1-TOPO vector |
| pLOI4645 | bla; pflB gene from pLOI4637 (KpnI-XbaI, blunted by T4 DNA polymerase) cloned into pLOI2394 at EcoRI site (blunted by Klenow) |
| pLOI4646 | bla kan; pdc-adhA-adhB-FRT-Kan-FRT cassette from pLOI3491 (PacI, blunted by T4 DNA polymerase) cloned into pflB in pLOI4645 |
| pLOI4649 | kan cat; K.pflB'-pdc-adhA-adhB-FRT-Kan-FRT-K.pflB" cassette from pLOI4646 (AscI fragment) cloned into AscI site of pLOI2225 |
| pLOI4673 | Bla; rrlE amplified from Klebsiella oxytoca M5A1 (using primer K.pflB-up-EcoRI/K.pflB-down-EcoRI), digested with EcoRI and cloned into pLOI2394 at EcoRI site |
| pLOI4674 | Bla kan: pdc-adhA-adhB-FRT-Kan-FRT cassette from pLOI3491 (PacI, blunted by T4 DNA polymerase) cloned into K.rrlE in pLOI4673 |
| pLOI4675 | Kan cat; K.rrlE'-pdc-adhA-adhB-FRT-Kan-FRT-K.rrlE" cassette from pLOI4674 (AscI fragment) cloned into AscI site of pLOI2225 |

KO11-RD1 and BW34 were the original ethanol producing strains, which were resistance to 600 mg l−1 chloramphenicol. The primers used in this study are listed in Table 7, below.

TABLE 7

| Primers | |
|---|---|
| Kan-up | AGCTCGAG AGACTGGGCGGTTTTATGG |
| Kan-down | AGGTATAC GCGACACGGAAATGTTGAAT |
| Cat deletion | |
| JMcatUP | ACGGT GAGCT GGTGA TATGG |
| JMcatDOWN | GCATT CTGCC GACAT GGAAG |
| Cat-1 | TATACGCAAGGCGACAAGGT |
| Cat-2 | TCGTCGTGGTATTCACTCCA |
| Cat2-upPstI | atcctgcagTTTCCGGCAGTTTCTACACA |
| Cat2-downPstI | atcctgcagTTTGCCCATGGTGAAAACG |
| Cat2-3 | CAATCCCTGGGTGAGTTTCA |
| Cat2-4 | GGGAAATAGGCCAGGTTTTC |
| Cat2-up | TTTCCGGCAGTTTCTACACA |
| Cat2-down | TTTGCCCATGGTGAAAACG |
| pdc-adhA-adhB integrated in E. coli at pflB | |
| pflB-up-EcoRI | gcagaattcCCTGGCAAACCTGATGGTAT |
| pflB-down-EcoRI | gcagaattcACTCAGCTTGCAGGATTGCT |
| pflB-up | CCTGGCAAACCTGATGGTAT |
| pflB-down | ACTCAGCTTGCAGGATTGCT |
| pflB-1 | CGTACAATAAAGGCTCCACGA |
| pflB-2 | CACCTACCTTCTTAAGTGGATTTTT |
| pflB-up2 | TGTCCGAGCTTAATGAAAAGTT |
| pflB-down2 | CGAGTAATAACGTCCTGCTGCT |

TABLE 7-continued

| | |
|---|---|
| pflB-3 | GGTTACTTCCACCACGAAGC |
| pflB-4 | GTGAGTGCGGTTTTCCAGTT |
| pflB-5 | AAACGGGTAACACCCCAGAC |
| pflB-6 | CGGAGTGTAAACGTCGAACA |
| pdc-adhA-adhB integrated in *E. coli* at rrlE | |
| rrlE-up-EcoRI | gcagaattcAGCCAGGATGTTGGCTTAGA |
| rrlE-down-EcoRI | gcagaattcAAAGGTTCACGGGGTCTTTC |
| rrlE-up | AGCCAGGATGTTGGCTTAGA |
| rrlE-down | AAAGGTTCACGGGGTCTTTC |
| rrlE-1 | AGCAACAAATGCCCTGCTT |
| rrlE-2 | CACCGTAGTGCCTCGTCAT |
| pdc-adhA-adhB integrated in *Klebsiella* at pflB | |
| pflB-up2 M5A1 | GCCGTAGCCTGATGGATAAA |
| pflB-down2 M5A1 | ACGTCCTGCTGCTGTTCTTT |
| pflB-2 M5A1 | ACTCAGTCCGAGCTGACCAT |
| pflB-3 M5A1 | TCACCTTTCGCAAAACCTTC |
| pdc-adhA-adhR integrated in *Klebsiella* at rrlE | |
| K.rrlE-up-EcoRI | gcagaattcTTAAGTGGGAAACGATGTGG |
| K.rrlE-down-EcoRI | gcagaattcAAAGGTTCACGGGGTCTTTC |
| K.rrlE-up | TTAAGTGGGAAACGATGTGG |
| K.rrlE-down | AAAGGTTCACGGGGTCTTTC |
| K.rrlE-1 | GAAGTGACAAATGCCCTGCT |
| K.rrlE-2 | CACCGTAGTGCCTCGTCAT |

During strain construction, cultures were grown aerobically at 30, 37, or 39 C in Luria broth (10 g l−1 Difco tryptone, 5 g l−1 Difco yeast extract and 5 g l−1 NaCl) containing 2% (w/v) glucose or arabinose. Ampicillin (50 mg l−1), apramycin (50 mg l−1), tetracycline (12.5 mg l−1) or kanamycin (50 mg l−1) were added as needed. For fermentative ethanol production, strains were grown without antibiotics at 37 C in either luria broth or AM1 mineral salts medium (Alfredo et al., 2007) with 10% (w/v) xylose.

Genetic Methods

Standard methods were used for genomic DNA extraction (Qiagen), PCR amplification (Stratagene and Invitrogen), transformation, plasmid extraction (Qiagen), and restriction endonuclease digestion (New England Biolabs).

Plasmid Construction for Cat Gene Deletion (1st Round)

Figure 18:
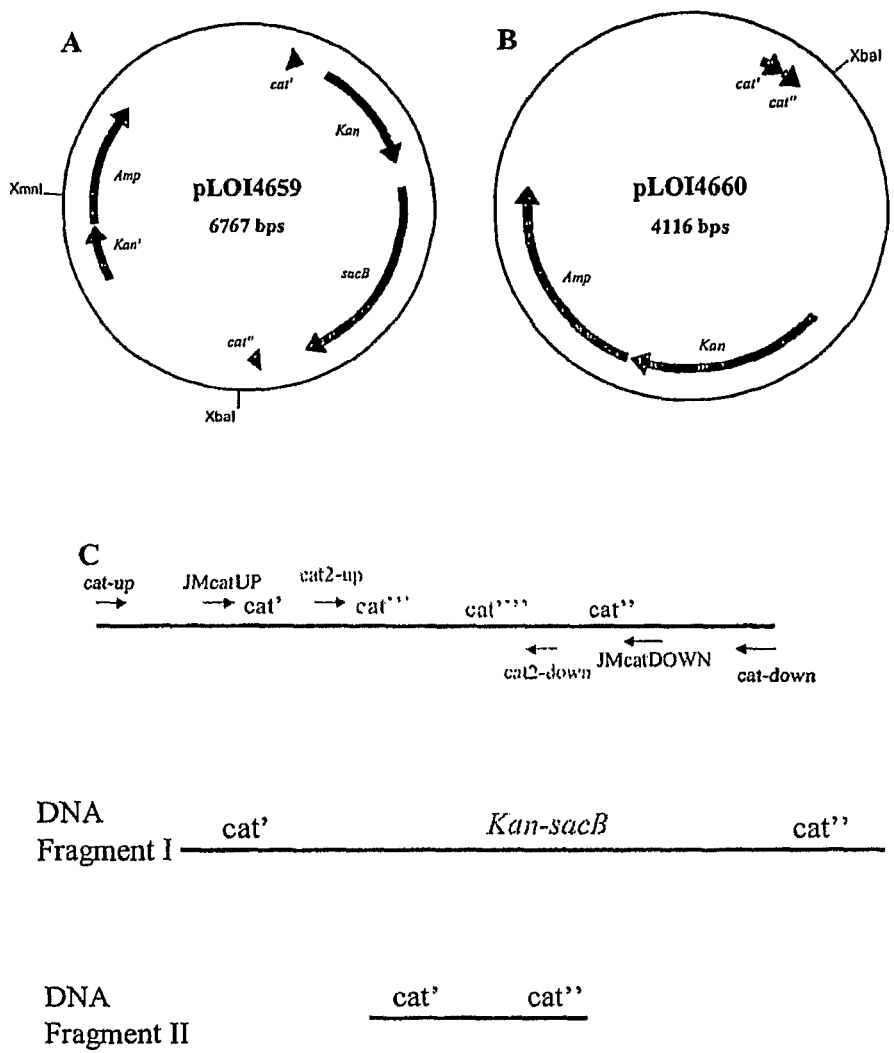
FIG. 18 (A-C) are three schematic drawings. A and B show the plasmids used for cat deletion (first round). Panel C is a map of the cat deletion (first round).

The method for deleting chloramphenicol resistance gene (cat) was modified based on two steps of homologous recombination (Thomason et al., 2005), which would leave no antibiotic gene and foreign gene scars after the gene deletion. At the first recombination, a 200 bp DNA fragment, located in the middle of the cat gene, was replaced by a DNA cassette containing a kanamycin resistance gene (Kan) and levansucrase gene (sacB) (FIG. 18 C). At the second recombination, DNA fragments outside of the first 200 bp fragment were used as recombination targets (FIG. 18 C), and the Kan-sacB cassette was removed based on sucrose sensitivity. Since those colonies with sacB gene would accumulate levansucrase with sucrose, which would kill the cell, only those recombinants which remove the Kan-sacB cassette could survive.

The Kan gene was amplified from pCR2.1-TOPO using primer set Kan-up/Kan-down (Table 7, above), which was then digested with XhoI and AccI and cloned into pLOI4162 (XhoI and AccI) to replace the cat gene and obtain pLOI4292. The Kan-sacB cassette (2899 bp) was obtained by digesting pLOI4292 with PacI followed by T4 treatment, which was used for further ligation.

It was thought at the beginning that there was only one cat gene in the chromosome of KO11-RD1 and BW34, and one round of cat gene deletion would eliminate the cat resistance. A 400 bp DNA fragment located in the middle of cat gene (FIG. 18 C) was amplified from KO11-RD1 using primer set JMcatUP/JMcatDOWN (Table 7) and cloned into pCR2.1-TOPO to get pLOI4657. This plasmid was then digested with SfoI and self-ligated to inactivate the kanamycin resistance and pLOI4658 was obtained. The plasmid DNA of pLOI4658 was diluted 1000 times and used as template for PCR (using primer set cat-1/cat-2, outward amplification). The amplified DNA fragment (cat'-cat"-TOPO, 3868 bp) was used to ligate with the Kan-sacB cassette (2899 bp) to make plasmid pLOI4659 (FIG. 18 A, 6767 bp). The PCR product of cat-1/cat-2 was also treated with T4 polynucleotide kinase (New England Biolabs) to add phosphate at the end of the fragment, and self-ligated to make plasmid pLOI4660 (FIG. 18 B, 4958 bp). The plasmid pLOI4659 and pLOI4660 were digested by XbaI and diluted 1000 times, which were used as template to amplify DNA fragment I (cat'-Kan-sacB-cat") for the first step and fragment II (cat'-cat") for the second step of homologous recombination (using primer set JMcatUP/JMcatDOWN) (FIG. 18 C).

Plasmid Construction for Cat Gene Deletion (2nd and 3rd Round)

After deleting the cat gene, the resulting strains were still resistant to high chloramphenicol concentration. It was thought that there would be more than one cat gene copy in the chromosome of the original strains. If using the previous DNA fragment I (cat'-Kan-sacB-cat"), which came from pLOI4659, for the further recombination, it would have the same chance of integrating at a new cat gene site or a deleted cat gene site. In order to make the further cat gene deletion occurred at a new site, a new plasmid was constructed. A 200 bp DNA fragment located in the middle of cat gene was amplified from KO11-RD1 using primer set cat2-upPstI/cat2-downPstI (Table 7), which was digested with PstI and cloned into pBR322 at PstI site to get pLOI4661. This plasmid DNA was diluted 1000 times and used as template for PCR (using primer set cat2-3/cat2-4, outward amplification). The amplified DNA fragment (cat'''-cat''''-TOPO, 4521 bp) was used to ligate with the Kan-sacB cassette (2899 bp) to make plasmid pLOI4662 (FIG. 19A, 7420 bp). This plasmid DNA were digested by XbaI, and diluted 1000 times, which was used as template to amplify DNA fragment III (cat'''-Kan-sacB-cat'''') for the first step homologous recombination (using primer set cat2-up/cat2-down). DNA fragment H, which came from pLOI4660, was still used for the second step recombination (FIG. 19C).

Cat Gene Deletion

At the first recombination of cat gene deletion, DNA fragment I (cat'-Kan-sacB-cat") was electroporated to KO11-RD1 or BW34 having the red recombinase expressing plasmid pKD46 (Datsenko and Wanner 2000) or pLOI3420 (Brent et al., 2005), which was then incubated at 30° C. for 2 h out-growth and then spread in LB plates having ampicillin and kanamycin (for KO11-RD1) or apramycin and kanamycin (for BW34). The kanamycin was for selection of correct recombinant, and the ampicillin or apramycin was to keep pKD46 or pLOI3420 for the second step recombination. After incubation at 30° C. for about 18 h, three colonies were picked and used to prepare competent cell, to which DNA fragment II (cat'-cat") was electroporated. After that, the culture was incubated at 30° C. for 4 h out-growth and then transferred to a 250 ml flask containing 100 ml LB medium (no sodium chloride) and 10% sucrose. The culture was incubated at 30° C. overnight, which was then streaked in LB plates (no sodium chloride) with 6% sucrose and incubated at either 30 or 39° C. for 16 h. Incubation at 30° C. was to keep the red recombinase plasmid for further cat gene deletion. Colonies were picked from the plates and tested for their ampicillin or apramycin, and kanamycin sensitivity. They were also tested for resistance to different chloramphenicol concentration, and PCR amplification using different primer sets.

Re-Integration of Alcohol Gene

After deleting all the cat genes, the resulting strains also lost the ethanol producing ability. The pdc gene could not be detected by PCR. In order to produce ethanol, the alcohol gene was re-integrated at either the pflB or rrlE site.

Plasmids for integrating alcohol gene at *Klebsiella* pflB site were constructed as followed. The pflB gene was amplified from *Klebsiella oxytoca* M5A1 using primer set pflB-up2-M5A1/pflB-down2-M5A1, which was then cloned into pCR2.1-TOPO to get pLOI4637. The pflB gene was subcloned from pLOI4637 (KpnI-XbaI, blunted by T4 DNA polymerase) into pLOI2394 at EcoRI site (blunted by Klenow) to get pLOI4645. This plasmid DNA was diluted 1000 times and used as template for PCR (using primer set pflB-2-M5A1/pflB-3-M5A1, outward amplification). The amplified DNA fragment was used to ligate with the pdc-adhA-adhB-FRT-Kan-FRT cassette (obtained from pLOI3491 by PacI digestion and blunted by T4 DNA polymerase) to make plasmid pLOI4646. The K.pflB'-pdc-adhA-adhB-FRT-Kan-FRT-K.pflB" cassette was then sub-cloned from pLOI4646 (AscI digestion) into pLOI2225 at AscI site to get pLOI4649 (FIG. 5), which had the R6K replication origin. The plasmid pLOI4649 was digested with AscI, and the big DNA fragment containing the alcohol gene (K.pflB'-pdc-adhA-adhB-FRT-Kan-FRT-K.pflB") was gel purified, which was then electroporated to BW34-XZ106 (with red recombinase pLOI3421) and spread on LB kan plates to select for the integrants. Colonies from the LB kan plate were picked and patched on different plates, including LB 2% glucose (LBG), LB apramycin (LB Aac), LB kanamycin (LB Kan) and LB cat40.

Construction of plasmids for integrating alcohol gene at *Klebsiella* rrlE site was a little different. The rrlE gene was amplified from *Klebsiella oxytoca* M5A1 using primer set K.rrlE-up-EcoRI/K.rrlE-down-EcoRI, which was then digested with EcoRI and cloned into pLOI2394 at EcoRI site to get pLOI4673. The next steps were the same as in the pflB, and the plasmids constructed were shown on Table 6.

The methods for constructing plasmids for integrating the alcohol gene at *E. coli* rrlE and pflB sites were the same as integrating alcohol gene at *Klebsiella* rrlE site. The plasmids constructed at each step were shown on Table 6.

Removal of Kan Gene by Flipase

Strain RD1-XZ027 was first transformed with pFT-A, which had the flipase gene, and spread on LB Amp plates. Several colonies were picked and inoculated in a 250 ml flask with 10 ml LB medium with ampicillin. After the OD grew up to 0.1, 1 ml chlorotetracycline stock (20 mg/100 ml LB) was added to induce the flipase gene expression. After growing at 30° C. 6 h, the medium was streaked on LBG plates, and incubated at 39° C. for overnight. Colonies were picked and patched on different plates, including LBG, LB Kan, LB Amp and LB cat40.

The kan gene was removed the same way in the *Klebsiella* strain BW34-XZ118, except plasmid pLOI3409 was used which has the flipase gene and is apramycin resistant.

Fermentation

The ethanol production of all the strains were tested in 50 ml LB medium with 10% xylose in a 125 ml flask at 37° C. and 100 rpm, which had no pH adjust. The final ethanologenic strains were also tested in AM1 medium with 10% either xylose or glucose. The pH was adjusted to be at 7.0 by automatically adding 2N potassium hydroxide.

Analysis

Cell mass was estimated by measuring the optical density at 550 nm (OD550). Ethanol concentration was measured by GC. Organic acids and sugar concentration were measured by HPLC (Underwood et al., 2002).

The 1st Round of Cat Gene Deletion in KO11-RD1

The two-step homologous recombination method was used for cat gene deletion in KO11-RD1. At the second recombination, both 30 C and 39 C temperature points were used when streaking on LB 6% sucrose plates. The 30 C temperature was used for keeping the red recombinase plasmid pKD46, which could be used for further cat gene deletion. Several colonies were picked in both conditions and patched on different plates, including LBG, LB Kan, LB Amp, and LB Cat with different concentrations (40, 100, 200, 400, 600 mg l-1). For those colonies which came from the 30 C condition, they grew slower and were also sensitive to ampicillin. Two colonies were selected, which were named RD1-XZ001 and RD-XZ002. They were both sensitive to cat400, while resistant to cat200 (as shown in Table 8). Colonies, which came from the 39 C condition, grew faster. Two colonies were selected, which were named RD1-XZ003 and RD-XZ004. They were both sensitive to cat600, while resistant to cat400 (Table 8, below).

TABLE 8

| Strains | Cat Resistance | PCR Cat 1/2 | PCR Cat U/D | PCR PflB 5/2 | OD550 D1 | OD550 D2 | EtOH (g/L) D1 | EtOH (g/L) D2 |
|---|---|---|---|---|---|---|---|---|
| KO11-RD1 | 600R | — | N | + | 14.2 | 18 | 28.2 | 40.8 |
| RD1-XZ001 | 400S 200R | — | N | N/A | 3.8 | 3.7 | 2.3 | 1.8 |
| RD1-XZ002 | 400S 200R | — | N | N/A | 5.6 | 7.0 | 4.2 | 8 |
| RD1-XZ003 | 600S 400R | — | N | N/A | 12 | 12 | 12.2 | 30.1 |
| RD1-XZ004 | 600S 400R | — | N | + | 11.2 | 12.4 | 12.1 | 30.2 |

In Table 8, the primer set cat U/D (cat-up/cat-down) should amplify a 635 bp DNA fragment, which was near the whole cat gene (660 bp), in the native cat gene.

In this situation, the PCR result was marked as N (native). If the middle part of the cat gene was deleted, a shorter DNA fragment (462 bp) should be amplified. In this situation, the PCR result was marked as D (deleted). The primer set of both cat-1/cat-2 and pflB-2/pflB-5 was used to detect the tandem duplication of pdc-adhB-cat cassette.

All the colonies were still resistant to high chloramphenicol concentration, which suggested that there were still other cat gene copies remained in the chromosome. This is reasonable since the original strain KO11-RD1 was optimized for a long time to increase the ethanol productivity by selecting for resistance to increased chloramphenicol concentration. It was thought that both the cat gene and the alcohol gene (pdc-adhB) were duplicated in the chromosome.

The cat gene was tested in these four strains by PCR. The primer set cat-up/cat-down should amplify a 635 bp DNA fragment, which was near the whole cat gene (660 bp), in the native cat gene. If the middle part of the cat gene was deleted, a shorter DNA fragment (462 bp) should be amplified. However, in all the four strains, only the 630 bp DNA fragment was amplified, while the short 462 bp fragment was not obtained. It was possibly because the second step recombination didn't happen at the cat' and cat" site. Since there are maybe multiple alcohol genes in the chromosome, the second step recombination had great chance to happen at the pdc and adhB site, which is much bigger than the cat gene. That would remove all the DNA fragments between them, including the cat'-KansacB-cat" cassette, which would result in no amplification of the short 462 bp fragment.

The primer set pflB-2/pflB-5 was used to verify the tandem duplication of pdc-adhB-cat cassette. PCR products were obtained in both the original strain KO11-RD1 and RD1-XZ004. The amplified 2.5 kb DNA fragment were sequenced to obtain the sequence information between the duplication. The primer set cat-1/cat-2 was also used to detect the tandem duplication of pdc-adhB-cat cassette. However, there was no DNA fragment amplified. This was maybe because the DNA fragment between primer cat-1 and cat-2 is so big that the current PCR Kit was not efficient enough to get any amplification.

All the four strains were tested for ethanol production in a 125 ml flask fermentation with LB and 10% xylose. Strains RD1-XZ001 and RD1-XZ002 grew much slower and lost almost all the ethanol producing ability. The cell growth and ethanol production after 2 days decreased a little in strains RD1-XZ003 and RD1-XZ004, from 40 g/l in the original strain KO11-RD1 to near 30 g/l (Table 8). Strain RD1-XZ004 was selected for further cat gene deletion.

The 2nd Round of Cat Gene Deletion in RD1-XZ004

Figure 19:
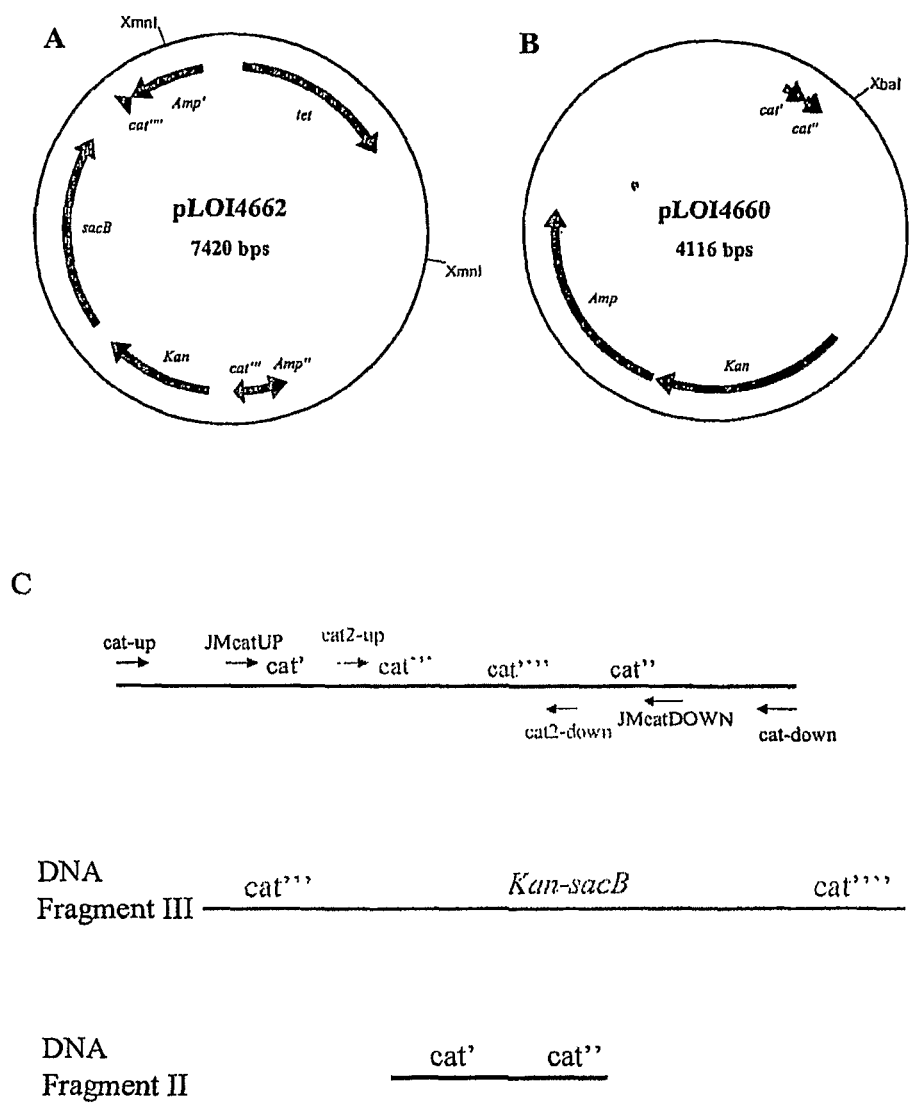
FIG. 19 (A-C) are three schematic drawings. A and B show the plasmids used for cat deletion (second and third round). Panel C is a map of the cat deletion (second and third round).

It was thought that during the second recombination of the 1st round of cat gene deletion, all the cat'-Kan-sacB-cat" cassette was removed because there was no short fragment (462 bp) amplified by the primer set cat-up/eat-down. However, it was still possible that the two-crossover recombination happened at the cat' and cat" sites since a negative PCR result is always not strong enough. If so, the cat' and cat" would be left at the chromosome. For the further cat gene deletion, if still using DNA fragment I (cat'-Kan-sacB-cat") at the first recombination step, the two-crossover recombination had the same chance to target either at the new untouched cat site, or at the already deleted cat site. In order to avoid the recombination happen at the already deleted cat site, a new DNA fragment III was created (FIG. 19 C). In this fragment, the Kan-sacB cassette was inserted between cat'" and cat"" fragments, which is inside of the cat' and cat" fragment in the cat gene. They were removed after a round of cat gene deletion. When using DNA fragment III for the first step recombination, the two-crossover recombination could only happen at the new untouched cat gene. For the second step recombination, DNA fragment II was used so that the cat'" and cat"" fragments could be removed (FIG. 19 C), which could help to delete the new untouched cat gene at the further rounds. This strategy can delete all the cat genes one by one no matter how many cat genes duplicated in the chromosome.

At the second recombination, both 30 C and 39 C were used when streaking on LB 6% sucrose plates. Several colonies were picked in both conditions and patched on different plates, including LBG, LB Kan, LB Amp, and LB Cat with different concentrations (40, 100, 200, 400, 600 mg l−1). As during the 1st round of cat gene deletion, those colonies, which came from the 30 C condition, grew slower and were still sensitive to ampicillin. Two colonies were selected, which were named RD1-XZ009 and RD-XZ010. They were both sensitive to cat40 (Table 9, shown below). Colonies, which came from the 39 C condition grew faster. Two colonies were selected, which were named RD1-XZ011 and RD-XZ012. They were both sensitive to cat200, while resistant to cat100 (Table 9).

TABLE 9

| Strains | Cat Resistance | PCR[a] Cat U/D | Cat2 U/D | Pdc Up/1 | Cat-up Pdc-1 | OD550 D1 | OD550 D2 | EtOH (g/L) D1 | EtOH (g/L) D2 |
|---|---|---|---|---|---|---|---|---|---|
| KO11-RD1 | 600R | N | + | + | + | 14.2 | 18 | 28.2 | 40.8 |
| RD1-XZ004 | 600S 400R | N | + | + | + | 11.2 | 12.4 | 12.1 | 30.2 |
| RD1-XZ009 | 40S | N | + | + | − | 3.2 | 3.2 | 0.7 | 0.5 |
| RD1-XZ010 | 40S | N | + | + | − | 3.3 | 3.3 | 0.8 | 0.5 |
| RD1-XZ011 | 100R 200S | N | + | + | + | 4.0 | 4.1 | 2.6 | 2.1 |
| RD1-XZ012 | 100R 200S | N | + | + | − | 3.2 | 3.2 | 0.8 | 0.5 |

In Table 9, The primer set cat U/D (cat-up/cat-down) should amplify a 635 bp DNA fragment, which was near the whole cat gene (660 bp), in the native cat gene. In this situation, the PCR result was marked as N (native). If the middle part of the cat gene was deleted, a shorter DNA fragment (462 bp) should be amplified. In this situation, the PCR result was marked as D (deleted); The primer set cat2 U/D (cat2-up/cat2-down) was used to amplify the middle of the cat gene. For the native cat gene, the amplified PCR product is 200 bp. For those deleted cat, no DNA fragment should be amplified; The primer set pdc up/1 (pdc-up/pdc-1) was used to detect the pdc gene; The primer set cat-up/pdc-1 was used to detect the tandem duplication of pdc-adhB-cat cassette.

The cat gene was tested in these four strains by PCR. When using primer set cat-up/cat-down, the native 635 bp DNA fragment was still amplified from RD1-XZ009 and RD1-XZ010, suggesting there was at least one cat gene remained in the chromosome. However, these two strains were all sensitive to cat40. This might be due to a recombination that occurred in the chromosome because of the extended time that the red recombinase pKD46 was kept at 30 C, which might have removed some essential genes for cell growth and antibiotic resistance. Accordingly, only the strains which came from the 39 C incubation condition were used. As during the 1st round of cat gene deletion, for strains RD1-XZ011 and RD1-XZ012, only the native 635 bp DNA fragment was amplified using primer set cat-up/cat-down, while the short 462 bp DNA fragment was not amplified.

The primer set cat2-up/cat2-down was also tested, which should amplify a 190 bp DNA fragment in the native cat gene. No DNA fragment should be amplified after one round of cat gene deletion. The 190 bp DNA fragment was amplified from all the four strains. The primer set pdc-up/pdc-1 was used to test the pdc gene, and it was also amplified from all the four strains. The primer set cat-up/pdc-1 was used to verify the tandem duplication of pdc-adhB-cat cassette. PCR product was obtained from the original strain KO11-RD1, from the parental strain RD1-XZ004 and from strain RD1-XZ011. However, it was not amplified from RD1-XZ012. This suggested that in strain RD1-XZ012, at least two neighboring cat genes were removed together at the 2nd round, which resulted in no DNA fragment amplified by primer set cat-up/pdc-1.

All the four strains were tested for ethanol production in a 125 ml flask fermentation with LB and 10% xylose. All the strains grew much slower and, unexpected, lost almost all the ethanol producing ability (Table 9), although the pdc gene was still detected.

The 3rd Round of Cat Gene Deletion in RD1-XZ012

The cat gene was deleted again in strain RD1-XZ012 using the same strategy as in the 2nd round. At the second recombination, only the 39 C temperature point was used when streaking on LB 6% sucrose plates. Several colonies were picked and patched on different plates, including LBG, LB Kan, LB Amp, and LB Cat with different concentrations (40, 100, 200, 400, 600 mg l–1). All the strains were sensitive to kan, amp, and cat40.

The cat gene was tested by PCR. When using primer set cat2-up/cat2-down, no DNA fragment was amplified from all the colonies, indicating that no active cat gene was remained in the chromosome (Table 10, shown below). There was also no DNA fragment amplified from all the colonies when using primer set cat-up/pdc-1. When using primer set cat-up/cat-down, the short 462 bp DNA fragment was amplified from some colonies, while no DNA fragment was amplified from other colonies (Table 10).

TABLE 10

| Strains | Cat Resistance | PCR$^a$ Cat U/D | Cat2 U/D | Pdc Up/1 | Cat-U Pdc-1 | OD550 D1 | OD550 D2 | EtOH (g/L) D1 | EtOH (g/L) D2 |
|---|---|---|---|---|---|---|---|---|---|
| KO11-RD1 | 600R | N | + | + | + | 14.2 | 18 | 28.2 | 40.8 |
| RD1-XZ004 | 600S 400R | N | + | + | + | 11.2 | 12.4 | 12.1 | 30.2 |
| RD1-XZ012 | 100R 200S | N | + | + | – | 3.2 | 3.2 | 0.8 | 0.5 |
| RD1-XZ016 | 40S | D | – | + | – | 2.8 | 2.6 | 0.9 | 0.6 |
| RD1-XZ017 | 40S | D | – | + | – | 2.9 | 2.7 | 0.8 | 0.5 |
| RD1-XZ018 | 40S | – | – | – | – | 2.4 | 2.3 | 0 | 0 |
| RD1-XZ019 | 40S | – | – | – | – | 2.4 | 2.4 | 0 | 0 |

In Table 10, the primer set cat U/D (cat-up/cat-down) should amplify a 635 bp DNA fragment, which was near the whole cat gene (660 bp), in the native cat gene. In this situation, the PCR result was marked as N (native). If the middle part of the cat gene was deleted, a shorter DNA fragment (462 bp) should be amplified. In this situation, the PCR result was marked as D (deleted); The primer set cat2 U/D (cat2-up/cat2-down) was used to amplify the middle of the cat gene. For the native cat gene, the amplified PCR product is 200 bp. For those deleted cat, no DNA fragment should be amplified; The primer set pdc up/1 (pdc-up/pdc-1) was used to detect the pdc gene.

Two colonies were picked from each type and tested by primer set pdc-up/pdc-1. For RD1-XZ016 and RD1-XZ017, the pdc gene fragment was amplified. However, for RD1-XZ018 and RD1-XZ019, no DNA fragment was amplified. It was thought that, for RD1-XZ018 and RD1-XZ019, during the second step recombination, the two-crossover recombination didn't happen at the cat' and cat" site while at site outside of the pdc-adhB-cat cassette, which removed all the DNA fragments inside.

All the four strains were tested for ethanol production in a 125 ml flask fermentation with LB and 10% xylose. All the strains grew slowly. Strain RD1-XZ016 and RD1-XZ017 produced very few ethanol (below 1 g/l), although the pdc gene was still detected. Strain RD1-XZ018 and RD1-XZ019 produced no ethanol (Table 10).

Re-Integration of the Alcohol Gene into RD1-XZ018

In order to obtain the ethanol producing ability, the alcohol cassette (pdc-adhA-adhB) was re-integrated into strain RD1-XZ018. Both the pflB and rrlE genes were chosen as the integration sites.

Figure 20:
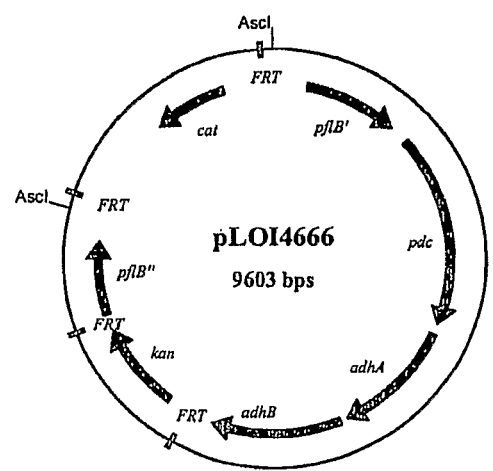
FIG. 20 is a schematic showing the plasmid used for integrating alcohol gene to *E. coli* at pflB site.
Figure 21:
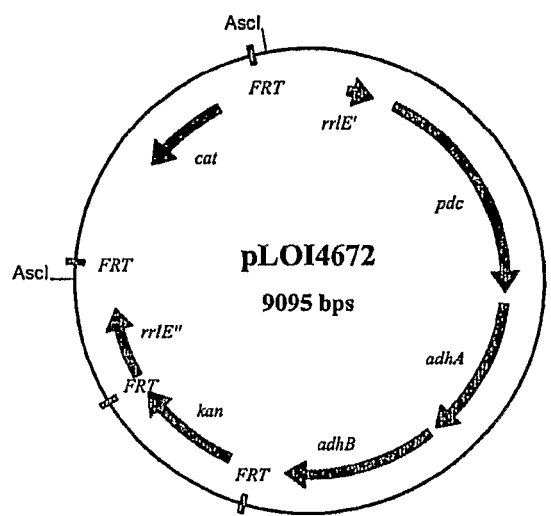
FIG. 21 is a schematic showing the plasmid used for integrating alcohol gene to *E. coli* at rrlE site.

After electroporating the pflB'-pdc-adhA-adhB-FRT-kan-FRT-pflB" cassette (FIG. 20) into strain RD1-XZ018 and spreading on LB Kan plates, no colonies grew. However, when using the rrlE'-pdc-adhA-adhB-FRT-kan-FRT-rrlE" cassette (FIG. 21), colonies came out in the LB Kan plates just after 8 hours. There were two types of colonies. One was thick and raised. Six colonies of this type was picked and named RD1-XZ020, RD1-XZ021, RD1-XZ022, RD1-XZ023, RD1-XZ026 and RD1-XZ027. The other type was thin and flat. Two colonies of this type was picked and named RD1-XZ024 and RD1-XZ025. All the eight strains were tested by PCR using the primer set rrlE-up/pdc-1, which were all positive.

The eight strains were tested for ethanol production in a 125 ml flask fermentation with LB and 10% xylose. RD1-XZ024 and RD1-XZ025, which had thin and flat colonies, grew much slower than others and produced very few ethanol. The other strains having thick and raised colonies grew even faster than the original strain KO11-RD1. They also produced near the same amount of ethanol as KO11-RD1, about 40 g/l after 48 h (Table 11, shown below). RD1-XZ027 produced the most ethanol after 24 h (34.6 g/l), suggesting that it had the biggest ethanol productivity. This strain was used for further kan gene removal by the flipase treatment.

TABLE 11

| Strains | Colony physiology | OD550 D1 | OD550 D2 | EtOH (g/L) D1 | EtOH (g/L) D2 |
|---|---|---|---|---|---|
| KO11-RD1 | | 14.2 | 18 | 28.2 | 40.8 |
| RD1-XZ018 | | 2.4 | 2.3 | 0 | 0 |
| RD1-XZ020 | Thick and raised | 18 | 16 | 30.4 | 41.5 |
| RD1-XZ021 | Thick and raised | 17.5 | 14 | 32.4 | 42.4 |
| RD1-XZ022 | Thick and raised | 18.4 | 17 | 33.3 | 40.4 |
| RD1-XZ023 | Thick and raised | 19 | 18.5 | 33.2 | 40.8 |
| RD1-XZ024 | Thin and flat | 2.8 | 2.6 | 0.6 | 0.5 |
| RD1-XZ025 | Thin and flat | 2.7 | 2.6 | 0.3 | 0.2 |
| RD1-XZ026 | Thick and raised | 18 | 18 | 32.8 | 39.2 |
| RD1-XZ027 | Thick and raised | 18 | 18.8 | 34.6 | 38.4 |
| RD1-XZ028 | | 17.2 | 16.2 | 33.8 | 43.6 |
| RD1-XZ029 | | 17.6 | 17.2 | 33.7 | 41.3 |
| RD1-XZ030 | | 17.4 | 17 | 32.6 | 41.3 |
| RD1-XZ031 | | 17 | 16.2 | 33.3 | 40.8 |

After removing the kan gene from RD1-XZ027 by the flipaset treatment, four colonies were picked and named RD1-XZ028, RD1-XZ029, RD1-XZ030 and RD1-XZ031. They were tested for ethanol production in a 125 ml flask fermentation with LB and 10% xylose. Cell growth and ethanol production was similar in these four strains. RD1-XZ028 produced the most ethanol (43.6 g/l after 48 h), which was a little higher than the original strain KO11-RD1.

The whole process for cat gene deletion in KO11-RD1 and alcohol gene re-integration is summarized in Table 16.

Cat Gene Deletion in BW34

The cat gene was also deleted in *Klebsiella oxytoca* BW34 by the two step homologous recombination method. At the second recombination, both 30 C and 39 C were used when streaking on LB 6% sucrose plates. Several colonies were picked in both conditions and patched on different plates, including LBG, LB Kan, LB Aac, and LB Cat with different concentrations (40, 100, 200, 400, 600 mg l−1). For those colonies which came from the 30 C condition, they grew slower and were also unexpectedly sensitive to apramycin. Two colonies were selected, which were named BW34-XZ101 and BW34-XZ102. They were both sensitive to cat400, while resistant to cat200 (Table 12). Colonies, which came from the 39 C condition, grew faster. Most of the 39 C colonies were sensitive to cat400 and resistant to cat200. Two colonies were selected, which were named BW34-XZ103 and BW34-XZ104. However, one colony was still resistant to cat600, which was named BW34-XZ2105, and one colony was sensitive to cat40, which was named BW34-XZ106.

TABLE 12

| Strains | Cat Resistance | PCR$^a$ Cat 1/2 | Cat U/D | OD550 D1 | OD550 D2 | EtOH (g/L) D1 | EtOH (g/L) D2 |
|---|---|---|---|---|---|---|---|
| BW34 | 600R | + | N | 8.2 | 7.6 | 11.2 | 18.4 |
| BW34-XZ101 | 400S 200R | − | N | 1.7 | 2.2 | 0.2 | 0 |
| BW34-XZ102 | 400S 200R | − | N | 2.0 | 2.1 | 0.2 | 0 |
| BW34-XZ103 | 400S 200R | − | N | 2.1 | 2.2 | 0.2 | 0.2 |
| BW34-XZ104 | 400S 200R | − | N | 2.1 | 2.3 | 0.2 | 0 |
| BW34-XZ105 | 600R | + | N | 6.8 | 7.0 | 7.5 | 12.3 |
| BW34-XZ106 | 40S | − | − | 2.3 | 1.8 | 0.2 | 0 |

In Table 12, The primer set cat U/D (cat-up/cat-down) should amplify a 635 bp DNA fragment, which was near the whole cat gene (660 bp), in the native cat gene. In this situation, the PCR result was marked as N (native). If the middle part of the cat gene was deleted, a shorter DNA fragment (462 bp) should be amplified. The primer set of cat-1/cat-2 was used to detect the tandem duplication of cat gene.

The cat gene was tested in all six strains by PCR. The primer set cat-1/cat-2 was used to detect the duplication of cat gene. A DNA fragment near 1.8 kb was amplified from the original strain BW34, suggesting that the tandem duplication didn't happen for the whole K.pflB'-pdc-adhB-cat-K.pflB" cassette, as in KO11-RD1. In contrast, only the cat gene was duplicated. The amplified 1.8 kb DNA fragment was sent for sequencing to obtain the sequence information between the duplication. After the cat gene deletion, the 1.8 kb DNA fragment could only be amplified from strain BW34-XZ105. It was not amplified from all the other 5 strains, suggesting that both cat genes were deleted together.

When using the primer set cat-up/cat-down, the 635 bp DNA fragment (Native) was amplified in all the strains except BW34-XZ106. The reason why the short 462 bp fragment was not obtained was thought to be the same as in KO11-RD1. Since it was demonstrated that two cat genes were deleted together due to the cat-1/cat-2 PCR results, it was thought that there were at least three cat gene copies in the chromosome of BW34.

It was surprising that no DNA fragment was amplified from BW34-XZ106, and this strain was sensitive to cat40. This was possibly because the two-crossover recombinations of the second step happened outside of the all the cat genes, which resulted in removal of the genes together.

All the six strains were tested for ethanol production in a 125 ml flask fermentation with LB and 10% xylose. The cell growth and ethanol production of BW34-XZ105 was similar as the original strain BW34. However, all the other 5 strains grew very slowly, and lost all the ethanol producing ability (Table 7).

Re-Integration of the Alcohol Gene into BW34-XZ106 at pflB Site

In order to obtain the ethanol production ability, the alcohol cassette (pdc-adhA-adhB) was re-integrated into strain BW34-XZ106. Both the pflB and rrlE genes were chosen as the integration sites.

Figure 22:
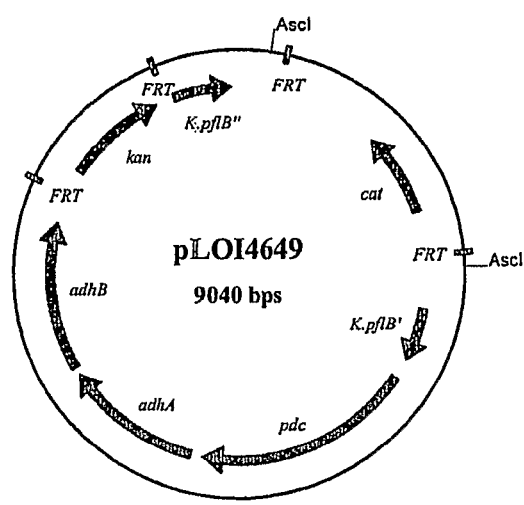
FIG. 22 is a schematic showing the plasmid used for integrating alcohol gene to *Klebsiella* at pflB site.

After electroporating the K.pflB'-pdc-adhA-adhB-FRT-kan-FRT-K.pflB" cassette (FIG. 22) into strain BW34-XZ106 and spreading on LB Kan plates, there were two types of colonies. One type was thin and flat, which occupied 99% in the plate. Two colonies were picked and named BW34-XZ107 and BW34-XZ108. The other type was thick and raised, which was only 1% in the plate. Two colonies were picked and named BW34-XZ109 and BW34-XZ110.

Figure 24:
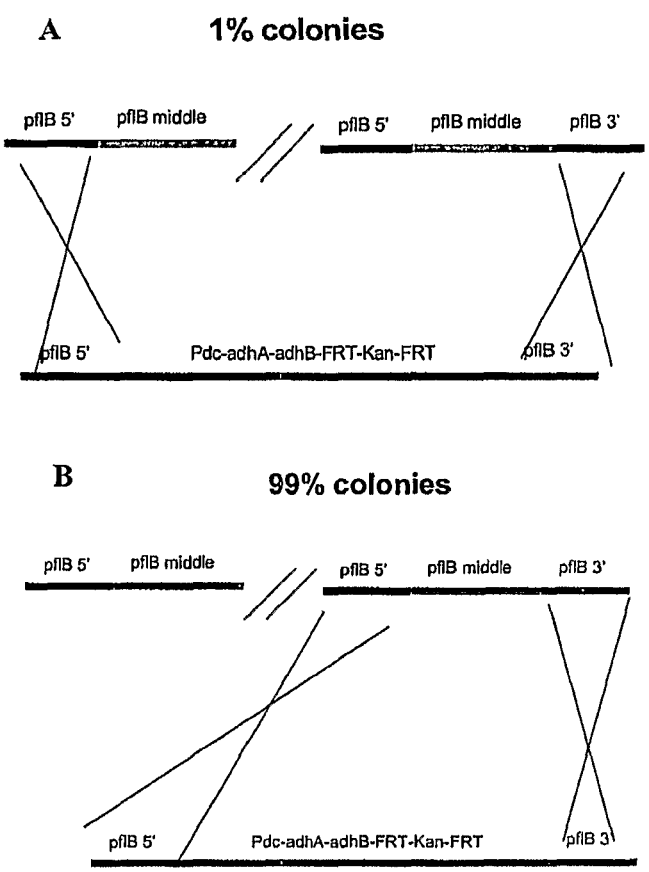
FIGS. 24 (A and B) are maps showing the integration of the alcohol gene at the *Klebsiella* pflB site.

The primer set K.focA-up/pdc-1 was used to verify the recombination. The forward primer (K.focA-up) was upstream of the pflB gene in the chromosome. For strain BW34-XZ109 and BW34-XZ110, it could amplify a product near 1.5 kb. However, for BW34-XZ107 and BW34-XZ108, no DNA fragment was amplified. It was thought that the native pflB 3'-end was deleted during previous cat gene deletion in strain BW34-XZ106. For BW34-XZ109 and BW34-XZ110, the two-crossover recombination happened in the native pflB 5'-end site in the *Klebsiella* chromosome, and a duplicated pflB 3'-end in other site (FIG. 24 A). However, for BW34-XZ107 and BW34-XZ108, the two-crossover recombination all happened in the pflB site, which was duplicated later in the chromosome in other sites (FIG. 24 B). It had a much higher opportunity to happen in the latter way, which could explain why there was 99% colonies in this type.

All the four strains were tested for ethanol production in a 125 ml flask fermentation with LB and 10% xylose. The ethanol production after 48 h in BW34-XZ109 and BW34-XZ110 was a little higher than in BW34-XZ107 and BW34-XZ108, all of which were better than the original strain BW34 (Table 13, shown below). Since BW34-XZ110 produced the most ethanol (22.4 g/l after 48 h), it was used for further kan gene removal.

TABLE 13

| Strains | Colony Physiology | PCR$^a$ pdc up/1 | pflB U/D | focA/ pdc 1 | OD550 D1 | OD550 D2 | EtOH (g/L) D1 | EtOH (g/L) D2 |
|---|---|---|---|---|---|---|---|---|
| BW34 | | − | + | − | 8.2 | 7.6 | 11.2 | 18.4 |
| BW34-XZ106 | | − | + | − | 2.3 | 1.8 | 0.2 | 0 |
| BW34-XZ107 | Thin and flat | + | + | − | 8.0 | 7.6 | 9.7 | 19.9 |
| BW34-XZ108 | Thin and flat | + | + | − | 7.5 | 7.6 | 9.6 | 19.4 |
| BW34-XZ109 | Thick and dense | + | − | + | 8.0 | 6.6 | 12.7 | 20.9 |
| BW34-XZ110 | Thick and dense | + | − | + | 9.5 | 7.4 | 12.8 | 22.4 |
| BW34-XZ113 | | | | | 7.3 | 9.5 | 12.6 | 22.2 |
| BW34-XZ114 | | | | | 7.4 | 9.8 | 13 | 22.1 |

TABLE 13-continued

| Strains | Colony Physiology | PCR[a] pdc up/1 | pflB U/D | focA/ pdc 1 | OD550 D1 | OD550 D2 | EtOH (g/L) D1 | EtOH (g/L) D2 |
|---|---|---|---|---|---|---|---|---|
| BW34-XZ115 | | | | | 7.7 | 7.0 | 13 | 21.9 |
| BW34-XZ116 | | | | | 7.3 | 7.6 | 13.1 | 21.2 |

In Table 13, The primer set pdc-up/pdc-1 was used to check the pdc gene; The primer set K.focA-up/pdc-1 was used to verify the two-crossover recombination site.

After removing the kan gene from BW34-XZ110 by the flipaset treatment, four colonies were picked and named BW34-XZ113, BW34-XZ114, BW34-XZ115, and BW34-XZ116. They were also tested for ethanol production in a 125 ml flask fermentation with LB and 10% xylose. Cell growth and ethanol production was similar in these four strains. BW34-XZ113 produced the most ethanol (22.2 after 48 h). This strain was also tested for ethanol production in AM1 medium with either 10% glucose or 10% xylose. The ethanol production after 48 h in the xylose fermentation (36.4 g/l) was much higher than in glucose (28.7 g/l), both of which were better than in LB medium (22.2 g/l) (Table 14, shown below). There were also some other co-products formed, such as lactate, succinate and acetate (Table 14). Especially in the glucose fermentation, there was 294 mM lactate produced. These co-products were due to the activity of other fermentative enzyme (lactate dehydrogenase, fumarate reductase and acetate kinase) competing with the pyruvate decarboxylase for pyruvate.

TABLE 14

| | OD | EtOH (g/L) | Lactate (mM) | Succinate (mM) | Acetate (mM) |
|---|---|---|---|---|---|
| LB 10% xylose no pH control | 9.5 | 22.2 | | | |
| AM1 10% Xylose (initial OD 0.1) | 8.2 | 36.4 | 63.7 | 63.1 | 26.8 |
| AM1 10% Glucose (initial OD 0.1) | 4.6 | 28.7 | 294 | 19.3 | 16.1 |

Re-Integration of the Alcohol Gene into BW34-XZ106 at rrlE Site

Figure 23:
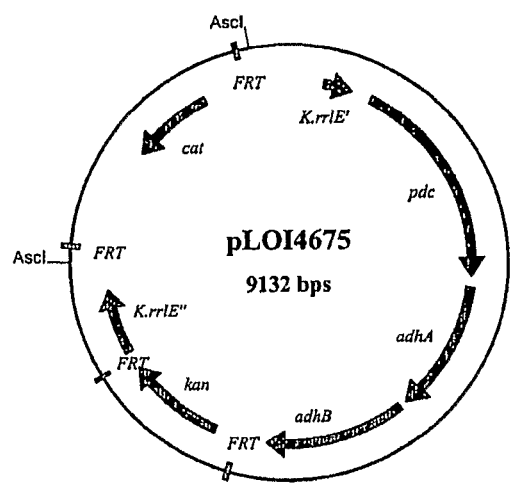
FIG. 23 is a schematic showing the plasmid used for integrating alcohol gene to *Klebsiella* at rrlE site.

After electroporating the K.rrlE'-pdc-adhA-adhB-FRT-kan-FRT-K.rrlE" cassette (FIG. 23) into strain BW34-XZ106 and spreading on LB Kan plates, there were two types of colonies. One type was thick and raised. Two colonies were picked and named BW34-XZ117 and BW34-XZ118. The other type was thin and flat. Two colonies were picked and named BW34-XZ119 and BW34-XZ120.

All the four strains were tested for ethanol production in a 125 ml flask fermentation with LB and 10% xylose. The ethanol production after 48 h in BW34-XZ117 and BW34-XZ118 was similar as in BW34-XZ110, which had the alcohol gene integrated at pflB site. In contrast, the ethanol production was much lower in BW34-XZ119 and BW34-XZ120 (Table 15, shown below). BW34-XZ118 was used for further kan gene removal since it produced the most ethanol (22.5 g/l after 48 h).

TABLE 15

| Strains | Colony Physiology | OD550 D1 | OD550 D2 | EtOH (g/L) D1 | EtOH (g/L) D2 |
|---|---|---|---|---|---|
| BW34 | | 8.2 | 7.6 | 11.2 | 18.4 |
| BW34-XZ106 | | 2.3 | 1.8 | 0.2 | 0 |
| BW34-XZ117 | Thick and raised | 6.2 | 5.4 | 13 | 22 |
| BW34-XZ118 | Thick and raised | 6.9 | 6.4 | 14.1 | 22.5 |
| BW34-XZ119 | Thin and flat | 5.9 | 5 | 7 | 11.7 |
| BW34-XZ120 | Thin and flat | 7.2 | 5.6 | 10.1 | 13.5 |
| BW34-XZ121 | | 7.0 | 5.5 | 13.7 | 22.5 |
| BW34-XZ122 | | 7.1 | 4.8 | 13.2 | 22.5 |
| BW34-XZ123 | | 7.5 | 5.8 | 14.1 | 23.2 |
| BW34-XZ124 | | 6.9 | 5.0 | 13.7 | 22.2 |

After removing the kan gene from BW34-XZ118 by the flipaset treatment, four colonies were picked and named BW34-XZ121, BW34-XZ122, BW34-XZ123, and BW34-XZ124. They were also tested for ethanol production in a 125 ml flask fermentation with LB and 10% xylose. Cell growth and ethanol production was similar in these four strains. BW34-XZ123 produced the most ethanol (23.2 g/l after 48 h), which was a little higher than in BW34-XZ113 (22.2 g/l), which had the alcohol gene integrated at pflB site.

Table 16, shown below shows a summary of cat gene deletion in KO11-RD1 and re-integration of alcohol gene and Table 17, shown below shows a summary of cat gene deletion in BW34 and re-integration of alcohol gene.

TABLE 16

| Step | Process | Strains | Cat Resistance | OD550 D1 | OD550 D2 | EtOH (g/L) D1 | EtOH (g/L) D2 |
|---|---|---|---|---|---|---|---|
| 0 | | KO11-RD1 | 600R | 14.2 | 18 | 28.2 | 40.8 |
| 1 | 1st round of cat deletion | RD1-XZ004 | 600S 400R | 11.2 | 12.4 | 12.1 | 30.2 |
| 2 | 2nd round of cat deletion | RD1-XZ012 | 100R 200S | 3.2 | 3.2 | 0.8 | 0.5 |
| 3 | 3rd round of cat deletion | RD1-XZ018 | 40S | 2.4 | 2.3 | 0 | 0 |
| 4 | Alcohol gene re-integrated at rrlE site | RD1-XZ027 | 40S | 18 | 18.8 | 34.6 | 38.4 |
| 5 | Removal of kan gene | RD1-XZ028 | 40S | 17.2 | 16.2 | 33.8 | 43.6 |

TABLE 17

| Step | Process | Strains | Cat Resistance | OD550 D1 | OD550 D2 | EtOH (g/L) D1 | EtOH (g/L) D2 |
|---|---|---|---|---|---|---|---|
| 0 | | BW34 | 600R | 8.2 | 7.6 | 11.2 | 18.4 |
| 1 | Cat deletion | BW34-XZ106 | 40S | 2.3 | 1.8 | 0.2 | 0 |
| 2A | Alcohol gene re-integrated at pflB site | BW34-XZ110 | 40S | 9.5 | 7.4 | 12.8 | 22.4 |
| 2B | Removal of kan gene | BW34-XZ113 | 40S | 7.3 | 9.5 | 12.6 | 22.2 |
| 3A | Alcohol gene re-integrated at rrlE site | BW34-XZ118 | 40S | 6.9 | 6.4 | 14.1 | 22.5 |
| 3B | Removal of kan gene | BW34-XZ123 | 40S | 7.5 | 5.8 | 14.1 | 23.2 |

In summary, several strains of *K. oxytoca* have been re-engineered for ethanol production without the use of antibiotic resistance markers. These are summarized in Table 18, below:

TABLE 18

| Strains | Process | Colony physiology | genotype |
|---|---|---|---|
| BW34-XZ106 | Cat deletion in BW34 | | M5A1, ΔbudAB::FRT |
| BW34-XZ107 | Re-integrating the alcohol gene into BW34-XZ106 at pflB site | Thin and flat | M5A1, ΔbudAB::FRT, pflB'-pdc-adhA-adhB-FRT-Kan-FKT-pflB" |
| BW34-XZ108 | | | |
| BW34-XZ109 | | Thick and raised | |
| BW34-XZ110 | | | |
| BW34-XZ111 | Removing Kan from BW34-XZ108 | | M5A1, ΔbudAB::FRT, pflB'-pdc-adhA-adhB:FRT-pflB" |
| BW34-XZ112 | | | |
| BW34-XZ113 | Removing Kan from BW34-XZ110 | | |
| BW34-XZ114 | | | |
| BW34-XZ115 | | | |
| BW34-XZ116 | | | |
| BW34-XZ117 | Re-integrating the alcohol gene into BW34-XZ106 at rrlE site | Thick and raised | M5A1, ΔbudAB::FRT, rrlE'-pdc-adhA-adhB-FRT-Kan-FRT-rrlE" |
| BW34-XZ118 | | | |
| BW34-XZ119 | | Thin and flat | |
| BW34-XZ120 | | | |
| BW34-XZ121 | Removing Kan from BW34-XZ118 | | M5A1, ΔbudAB::FRT, rrlE'-pdc-adhA-adhB:FRT-rrlE" |
| BW34-XZ122 | | | |
| BW34-XZ123 | | | |
| BW34-XZ124 | | | |

These reengineered strains were tested using standard procedures for simultaneous saccharification and fermentation (SSF) reactions with acid hydrolyzed bagasse fiber. Table 19, below, shows a compositional analysis of belt cakes used in these studies.

TABLE 19

| SP5C_C2 | 55.6% Glucan | 3.75% Xylan |
|---|---|---|
| 070207T150-BW-CAKE | 53.44% Glucan | Xylan ND |

SSF of strains XZ112, 113, 115 was performed using VOP #12-SSF of Bagasse with the following exception: 100 g dry wt bagasse was placed into the fermentation vessel with 600 mL of tap water, and was autoclaved for 30 minutes at 121° C. Due to limited substrate, SSF of strains XZ112 and XZ113 were performed on Screw Press bagasse "SP5C_C2", and SSF of strain XZ115 was performed on Cake #070207T150-BW-CAKE-ROLL. SP5C_C2 (pH 6.46) was not additionally washed as previous BW34 fermentations reached 72% conversion in 72 hours. Cake #070207T150-BW-CAKE-ROLL was washed to pH 4.96 using VOP #28-Biomass Fiber Washing.

Figure 17:
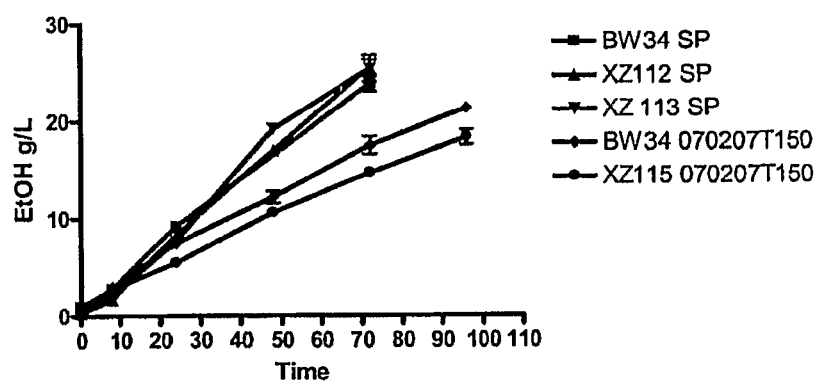
FIG. 17 is a graph demonstrating ethanol production during SSF of acid hydrolyzed bagasse by strains of *K. oxytoca*.

As shown in FIG. 17, of the new armless strains, XZ112 and XZ113 (76% conversion, 72 hrs) performed the best with regard to the original BW34 strain (72% conversion, 72 hrs). XZ115 and the control BW34 both had trouble fermenting cake 070207T150, possibly due to the substrate's susceptibility to enzymatic attack or its inhibitor concentration. One possibility is that a more thorough washing is needed as the wash pH (4.96) was on the low side compared to SP5C_C2 (6.46). An additional 24 hours was advantageous to reach 70% conversion with this cake, suggesting the latter possibility; a rate decreasing presence of inhibitory compounds. Although XZ115 performed approximately 10% less efficiently as measured by overall conversion, it is inconclusive that this strain is or is not on level with the original BW34, as inhibitory compounds may not be evenly dispersed throughout the cake.

Table 20, below, provides a summary of recent literature for ethanol production from xylose by recombinant biocatalysts. Many of these are known to require complex nutrients. Whether compared in complex medium or mineral salts medium, none ferment xylose to ethanol with a higher yield or titer than the novel recombinant strains of *E. coli* described herein.

TABLE 20

Ethanol Production from Xylose by Recombinant Organisms

| Strain | Xylose (g L$^{-1}$) | Nutrients | Ethanol (g L$^{-1}$) | Yield (g g$^{-1}$) | Reference |
|---|---|---|---|---|---|
| Mineral medium | | | 2.8 | 0.03 | |
| *E. coli* B (ATCC 11303) | 90 | LB | 9.1 | 0.1 | As used in this study |

TABLE 20-continued

Ethanol Production from Xylose by Recombinant Organisms

| Strain | Xylose (g L$^{-1}$) | Nutrients | Ethanol (g L$^{-1}$) | Yield (g g$^{-1}$) | Reference |
|---|---|---|---|---|---|
| Ec KO11 | 90 | LB | 43.2 | 0.48 | This study |
| Ec LY168 | 90 | LB | 45.3 | 0.50 | This study |
| Ec KO11 | 90 | Min | 26.9 | 0.30 | This study |
| Ec LY165 | 90 | Min | 44.9 | 0.50 | This study |
| Ec LY168 | 90 | Min | 45.5 | 0.51 | This study |
| Ec FBR5(pLOI297) | 95 | LB | 41.5 | 0.44 | Dien et al. 2000 |
| Ko M5A1(pLOI555) | 100 | LB | 46.0 | 0.46 | Ohta et al. 1991 |
| Zm CP4(pZB5) | 25 | YE | 11.0 | 0.44 | Zhang et al. 1995 |
| Zm CP4(pZB5) | 60 | YE | 23.0 | 0.38 | Lawford & Rousseau 1999 |
| Zm CP4(pZB5) | 80 + 8 G | YE | 36.6 | 0.42 | Lawford & Rousseau 1999 |
| Zm ZM4/Ac(pZB5) | 60 | LB | 11.0 | 0.44 | Jeon et al. 2005 |
| Ssp 1400(pLNH32) | 50 | YEP | 23.0 | 0.46 | Ho et al. 1998 |
| Sc RE700A(pKDR) | 50 | YEP | 23.0 | 0.46 | Sedlak & Ho 2004 |
| Sc RWB202-AFX | 20 | Synth. | 8.6 | 0.43 | Kuyper et al. 2004 |
| Sc RWB217 | 20 | Synth. | 8.7 | 0.44 | Kuyper et al. 2005 |

Abbreviations:
LB, yeast extract + tryptone;
Min, minerals + 1 mM betaine;
YE, yeast extract supplemented with phosphate;
YEP, supplemented with yeast extract and peptone;
Synth, minerals supplemented with a mixture of vitamins;
8 G, 8 g of glucose added per liter.

References

Alterthum F & Ingram L O (1989) Efficient ethanol production from glucose, lactose, and xylose by recombinant *Escherichia coli*. *Appl. Environ. Microbiol.* 55: 1943-1948.

Arntzen C. E. & Dale B E (1999) *Biobased industrial products, priorities for research and commercialization*. National Academy Press, Washington D.C.

Asghari A, Bothast R J, Doran J B, and Ingram L O (1996) Ethanol production from hemicellulose hydrolysates of agricultural residues using genetically engineered *Escherichia coli*. *J. Indus. Microbiol.* 16: 42-47.

Aristidou, A. A., K. San, and G. N. Bennett. 1995. Metabolic engineering of *Escherichia coli* to enhance recombinant protein production through acetate reduction. Biotechnol. Prog. 11:475-478.

Ausubel, F M, Brent R, Kingston R E, Moore D D, Deidman J G, Smith I A, and Struhl K (ed.) (1987) *Current protocols in molecular biology*. John Wiley & Sons, Inc., New York, N.Y.

Beall, D. S., K. Ohta, and L. O. Ingram (1991) Parametric studies of ethanol production from xylose and other sugars by recombinant *Escherichia coli*. Biotechnol. Bioeng. 38:296-303.

Causey T B, Zhou S, Shanmugam K T, and Ingram L O (2003) Engineering the metabolism of *Escherichia coli* W3110 for the conversion of sugar to redox-neutral and oxidized products: homoacetate production. *Proc. Natl. Acad. Sci. USA* 100: 825-832.

Cebolla A, Royo J L, de Lorenzo V, and Santero E (2002) Improvement of recombinant protein yield by a combination of transcriptional activation and stabilization of gene expression. *Appl. Environ. Microbiol.* 68: 5034-5041.

Conway, T, Sewell G W, Osman Y A, Ingram, L O (1987) Cloning and sequencing of the alcohol dehydrogenase II gene from *Zymomonal mobilis*. *J. Bacteriol.* 169: 2591-2597.

Datsenko K A & Wanner B L (2000) One-step inactivation of chromosomal genes in *Escherichia coli* K-12 using PCR products. *Proc. Natl. Acad. Sci. USA* 97: 6640-6645. de Lorenzo, V., M. Herrero, U. Jakubzik, and K. N. Timmis. 1990. Mini-Tn5 transposon derivatives for insertion mutagenesis, promoter probing, and chromosomal insertion of cloned DNA in gram-negative eubacteria. J. Bacteriol. 172: 6568-6572.

Dien, B S, Nichols N N, O'Bryan P J and Bothast R J (2000) Development of new ethanologenic *Escherichia coli* strains for fermentation of lignocellulosic biomass. *Appl. Biochem. Biotechnol.* 84-6: 181-196.

Doran, J. B., and L. O. Ingram. 1993. Fermentation of crystalline cellulose to ethanol by *Klebsiella oxytoca* containing chromosomally integrated *Zymomonas mobilis* genes. Biotechnol. Prog. 9:533-538.

Drewke C and Ciriacy M (1988) Overexpression, purification and properties of alcohol dehydrogenase IV from *Saccharomyces cerevisiae*. *Biochim Biophys Acta*. 950 (1): 54-60.

Farmer, W. R., and J. C. Liao. 1997. Reduction of aerobic acetate production by *Escherichia coli*. Appl. Environ. Microbiol. 63:3205-3210.

Hasona A, York S W, Yomano L P, Ingram L O, and Shanmugam K T (2002) Decreasing the level of ethyl acetate in ethanologenic broths of *Escherichia coli* KO11 by expression of *Pseudomonas putida* estZ esterase. *Appl. Environ. Microbiol.* 68: 2651-2659.

Ho N W Y, Chen Z and Brainard A P (1998) Genetically engineered *Saccharomyces* yeast capable of effective cofermentation of glucose and xylose. *Appl. Environ. Microbiol.* 64: 1852-1859.

Ingram L O, Gomez P F, Lai X, Moniruzzaman M, Wood B E, Yomano L P, and York S W (1998) Metabolic engineering of bacteria for ethanol production. *Biotechnol. Bioengin.* 58: 204-214.

Jeon Y J, Svenson C J, Rogers P L (2005) Over-expression of xylulokinase in a xylose-metabolizing recombinant strain of *Zymomonas mobilis*. *FEMS Microbiol. Lett.* 85: 85-92.

Keshav K F, Yomano L P, An H, and Ingram L O (1990) Cloning of the *Zymomonas mobilis* structural gene encoding alcohol dehydrogenase I (adhA): Sequencing comparison and expression in *Escherichia coli*. *J. Bacteriol.* 172: 2491-2497.

Kuyper, M, Toirkens M J, Diderich J A, Winkler A A, van Dijken J P and Pronk J T (2005) Evolutionary engineering of mixed-sugar utilization by a xylose-fermenting *Saccharomyces cerevisiae* strain. *FEMS Yeast Research* 5:925-934.

Kuyper M, Winkler A A, van Dijken J P, Pronk J T (2004) Mineral metabolic engineering of *Saccharomyces cerevisiae* for efficient anaerobic xylose fermentation: a proof of principle. *FEMS Yeast Research* 4: 655-664.

Lindhal L, Zengel J M. Ribosomal genes in *Escherichia coli*. *Annu Rev Genet.* 20: 297-326. 1986.

Lawford H G & Rousseau J D (1999) The effect of glucose on high-level xylose fermentations by recombinant *Zymomonas* in batch and fed-batch fermentations. *Appl. Biochem. Biotechnol.* 98: 429-448.

Lee E-C., D. Yu, J. Martinez de Velasco, L. Tessarollo, D. A. Swing, D. L. Court, N. A. Jenkins, and N. G. Copeland. 2001. A highly efficient *Escherichia coli*-based chromosome engineering system adapted for recombinogenic targeting and subcloning of BAC DNA. *Genomics* 73: 56-65.

Martinez A, York S W, Yomano L P, Pineda V L, Davis F C, Shelton J C, and Ingram L O (1999) Biosynthetic burden and plasmid burden limit expression of chromosomally integrated heterologous genes (pdc, adhB) in *Escherichia coli*. *Biotechnol. Prog.* 15: 891-897.

Talarico, L A, Malgorzata G A, Ingram L O, Maupin-Furlow J A. (2005) Construction and expression of an ethanol production operon in Gram-positive bacteria. *Microbiology.* 151. 1-9.

Martinez, A., T. B. Grabar, K. T. Shanmugam, L. P. Yomano, S. W. York, and L. O. Ingram. 2007. Low salt medium for lactate and ethanol production by recombinant *Escherichia coli* B. *Biotechnol. Lett.* 29: 397-404.

Martinez-Morales F, Borges A C, Martinez A, Shanmugam K T, and Ingram L O (1999) Chromosomal integration of heterologous DNA in *Escherichia coli* with precise removal of markers and replicons. *J. Bacteriol.* 181: 7143-7148.

Moniruzzaman, M., X. Lai, S. W. York, and L. O. Ingram. 1997. Isolation and molecular characterization of high-performance cellobiose-fermenting spontaneous mutants of ethanologenic *Escherichia coli* KO11 containing the *Klebsiella oxytoca* casAB operon. *Appl. Environ. Microbiol.* 63: 4633-4637.

Miller J H (1992) A short course in bacterial genetics: a laboratory manual and handbook for *Escherichia coli* and related bacteria. Cold Spring Harbor Laboratory Press, Cold Spring Harbor, N.Y.

Nomura M, Gourse R, Baughman G. Regulation of the synthesis of ribosomes and ribosomal components. *Annu Rev Biochem.* 53: 75-117. 1984.

Ohta K, Beall D S, Mejia J P, Shanmugam K T, and Ingram L O (1991) Genetic improvement of *Escherichia coli* for ethanol production: chromosomal integration of *Zymomonas mobilis* genes encoding pyruvate decarboxylase and alcohol dehydrogenase II. *Appl. Environ. Microbiol.* 57: 893-900.

Posfai, G, Koob M D, Kirkpatrick H A, and Blattner F R (1997) Versatile insertion plasmids for targeted genome manipulations in bacteria: isolation, deletion, and rescue of the pathogenicity island LEE of the *Escherichia coli* O157:H7 genome. *J. Bacteriol.* 179: 4426-4428.

Purvis, J E, Yomano L P and Ingram L O (2005) Enhanced trehalose production improves growth of *Escherichia coli* under osmotic stress (salts and sugars). *Appl. Environ. Microbiol.* 71: 3761-3769.

Raj, K. C., L. A. Talarico, L. O. Ingram and J. A. Maupin-Furlow. 2002. Cloning and characterization of the *Zymobacter palmae* pyruvate decarboxylase (pdc): Comparison of bacterial homologues. *Appl. Environ. Microbiol.* 68:2869-2876.

Raj, K. C., L. O. Ingram and J. A. Maupin-Furlow. 2001. Pyruvate decarboxylase: a key enzyme for the oxidative metabolism of lactic acid by *Acetobacter pasteurianus*. *Arch. Microbiol.* 176: 443-451. Sambrook J & Russell D W (2001) *Molecular cloning: a laboratory manual*. Cold Spring Harbor Laboratory, Cold Spring Harbor, N.Y.

Reid M. F., Fewson C. A. 1994. Molecular Characterization of Microbial Alcohol Dehydrogenases. Critical Reviews in Microbiology. 20(1): 13-56.

Sedlak M & Ho N W Y. 2004. Characterization of the effectiveness of hexose transporters for transporting xylose during glucose and xylose co-fermentation by a recombinant *Saccharomyces* yeast. Yeast 21: 671-684. Silhavay, T. J., M. L. Berman, and L. W. Enquist. 1984. Experiments with gene fusions. Cold Springs Harbor Laboratory Press. Cold Springs Harbor, N.Y.

Talarico, L. A., L. O. Ingram and J. A. Maupin-Furlow. 2001. Production of Gram-positive *Sarcina ventriculi* pyruvate decarboxylase in *Escherichia coli*. Microbiology-SGM 147:2425-2433.

Teixeira de Mattos, M. J. and D. W. Tempest. 1983. Metabolic and energetic aspects of the growth of *Klebsiella aerogenes* NCTC 418 on glucose in anaerobic chemostat culture. Arch. Microbiol. 134:80-85.

Thomason L, D. L. Court, M. Bubunenko, N. Constantino, H. Wilson, S. Dana, A. Oppenheim. 2005. Recombineering: Genetic engineering in bacteria using homologous recombination. In: Ausubel, F. M., R. Brent, R. E. Klingston, D. D. Moore, J. G. Deidman, J. A. Smith, K. Struhl (eds). Current Protocols in Molecular Biology. John Wiley & Sons Inc., New York. pp 1.16.1-21

Underwood S A, Buszko M L, Shanmugam K T, and Ingram L O (2004) Lack of protective osmolytes limits final cell density and volumetric productivity of ethanologenic *Escherichia coli* KO11 during xylose fermentation. Appl. Environ. Microbiol. 70: 2734-2740.

Vaidya A N, Pandey R A, Mudliar S, Kumar M S, Chakrabarti T, Devotta S (2005) Production and recovery of lactic acid for polylactide—an overview. *Crit. Rev. Environ. Sci. and Technol.* 35: 429-467.

Wanner B L, Kodaira R, and Neidhardt F C (1977). Physiological regulation of a decontrolled lac operon. *J. Bacteriol.* 130: 212-222.

Wasewar K L (2005) Separation of lactic acid: Recent advances *Chem. Biochem. Engin. Quart.* 19: 159-172.

Wood, B. E. and L. O. Ingram, (1992) Ethanol production from cellobiose, amorphous cellulose and crystalline cellulose by recombinant *Klebsiella oxytoca* containing chromosomally integrated *Zymomonas mobilis* genes for ethanol production and plasmids expressing thermostable cellulase genes from *Clostridium thermocellum*. Appl. Environ. Microbiol. 58:2103-2110.

Wood, B. E. (1997) Improvements to the simultaneous saccharification and fermentation of lignocellulose by *Klebsiella oxytoca* strain P2 using ultrasound and heterologous endoglucanases expressed in the ethanologenic bacterium *Escherichia coli* strain KO11. M.S. Thesis. University of Florida. Gainesville Fla.

Wood, B. E., D. S. Beall, and L. O. Ingram. (1997) Production of recombinant bacterial endoglucanase as a co-product with ethanol during fermentation using derivatives of *Escherichia coli* KO11. *Biotech. Bioengin.* 55: 547-555.

Wood, B. E., Beall, D. S, and L. O. Ingram. (1997b) Production of recombinant bacterial endoglucanase as a co-product with ethanol during fermentation using derivatives of *Escherichia coli* KO11. Biotech. Bioeng. 55:547-555.

Wood, B. E. (2005) IMPROVING *Klebsiella oxytoca* FOR ETHANOL PRODUCTION FROM LIGNOCELLULOSIC BIOMASS A dissertation presented to the graduate school of the University of Florida in partial fulfillment of the requirements for the degree of doctor of philosophy.

Wood B E, Yomano L P, York S W, and Ingram L O (2005) Development of industrial-medium-required elimination of the 2,3-butanediol fermentation pathway to maintain ethanol yield in an ethanologenic strain of *Klebsiella oxytoca*. *Biotechnol. Prog.* 21: 1366-1372.

Wright, J. D. 1988. Ethanol from lignocellulosics: an overview. Energy Prog. 84:71-80.

York, S W & Ingram L O (1996) Ethanol production by recombinant *Escherichia coli* KO11 using crude yeast autolysate as a nutrient supplement. *Biotechnol. Lett.* 18: 683-688.

Zhang J & Greasham R (1999) Chemically defined media for commercial fermentations. *Appl. Microbiol. Biotechnol.* 51: 407-421.

Zhang, M, Eddy C, Deanda K, Finkelstein M and Picataggio S (1995) Metabolic engineering of a pentose pathway in ethanologenic *Zymomonas mobilis*. *Science* 267: 240-243.

Zhou, S., F. C. Davis, and L. O. Ingram. 2001. Gene integration and expression and extracellular secretion of *Erwinia chrysanthemi* endoglucanase CelY (celY) and CelZ (celZ) in ethanologenic *Klebsiella oxytoca* P2. Appl. Environ. Microbiol. 67:6-14.

Zhou, S, and L. O. Ingram. 2001. Simultaneous saccharification and fermentation of amorphous cellulose to ethanol by recombinant *Klebsiella oxytoca* SZ21 without supplemental cellulase. Biotechnol. Lett. 23:1455-1462.

Zhou, S., T. B. Causey, A. Hasona, K. T. Shanmugam, and L. O. Ingram. 2003. Production of optically pure D-lactic acid in mineral salts medium by metabolically engineered *Escherichia coli* W3110. Appl Environ Microbiol. 69:399-407.

Zhou S, Grabar T B, Shanmugam K T, and Ingram L O (2006a) Betaine tripled the volumetric productivity of D(−)-lactate by *Escherichia coli* strain SZ132 in mineral salts medium. *Biotechnology Letters*. 28(9): 671-676.

Zhou S, Shanmugam K T, Yomano L P, Grabar T B, and Ingram L O (2006b) Fermentation of 12% glucose to 1.2 M lactate by *Escherichia coli* strain SZ194. *Biotechnology Letters*. 28(9): 663-670.

Zhou S, Yomano L P, Shanmugam K T, and Ingram L O (2005) Fermentation of 10% sugar to D(−)-lactate by engineered *Escherichia coli* B. *Biotechnol. Lett.* 27: 1891-1896.

Zhu M M, Skraly F A, and Cameron D C (2001) Accumulation of methylglyoxal in anaerobically grown *Escherichia coli* and its detoxification by expression of the *Pseudomonas putida* glyoxylase I gene. *Metab. Engin.* 3: 218-225.

Incorporation By Reference

All patents, published patent applications and other references disclosed herein are hereby expressly incorporated herein in their entireties by reference.

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. A recombinant *Escherichia coli* (*E.coli*) bacterium which comprises a full complement of heterologous ethanol production genes integrated into a ribosomal RNA operon, wherein the heterologous ethanol production genes are pdc, adhA and adhB.

2. The recombinant *E. coli* bacterium of claim 1, wherein the recombinant bacterium does not contain antibiotic markers.

3. The recombinant *E. coli* bacterium of claim 1, wherein one or more genes encoding polypeptides that interfere with or otherwise reduce the amount of ethanol produced by the full complement of heterologous ethanol production genes are removed or inactivated.

4. The recombinant *E. coli* bacterium of claim 1, further comprising one or more genes that encode polypeptides that facilitate production of ethanol or otherwise increase the amount of ethanol produced by the full complement of heterologous ethanol production genes.

5. The recombinant *E. coli* bacterium of claim 1, wherein expression of said full complement of heterologous ethanol production genes causes the recombinant bacterium to produce ethanol as the primary fermentation product.

6. The recombinant *E. coli* bacterium of claim 1, wherein:
(a) the full complement of heterologous ethanol production genes that are integrated into a ribosomal RNA operon, wherein expression of said full complement of heterologous ethanol production genes causes the recombinant bacterium to produce ethanol as the primary fermentation product; and
(b) one or more genes that encode polypeptides that facilitate production of ethanol or otherwise increase the amount of ethanol produced by the full complement of heterologous ethanol production genes; and wherein:
  (i) one or more antibiotic markers are removed; and
  (ii) one or more genes encoding polypeptides that interfere with or otherwise reduce the amount of ethanol produced by the full complement of heterologous ethanol production genes are inactivated.

7. The recombinant *E. coli* bacterium of claim 1, wherein the ribosomal RNA operon comprises a gene selected from the group consisting of rrnB, rrlE, rrnC, rrnD, rrnE, rrnG and rrnH.

8. The recombinant *E. coli* bacterium of claim 6, wherein the ribosomal RNA operon comprises the rrlE gene.

9. The recombinant *E. coli* bacterium of claim 1, wherein the full complement of heterologous ethanol production genes is derived from *Zyrnomonas mobilis*.

10. The recombinant *E. coli* bacterium of claim 2, wherein the antibiotic marker is selected from the group consisting of apramycin, kanamycin, tetracycline, ampicillin and chloramphenicol.

11. The recombinant *E. coli* bacterium of claim 3, wherein the one or more genes that are inactivated encode proteins involved in fermentative routes for NADH oxidation.

12. The recombinant *E. coli* bacterium of claim 4, wherein the one or more genes that are inactivated encode proteins involved in alternate pathways for pyruvate metabolism.

13. The recombinant *E. coli* bacterium of claim 5, wherein the one or more genes that are inactivated are endogenous to the bacterium.

14. The recombinant *E. coli* bacterium of claim 6, wherein the one or more genes that are inactivated are heterologous to the bacterium.

15. The recombinant *E. coli* bacterium of claim 11, wherein the one or more genes that are inactivated are selected from the group consisting of the genes comprising the focA-pflB gene region, ldhA, ackA, adhE,frd operon, casAB and mgsA.

16. The recombinant *E. coli* bacterium of claim 15, wherein the ackA, adhE, ldh genes and the frd operon encode proteins that are involved in alternate pathways for pyruvate metabolism.

17. The recombinant *E. coli* bacterium of claim 16, wherein said the focA-pflB gene region, ldhA, ackA, adhE, genes comprising the frd operon and mgsA are endogenous genes.

18. The recombinant *E. coli* bacterium of claim 17, wherein said casAB genes are heterologous genes.

19. The recombinant *E. coli* bacterium of claim 18, wherein an ldhA gene is deleted.

20. The recombinant *E. coli* bacterium of claim 19, wherein the ldhA gene is an endogenous gene.

21. recombinant *E. coli* bacterium of claim 1, further comprising a focA-pflB gene region.

22. The recombinant *E. coli* bacterium of claim 21, wherein the focA-pflB gene region is an endogenous gene region.

23. The recombinant *E. coli* bacterium of claim 1, wherein the focA-pflB gene region is from *Escherichia coli*.

24. The recombinant *E. coli* bacterium of claim 5, wherein the one or more genes that encode a polypeptide that facilitates production of ethanol or otherwise increases the amount of ethanol produced by the full complement of heterologous ethanol production is a gene that encodes a secretory protein, a polysaccharase, glucanase, an endoglucanase, an exoglucanase, a cellobiohydrolase,β-glucosidase, endo-1, 4β-xylanase, β-xylosidase, α-glucuronidase, α-L-arabinofuranosidase, acetylesterase, acetylxylanesterase, α-amylase, β-amylase, glucoamylase, pullulanase, β-glucanase, hemicellulase, arabinosidase, mannanase, pectin hydrolase or pectate lyase.

25. The recombinant *E. coli* bacterium of claim 24, wherein the gene is an estZ gene.

26. The recombinant *E. coli* bacterium of claim 25, wherein the estZ gene is a heterologous gene.

27. The recombinant *E. coli* bacterium of claim 26, wherein the estZ gene is from *Pseudomonas putida*.

28. The recombinant *E. coli* bacterium of claim 25, wherein the genes that encode polypeptides that facilitate production of ethanol or otherwise increase the amount of ethanol produced by the full complement of heterologous ethanol production genes comprise lacA and lacY genes.

29. The recombinant *E. coli* bacterium of claim 28, wherein the lacA and lacY genes are endogenous genes.

30. The recombinant *E. coli* bacterium of claim 29, wherein the lacA and lacY genes are from *Escherichia coli*.

31. The recombinant *E. coli* bacterium of claim 24, wherein the genes that encode polypeptides that facilitate production of ethanol or otherwise increase the amount of ethanol produced by the full complement of heterologous ethanol production genes comprise a celY gene.

32. The recombinant *E. coli* bacterium of claim 31, wherein the celY gene is a heterologous gene.

33. The ecombinant *E. coli* bacterium of claim 32, wherein the celY gene is from *Envinia chrysantherni*.

34. The recombinant *E. coli* bacterium of claim 1, wherein an mgsA gene is deleted.

35. The recombinant *E. coli* bacterium of claim 34, wherein the mgsA gene is an endogenous gene.

36. The recombinant *E. coli* bacterium of claim 1, wherein the bacterium produces ethanol as the primary fermentation product under anaerobic conditions.

37. The recombinant *E. coli* bacterium of claim 1, wherein the recombinant bacterium is capable of growth in mineral salts medium.

38. The recombinant *E. coli* bacterium of claim 37, wherein the mineral salts medium contains xylose.

39. The recombinant *E. coli* bacterium of claim 38, wherein the mineral salts medium comprises at least about 7% xylose.

40. The recombinant *E. coli* bacterium of claim 39, wherein the mineral salts medium contains betaine.

41. The recombinant *E. coli* bacterium of claim 1, wherein the recombinant bacterium is capable of growth in AM1 medium.

42. The recombinant *E. coli* bacterium of claim 41, wherein the mineral salts medium contains xylose.

43. The recombinant *E. coli* bacterium of claim 42, wherein the mineral salts medium comprises at least about 9% xylose.

44. The recombinant *E. coli* bacterium of claim 1, wherein the ethanol produced comprises greater than 40% of total non-gaseous fermentation products under anaerobic conditions in mineral salts medium.

45. The recombinant *E. coli* bacterium of claim 1, wherein the *E. coli* bacterium is *E. coli* strain KO11 (ATCC55124) comprising heterologous pdc, adhA and adhB genes.

46. The recombinant *E. coli* bacterium of claim 1, wherein the *E. coli* bacterium is *E. coli* strain SZ110 (NRRL B-30951) comprising heterologous pdc, adhA and adhB genes.

47. The recombinant *E. coli* bacterium of claim 1, wherein the *E. coli* bacterium is *E. coli* strain LY165 (NRRL B-30952).

48. The recombinant *E. coli* bacterium of claim 1, wherein the *E. coli* bacterium is E coil strain LY168 (NRRL B-30953).

49. The recombinant *E. coli* bacterium of claim 1, wherein the *E. coli* bacterium is any one of strains LY149, LY151, LY158, LY159, LY160, LY160im, LY161, LY163, LY168im, LY169, LY170, LY172, LY172im, LY173, LY178, LY180, LY186, BW34-XZ106, BW34-XZ107, BW34-XZ108, BW34-XZ109, BW34-XZ110, BW34-XZ111, BW34-XZ 112, BW34-XZ113, BW34-XZ114, BW34-XZ115, BW34-XZ116, BW34-XZ117, BW34-XZ118, BW34-XZ119, BW34-X7,120, BW34-XZ121, BW34-XZ122, BW34-XZ123, and BW34-XZ12.

50. A method for producing a recombinant *E. coli* bacterium of claim 1, the method comprising the step of integrating a full complement of heterologous ethanol production genes into a host *E. coli* bacterium, thereby producing a recombinant *E. coli* bacterium that comprises a full complement of heterologous ethanol production genes.

51. A method for producing ethanol from an oligosaceharide source, comprising contacting the oligosaccharide with the recombinant *E. coli* bacterium of claim 1 under conditions appropriate for ethanol production, thereby producing ethanol from an oligosaccharide source.

52. A recombinant *E. coli* bacterium which comprises a full complement of heterologous ethanol production genes, wherein said recombinant *E. coli* bacterium is prepared by a process comprising the step of integrating heterologous pdc, adhA and adhB genes into a host *E. coli* bacterium, thereby producing a recombinant *E. coli* bacterium that comprises a full complement of heterologous ethanol production genes.

53. A kit comprising the recombinant *E. coli* bacterium of claim 1 and instructions for use.

54. *Escherichia coli* (*E. coli*) strain SZ110 (NRRL B-30951).

55. *Escherichia coli* (*E. coli*) strain LY168 (NRRL B-30953).

* * * * *

SEQUENCE LISTING

```
<160> NUMBER OF SEQ ID NOS: 80

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ttgctcttcc atgaaactcg ccgtttatag caca                                34

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ttgctcttcg ttaaaccagt tcgttcgggc agg                                 33

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ttgctcttcc atgccaatga ccgaagaata agag                               34
```

```
<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttgctcttcg ttaaactgac gattcaactt tata                               34

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttgctcttcc atgtactatt taaaaaacac aaac                               34

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ttgctcttcg ttaagcgact tcattcacct gac                                33

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ttgctcttcc atggctgtta ctaatgtcgc tgaa                               34

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ttgctcttcg ttaagcggat tttttgcgtt ttttct                             36

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tattgcgctg gtggcacacg                                               20
```

```
<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
acggtccgcg agataacgct                                              20

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agatcttctg gagaatcgaa cgatgtccct g                                 31

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gaattcatca ccgccaagta cagctt                                       26

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
actagtgatc gtaatcggct ggcaat                                       26

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
actagtgttt atgcttccgc cttcac                                       26

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggcgcaatcg ttcatagaga                                              20

<210> SEQ ID NO 16
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
atatggccgt ggccgtatca                                              20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aatgacgatg tgccagaagg                                              20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggtgtcgcgg ttatgacaat                                              20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggacggagaa ggctatgttg                                              20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tgcgaagtga tgcttgagac                                              20

<210> SEQ ID NO 21
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aagcggccgc aaatttccag gcatcaaata a                                 31

<210> SEQ ID NO 22
<211> LENGTH: 31
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 22
aagaacgtgg gaattccctg gcagtttatg g                                       31

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gaagtgacca gcgaataccT                                                    20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggtgatgcct tcggtgatta                                                    20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ttaagctggc actggaactg                                                    20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
agcgacttca ttcacctgac                                                    20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
accgcaccgc atagcgcatt                                                    20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 28
agagctgccg ccagagtgat                                          20

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ttagctagca tgtgacggaa g                                        21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ccgctagcat caaagggaaa a                                        21

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
acgctagcgt gtaatcacgc aggaagg                                  27

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
acgctagctt acatgcgcgc gaaggc                                   26

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
acctcgagtg cacacgctgt tccagacc                                 28

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 34
acgctagcgc gcgttggccg attcatta                                              28

<210> SEQ ID NO 35
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tgagatcttt aaggaaaaac agcatgga                                              28

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gcacaattgc gcgtaacggc gtaatacgaa                                            30

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gacagatctc gatggcgtgt tcagcaacgg                                            30

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ccagtcgcgg tgcattgatt gattctcagg                                            30

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
agctcgagag actgggcggt tttatgg                                               27

<210> SEQ ID NO 40
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
```

-continued aggtatacgc gacacggaaa tgttgaat                                              28

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
acggtgagct ggtgatatgg                                                       20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gcattctgcc gacatggaag                                                       20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tatacgcaag gcgacaaggt                                                       20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tcgtcgtggt attcactcca                                                       20

<210> SEQ ID NO 45
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
atcctgcagt ttccggcagt ttctacaca                                             29

<210> SEQ ID NO 46
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
atcctgcagt ttgcccatgg tgaaaacg                                              28

```
<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
caatccctgg gtgagtttca                                              20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gggaaatagg ccaggttttc                                              20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tttccggcag tttctacaca                                              20

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tttgcccatg gtgaaaacg                                               19

<210> SEQ ID NO 51
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gcagaattcc ctggcaaacc tgatggtat                                    29

<210> SEQ ID NO 52
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gcagaattca ctcagcttgc aggattgct                                    29

<210> SEQ ID NO 53
```

<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
cctggcaaac ctgatggtat					20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
actcagcttg caggattgct					20

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
cgtacaataa aggctccacg a					21

<210> SEQ ID NO 56
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
cacctacctt cttaagtgga ttttt				25

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
tgtccgagct taatgaaaag tt				22

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
cgagtaataa cgtcctgctg ct				22

<210> SEQ ID NO 59
<211> LENGTH: 20
<212> TYPE: DNA

<213> ORGANISM: Artificial Sequence
<220> FEATURE:
<223> OTHER INFORMATION: Description of Artificial Sequence: Synthetic
    primer

<400> SEQUENCE: 59
ggttacttcc accacgaagc                                              20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 60
gtgagtgcgg ttttccagtt                                              20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 61
aaacgggtaa caccccagac                                              20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 62
cggagtgtaa acgtcgaaca                                              20

<210> SEQ ID NO 63
<211> LENGTH: 29
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 63
gcagaattca gccaggatgt tggcttaga                                    29

<210> SEQ ID NO 64
<211> LENGTH: 29
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 64
gcagaattca aaggttcacg gggtctttc                                    29

<210> SEQ ID NO 65
<211> LENGTH: 20
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 65
agccaggatg ttggcttaga                                              20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
aaaggttcac ggggtctttc                                              20

<210> SEQ ID NO 67
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
agcaacaaat gccctgctt                                               19

<210> SEQ ID NO 68
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
caccgtagtg cctcgtcat                                               19

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gccgtagcct gatggataaa                                              20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
acgtcctgct gctgttcttt                                              20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 71
actcagtccg agctgaccat                                           20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
tcacctttcg caaaaccttc                                           20

<210> SEQ ID NO 73
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gcagaattct taagtgggaa acgatgtgg                                 29

<210> SEQ ID NO 74
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gcagaattca aggttcacg gggtctttc                                  29

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
ttaagtggga acgatgtgg                                            20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
aaaggttcac ggggtctttc                                           20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77

```
gaagtgacaa atgccctgct                                              20

<210> SEQ ID NO 78
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
caccgtagtg cctcgtcat                                               19

<210> SEQ ID NO 79
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
gcactacggt gc                                                      12

<210> SEQ ID NO 80
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
ctacggtgct ga                                                      12
```